United States Patent
Tomiyama et al.

(10) Patent No.: US 7,169,761 B2
(45) Date of Patent: Jan. 30, 2007

(54) AZULENE DERIVATIVES AND SALTS THEREOF

(75) Inventors: Hiroshi Tomiyama, Nagano (JP); Atsushi Noda, Nagano (JP); Kayoko Kitta, Chikuma (JP); Yoshinori Kobayashi, Chikuma (JP); Masakazu Imamura, Tsukuba (JP); Takeshi Murakami, Tsukuba (JP); Kazuhiro Ikegai, Tsukuba (JP); Takayuki Suzuki, Tsukuba (JP); Eiji Kurosaki, Tsukuba (JP)

(73) Assignees: Astellas Pharma Inc., Tokyo (JP); Kotobuki Pharmaceutical Co., Ltd., Nagano (JP)

( * ) Notice: Subject to any disclaimer, the term of this patent is extended or adjusted under 35 U.S.C. 154(b) by 23 days.

(21) Appl. No.: 10/491,618

(22) PCT Filed: Aug. 4, 2003

(86) PCT No.: PCT/JP03/09868

§ 371 (c)(1),
(2), (4) Date: Dec. 4, 2004

(87) PCT Pub. No.: WO2004/013118

PCT Pub. Date: Feb. 12, 2004

(65) Prior Publication Data

US 2005/0124555 A1    Jun. 9, 2005

(30) Foreign Application Priority Data

Aug. 5, 2002  (JP) ............................. 2002-226869
May 9, 2003  (JP) ............................. 2003-130991

(51) Int. Cl.
A01N 43/04   (2006.01)
A61K 31/70   (2006.01)
C07H 1/00    (2006.01)
(52) U.S. Cl. ....................................... 514/23; 536/1.11
(58) Field of Classification Search ............... 536/1.11; 514/23

See application file for complete search history.

(56) References Cited

U.S. PATENT DOCUMENTS 6,515,117 B2 * 2/2003 Ellsworth et al. .......... 536/17.2
2001/0041674 A1   11/2001 Tomiyama et al.

FOREIGN PATENT DOCUMENTS

WO   WO 98/31697        7/1998
WO   WO 01/27128 A1     4/2001
WO   WO 02/083066 A2   10/2002
WO   WO 03/099836      12/2003

* cited by examiner

Primary Examiner—Shaojia Anna Jiang
Assistant Examiner—Traviss McIntosh
(74) Attorney, Agent, or Firm—Finnegan, Henderson, Farabow, Garrett & Dunner, L.L.P.

(57) ABSTRACT

The present invention provides an azulene derivative and a salt thereof, wherein an azulene ring is bonded to a benzene ring directly or via a lower alkylene which may be substituted with a halogen atom and the benzene ring is directly bonded to the glucose residue, and it is usable as a $Na^+$-glucose cotransporter inhibitor, especially for a therapeutic and/or preventive agent for diabetes such as insulin-dependent diabetes (type 1 diabetes) and insulin-independent diabetes (type 2 diabetes), as well as diabetes-related diseases such as insulin-resistant diseases and obesity.

10 Claims, No Drawings

AZULENE DERIVATIVES AND SALTS THEREOF

CROSS REFERENCE TO RELATED APPLICATIONS

This application is a National Phase Application based on PCT/JP2003/009868, filed on Aug. 4, 2003, the content of which is incorporated herein by reference, and claims the priority of Japanese Patent Application Nos. 2002-226869, filed on Aug. 5, 2002, and 2003-130991, filed on May 9, 2003.

FIELD OF THE INVENTION

The present invention relates to an azulene derivative of a specific chemical formula and a salt thereof. More particularly, the present invention relates to an azulene derivative which effectively treats or prevents diabetes such as insulin-dependent diabetes (type 1 diabetes), and insulin-independent diabetes (type 2 diabetes), as well as various diabetes-related diseases such as insulin-resistant diseases and obesity, for example, as a pharmaceutical, particularly as a $Na^+$-glucose cotransporter inhibitor, and to a salt thereof.

BACKGROUND OF THE INVENTION

In recent years, a pharmaceutical to inhibit a $Na^+$-glucose cotransporter (SGLT) in the intestinal tract and kidney to reabsorb glucose (a $Na^+$-glucose cotransporter inhibitor) has been demanded as an antidiabetic agent to rapidly normalize hyperglycemia and improve the energy balance in the body. Such a $Na^+$-glucose cotransporter inhibitor has been expected as an excellent pharmaceutical for treating or preventing diabetes such as insulin-dependent diabetes (type 1 diabetes) and insulin-independent diabetes (type 2 diabetes), as well as diabetes-related diseases such as insulin-resistant diseases and obesity.

As compounds used as the $Na^+$-glucose cotransporter inhibitor, phloridzin described in Welch, C. A. et al. (J. Natr., 1989, 119(11) 1698) and a synthetic O-glycoside described in Hongu, M. et al. (Chem. Pharm. Bull., 1998, 46(1) 22) and JP-A-11-21243 are known, for example. These compounds are reported to discharge excess blood glucose into urine and reduce the level of blood glucose by inhibiting a $Na^+$-glucose cotransporter in the kidney.

However, since any of these compounds are an O-glycoside comprising an O-glucoside bond formed between glucose and an aglycon moiety, it has a problem that the hypoglycemic effect is disappeared due to hydrolysis of O-glucoside bond by glucosidase or the like in the small intestine when orally absorbed.

Phloretin, an aglycon moiety of phloridzin, is known to highly inhibit a facilitated diffusion-type glucose transporter. For example, it is reported that the cerebral glucose concentration decreases when phloretin is administered to the vein of a rat (e.g. Stroke, 1983, 14, 388). Phloretin is also known to inhibit a vitamin C transporter (Wang, Y. et al., Biochem. Biophys. Res. Commun., 2000, 267, 488–494).

Therefore, an attempt has been made to use a C-glycoside prepared by converting oxygen in the glucoside bond of the O-glycoside to carbon as the $Na^+$-glucose cotransporter inhibitor.

For example, JP-A-2001-288178 (hereinafter referred to as Patent Document 1) describes that a compound of the following formula has the effect of inhibiting a $Na^+$-glucose cotransporter and is useful as a treating agent or preventing agent for diabetes and a hypoglycemic agent.

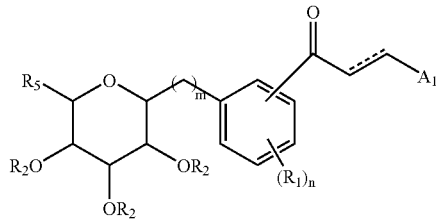

wherein $R_1$ represents H, OH, lower alkyl group, —O-lower alkyl group, or the like, $R_2$ represents H, —COO-lower alkyl group, or the like, $R_5$ represents —$CH_2OH$, —$CH_2OCOO$-lower alkyl group, or the like, $A_1$ represents pyridine, furan, thiophene, quinoline, indole, or the like, n is 0, 1, 2, or 3, and m is 0 or 1 (See Patent Document 1 for further details on the symbols of the above formula).

In addition, the pamphlet of WO 01/27128 (hereinafter referred to Patent Document 2) describes that a compound of the following formula can be used as the $Na^+$-glucose cotransporter inhibitor to treat obesity or type 2 diabetes.

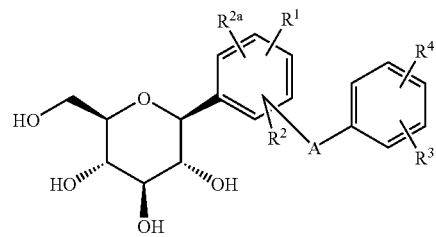

wherein $R^1$, $R^2$, and $R^{2a}$ individually represent a hydrogen atom, OH, $OR^5$, alkyl, $CF_3$, $OCHF_2$, $OCHF_3$, or the like, $R^3$ and $R^4$ individually represent a hydrogen atom, OH, $OR^{5a}$, —O-aryl, —O—$CH_2$-aryl, alkyl, cycloalkyl, $CF_3$, or the like, A represents O, S, NH, or $(CH_2)_n$, and n is 0, 1, 2, or 3 (See Patent Document 2 for further details on the symbols of the above formula).

As explained above, the C-glycoside is useful to a certain extent for treating diabetes due to the effect of inhibiting a $Na^+$-glucose cotransporter. However, due to the recent rise in incidence of diabetes which is a lifestyle-related disease and could even be called a national disease, a compound having a chemical structure different from that of a known compound and showing the effect of inhibiting a $Na^+$-glucose cotransporter more rapidly and more significantly has been increasingly desired for the clinical practice of diabetes treatment or the like.

DISCLOSURE OF THE INVENTION

The present inventors have conducted extensive studies about a compound with a benzene ring directly bonded with a glucose residue and having the effect of inhibiting a $Na^+$-glucose cotransporter. As a result, the inventors have found that a compound (an azulene derivative) having an azulene ring bonded to a benzene ring directly or via a lower alkylene (-A-) which may be substituted with a halogen atom, with the benzene ring being directly bonded to a glucose residue, shown by the following formula (I), has a significant effect of inhibiting a Na$^+$-glucose cotransporter. Specifically, the present invention provides a compound of the following formula (I) and a salt thereof (hereinafter both referred to as "compound of the present invention"). The compound of the present invention can be suitably used as a Na$^+$-glucose cotransporter inhibitor using the compound as an active ingredient, particularly as a therapeutic agent and/or preventive agent for diabetes.

The chemical structure of the compound of the present invention differs from those of Patent Documents 1 and 2 in that the compound of the present invention has an azulene ring, for example.

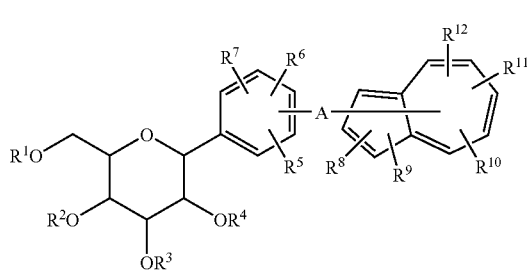
(I)

wherein R$^1$ to R$^4$ individually represent a hydrogen atom, an optionally substituted lower alkyl, —C(=O)-optionally substituted lower alkyl, or -optionally substituted lower alkylene-optionally substituted aryl, R$^5$ to R$^{12}$ individually represent a hydrogen atom, an optionally substituted lower alkyl, halogen atom, —OH, —O—optionally substituted lower alkyl, -optionally substituted lower alkylene-OH, -optionally substituted lower alkylene-O-optionally substituted lower alkyl, —O-optionally substituted lower alkylene-O-optionally substituted lower alkyl, —O-optionally substituted lower alkylene-optionally substituted aryl, -optionally substituted lower alkylene-O—C(=O)-optionally substituted lower alkyl, —COOH, nitro, cyano, amino, substituted amino, or —C(=O)—O-optionally substituted lower alkyl, and A represents a bond or an optionally substituted lower alkylene, wherein -A- may be bonded to any one of the positions 1–8 of the azulene ring, and any two of R$^5$, R$^6$, and R$^7$ may form a benzene ring together with the adjacent carbon atoms.

The term "optionally substituted" used for the definitions of the groups represented by R$^1$ to R$^4$, R$^5$ to R$^{12}$, and A indicates the groups in question may be either substituted or unsubstituted with a halogen atom, —OH, -lower alkylene-OH, —COOH, —C(=O)—O-lower alkyl, nitro, cyano, amino, or substituted amino. A halogen atom, —OH, and —COOH are preferable as a substituent.

The optionally substituted lower alkyl, —C(=O)-optionally substituted lower alkyl, and -optionally substituted lower alkylene-optionally substituted aryl represented by R$^1$ to R$^4$ in the above formula (I) are preferably a lower alkyl, —C(=O)-lower alkyl, and -lower alkylene-aryl, respectively. The optionally substituted lower alkyl, —O-optionally substituted lower alkyl, -optionally substituted lower alkylene-OH, -optionally substituted lower alkylene-O-optionally substituted lower alkyl, —O-optionally substituted lower alkylene-O-optionally substituted lower alkyl, —O-optionally substituted lower alkylene-optionally substituted aryl, -optionally substituted lower alkylene-O—C(=O)- optionally substituted lower alkyl, and —C(=O)—O-optionally substituted lower alkyl represented by R$^5$ to R$^{12}$ in the formula (I) are preferably a lower alkyl, —O-lower alkyl, -lower alkylene-OH, -lower alkylene-O-lower alkyl, —O-lower alkylene-O-lower alkyl, —O-lower alkylene-aryl, -lower alkylene-O—C(=O)-lower alkyl, and —C(=O)—O-lower alkyl, respectively. The optionally substituted lower alkylene represented by A in the above formula (I) is preferably a lower alkylene or a halogen-substituted lower alkylene.

In the compound of the present invention, the group represented by A of the above formula (I) is preferably a lower alkylene, and particularly preferably a methylene.

The groups R$^1$–R$^4$ of the above formula (I) are preferably a hydrogen atom.

The azulene derivative of the above formula (I) may be preferably any one of compounds selected from the group consisting of 1,5-anhydro-1-[3-(azulen-2-ylmethyl)phenyl]hexytol, 1,5-anhydro-1-[5-(azulen-2-ylmethyl)-2-methoxyphenyl]hexytol, 1,5-anhydro-1-[3-(azulen-2-ylmethyl)-5-methoxyphenyl]hexytol, 1,5-anhydro-1-[3-(azulen-2-ylmethyl)-4-methoxyphenyl]hexytol, 1,5-anhydro-1-[5-(azulen-2-ylmethyl)-2-ethoxyphenyl]hexytol, 1,5-anhydro-1-[5-(azulen-2-ylmethyl)-2-methylphenyl]hexytol, 1,5-anhydro-1-[5-(azulen-2-ylmethyl)-2-hydroxyphenyl]hexytol, 1,5-anhydro-1-[5-(azulen-2-ylmethyl)-2-fluorophenyl]hexytol, 1,5-anhydro-1-[5-(azulen-2-ylmethyl)-2,4-dimethoxyphenyl]hexytol, and 1,5-anhydro-1-[4-(azulen-2-ylmethyl)-1-methoxy-2-naphthyl]hexytol.

The present invention also provides a pharmaceutical composition containing the above azulene derivative or the salt thereof as an active ingredient and pharmaceutically acceptable adjuvants.

The pharmaceutical composition of the present invention is effectively used for a Na$^+$-glucose cotransporter inhibitor or a preventing agent or therapeutic agent for diabetes and diabetic complications.

The present invention further provides use of the azulene derivative or the salt thereof for producing a Na$^+$-glucose cotransporter inhibitor or a preventive agent and/or therapeutic agent for diabetes and diabetic complications.

The present invention further provides a therapeutic method for diabetes and diabetic complications comprising administering an effective amount of the above azulene derivative or the salt thereof to a patient.

In the definition of the formulas in this specification, "lower" refers to a linear or branched-carbon chain having 1–6 carbon atoms, unless otherwise specified. Accordingly, examples of a "lower alkyl" include linear or branched alkyls having 1–6 carbon atoms such as a methyl, ethyl, propyl, isopropyl, butyl, isobutyl, sec-butyl, t-butyl, pentyl, isopentyl, hexyl, and isohexyl. Of these, alkyls having 1–3 carbon atoms are preferable, with a methyl and ethyl being particularly preferable.

As a "lower alkylene," in addition to a methylene, ethylene, propylene, and butylene, a branched lower alkylene may be used. Of these, a methylene and ethylene are preferable, with a methylene being particularly preferable.

As a "halogen atom," a fluorine atom, chlorine atom, bromine atom, or iodine atom can be given, with a chlorine atom and bromine atom being preferable. As a "halogen-substituted lower alkyl" or "halogen-substituted lower alkylene," a lower alkyl or lower alkylene substituted with the above halogen atom can be given, with a lower alkyl or lower alkylene substituted with one or more fluorine atoms being particularly preferable.

An "aryl" refers to a monocyclic to tricyclic aromatic hydrocarbon group having 6–14 carbon atoms. Examples of the aryl include a phenyl, naphthyl, anthranyl, and phenanthryl, with a phenyl and naphthyl being particularly preferable. As a "-lower alkylene-aryl," a benzyl and phenethyl are preferable.

As a "substituted amino," an amino group of which one or two hydrogen atoms are substituted with the lower alkyl, an acyl, carbamoyl, or carbamate ($NH_2$—C(=O)—O—) can be given. As the "acyl," a formyl, acetyl, propionyl, butyryl, valeryl, pivaloyl, or the like can be given, with an acetyl being particularly preferable.

-A- in the above formula (I) may be bonded to any one of the positions 1–8 of the azulene ring.

The compound of the present invention includes a mixture or isolated product of various stereoisomers such as a tautomer and an optical isomer.

The compound of the present invention may form an acid-addition salt or, depending on the type of substituent, a salt with a base. Specific examples of such a salt include aid-addition salt with a mineral acid such as hydrochloric acid, hydrobromic acid, hydroiodic acid, sulfuric acid, nitric acid, and phosphoric acid; an organic acid such as formic acid, acetic acid, propionic acid, oxalic acid, malonic acid, succinic acid, fumaric acid, maleic acid, lactic acid, malic acid, tartaric acid, citric acid, methanesulfonic acid, and ethanesulfonic acid; an acidic amino acid such as aspartic acid and glutamic acid; a salt of an inorganic base such as sodium, potassium, magnesium, calcium, and aluminum; an organic base such as methylamine, ethylamine, and ethanolamine; a basic amino acid such as lysine and ornithine; and ammonium salts.

The compound of the present invention further includes hydrates and various pharmaceutically acceptable solvates and polymorphs.

The compound of the present invention should not be limited to the compounds later described in examples, but includes all the compounds of the above formula (I) (azulene derivatives) and the pharmaceutically acceptable salts thereof.

Moreover, the compound of the present invention may includes any prodrug which is converted to any one of compounds of the above formula (I) or salts thereof in the body as a result of the metabolism in the body. As a group for forming the prodrug of the compound of the present invention, a group described in Prog. Med. 5: 2157–2161 (1985) or a group described in "Development of Pharmaceuticals," vol. 7, Molecular Design, 163–198 (Hirokawa Shoten, 1990) can be given. Therefore, the whole contents of those literatures are incorporated herein by reference.

The compound of the present invention or the pharmaceutically acceptable salt thereof can be produced by various known synthesizing methods utilizing characteristics based on the type of its basic structure or substituent. In this case, from the viewpoint of production technique, it may be effective to replace the functional group with a suitable protective group, specifically, a group which can be readily converted to the functional group, at the stage of a starting material or intermediate, depending on the type of functional group. Following this, the protective group is optionally removed to obtain the target compound. Examples of such a functional group include a hydroxyl group and carboxyl group. Examples of the protective group for these functional groups include protective groups described in Greene and Wuts, "Protective Groups in Organic Synthesis," Second Edition. These groups may be suitably used according to the reaction conditions.

PREPARATION EXAMPLES

Typical production processes of the compound of the present invention will be described as follows.

Preparation Example 1

A process of Preparation Example 1 comprises subjecting an azulene compound (1) to a Friedel-Crafts reaction followed by reduction to prepare a compound (2), reacting the compound (2) with a compound (3) by an addition reaction to prepare a compound (4), reducing the compound (4) to prepare a compound (I), and deprotecting the compound (I) to prepare a compound (I'), as shown in the following formula.

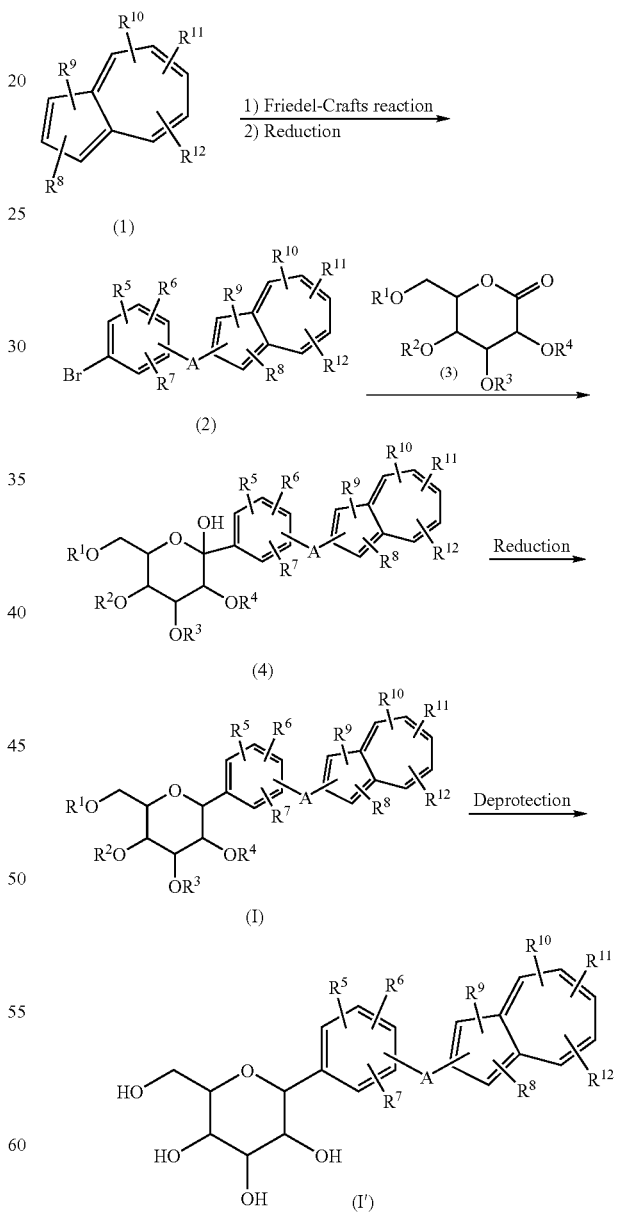

wherein $R^1$ to $R^{12}$ and A are the same as above.

The Friedel-Crafts reaction is carried out in the presence of an appropriate Lewis acid, in the absence of a solvent, or in an appropriate solvent. Specific examples of the Lewis acid include aluminum chloride, boron trichloride, zinc chloride, vanadium chloride, ferric chloride, and stannic chloride. Specific examples of the solvent include ethers such as diethyl ether and tetrahydrofuran; haloalkyls such as chloroform, dichloromethane, and 1,2-dichloroethane; dimethylformamide; dimethylsulfoxide; and a mixture of these solvents. The solvent is appropriately selected according to the type of reaction substrate or the reaction conditions. The reaction temperature is about 20° C. to 180° C., and preferably about 20° C. to 40° C., while it varies according to the type of starting material compounds, the reaction conditions, or the like within the above-mentioned range though.

The subsequent reduction reaction is carried out in the presence of an appropriate reducing agent and acid catalyst in a suitable solvent. Specific examples of the reducing agent include sodium borohydride, sodium cyanoborohydride, and lithium aluminum hydride. Specific examples of the acid include boron trifluoride-diethyl ether complex, trifluoroacetic acid, and trifluoromethanesulfonic acid. Specific examples of the solvent include ethers such as diethyl ether, tetrahydrofuran, and diglyme; haloalkyls such as chloroform, dichloromethane, and 1,2-dichloroethane; and a mixture of these solvents. The solvent is appropriately selected according to the type of reaction substrate or the reaction conditions. The reaction temperature is about 0° C. to 180° C., and preferably about 0° C. to 60° C., while it varies according to the type of starting material compounds, the reaction conditions, or the like within the above-mentioned range though.

The subsequent addition reaction of the compound (2) to the compound (3) is carried out in the presence of an alkyl lithium reagent such as n-butyl lithium, sec-butyl lithium, or t-butyl lithium in a suitable solvent. Specific examples of the solvent include ethers such as diethyl ether, tetrahydrofuran, and diglyme. The solvent is appropriately selected according to the type of reaction substrate or the reaction conditions. The reaction temperature is about −100° C. to 180° C., and preferably about −80° C. to 30° C., while it varies according to the type of starting material compounds, the reaction conditions, or the like within the above-mentioned range though. The compound (4) may also be prepared by reacting the compound (2) with a Grignard reagent prepared using a metal reagent such as magnesium in a suitable solvent. Specific examples of the solvent include ethers such as diethyl ether, tetrahydrofuran, and diglyme. The solvent is appropriately selected according to the type of reaction substrate or the reaction conditions. The reaction temperature is about 20° C. to 180° C., and preferably about 20° C. to 80° C., while it varies according to the type of starting material compounds, the reaction conditions, or the like though.

The subsequent reduction reaction is carried out in the presence of an appropriate reducing agent and acid catalyst in a suitable solvent. Specific examples of the reducing agent include triethylsilane, triisopropylsilane, and t-butyldimethylsilane. Specific examples of the acid catalyst include boron trifluoride-diethyl ether complex, trifluoroacetic acid, and trimethylsilyl trifluoromethanesulfonate. Specific examples of the solvent include haloalkyls such as chloroform, dichloromethane, and 1,2-dichloroethane; ethers such as diethyl ether, tetrahydrofuran, and diglyme; acetonitrile; and a mixture of these solvents. The solvent is appropriately selected according to the type of reaction substrate or the reaction conditions. The reaction temperature is about −100° C. to 180° C., and preferably about −40° C. to 20° C., while it varies according to the type of starting material compounds, the reaction conditions, or the like within the above-mentioned range though.

The deprotection is carried out in the presence of a metal catalyst such as palladium/carbon, palladium hydroxide, or platinum/carbon in a suitable solvent in a hydrogen atmosphere, or in the presence of a Lewis acid in a suitable solvent. Specific examples of the Lewis acid include boron trichloride, boron tribromide, and aluminum trichloride. Specific examples of the solvent include ethers such as tetrahydrofuran and dioxane; esters such as ethyl acetate; alcohols such as methanol and ethanol; acetonitrile; and a mixture of these solvents. The solvent is appropriately selected according to the type of reaction substrate or the reaction conditions. The reaction temperature is about −100° C. to 180° C., and preferably about −80° C. to 30° C., while it varies according to the type of starting material compounds, the reaction conditions, or the like within the above-mentioned range though.

Preparation Example 2

A process of Preparation Example 2 comprises reacting a compound (3) with a compound (5) to prepare a compound (6), reducing the compound (6) to prepare a compound (7), halogenating the compound (7) to prepare a compound (7'), reacting the compound (7') with an azulene derivative (8) to prepare a compound (I), and deprotecting the compound (I) to prepare a compound (I'), as shown in the following scheme.

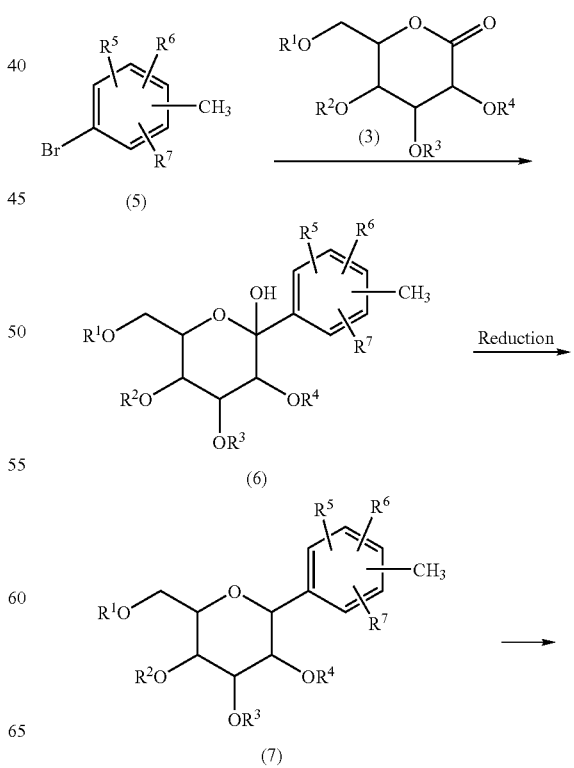

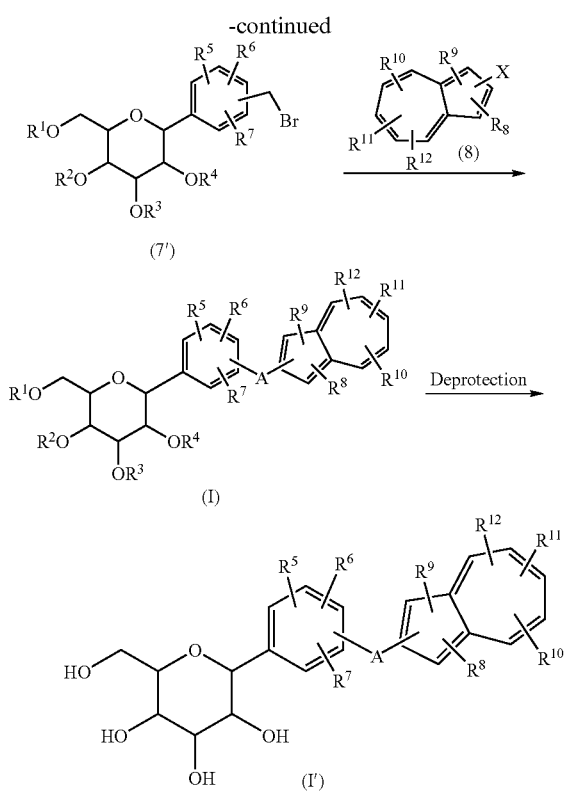

wherein X represents a halogen, B(OR$^{13}$)$_3$, wherein R$^{13}$ is H or a lower alkyl, or SnR$^{14}$$_3$, wherein R$^{14}$ is a lower alkyl.

The reaction of the compound (3) with the compound (5) is carried out in the same manner as in the reaction of the compound (2) with the compound (3) of Preparation Example 1.

The subsequent reduction reaction to prepare the compound (7) is carried out in the same manner as in the reduction reaction of the compound (4) of Preparation Example 1. The subsequent halogenation of the compound (7) to prepare the compound (7') is carried out in the presence of an appropriate halogenating agent in a suitable solvent. Specific examples of the halogenating agent include N-bromosuccinimide, bromine, hydrogen bromide. Specific examples of the solvent include haloalkyls such as methylene chloride, chloroform, and carbon tetrachloride; esters such as ethyl acetate; ethers such as tetrahydrofuran and dioxane; dimethylsulfoxide; acetic acid; water; and a mixture of these solvents. The solvent is appropriately selected according to the type of reaction substrate or the reaction conditions. The reaction temperature is about −100° C. to 180° C., and preferably about 0° C. to 100° C., while it varies according to the type of starting material compounds, the reaction conditions, or the like within the above-mentioned range though.

The subsequent reaction of the compound (7') with the compound (8) is carried out in the presence of an appropriate palladium catalyst or in the presence of an appropriate palladium catalyst and an appropriate phosphine in a suitable solvent. Specific examples of the catalyst include tetrakistriphenylphosphine palladium(0), palladium acetate, bistriphenylphosphine dichloropalladium(II), 1,2-bis(diphenylphosphinoethane)dichloropalladium(II), 1,1'-bis(diphenylphosphinoferrocene)dichloropalladium(II), and tris(dibenzylideneacetone)dipalladium(0). Specific examples of the phosphine include trifurylphosphine, 2-(dicyclohexylphosphino)biphenyl, and tri(t-butyl)phosphine. Specific examples of the solvent include ethers such as diethyl ether, tetrahydrofuran, dioxane, and diglyme; alcohols such as methanol, ethanol, and isopropanol; benzene; toluene; water; and a mixture of these solvents. The solvent is appropriately selected according to the type of reaction substrate or the reaction conditions. The reaction temperature is about −100° C. to 180° C., and preferably about 0° C. to 100° C., while it varies according to the type of starting material compounds, the reaction conditions, or the like within the above-mentioned range though.

This reaction may be carried out by reacting the compound (7') with a metal in a suitable solvent to prepare a metal reagent, and then reacting the reagent with the compound (8) in the presence of a palladium catalyst. Specific examples of the metal include copper, zinc, iron, and magnesium. The palladium catalyst, solvent, and reaction temperature are the same as above.

The deprotection is carried out in the presence of an appropriate base in a suitable solvent. Specific examples of the base include sodium hydroxide, potassium hydroxide, sodium methoxide, and sodium ethoxide. Specific examples of the solvent include ethers such as tetrahydrofuran, dioxane, and diglyme; alcohols such as methanol, ethanol, and isopropanol; acetonitrile; water; and a mixture of these solvents. The solvent is appropriately selected according to the type of reaction substrate or the reaction conditions. The reaction temperature is about −100° C. to 180° C., and preferably about 0° C. to 100° C., while it varies according to the type of starting material compounds, the reaction conditions, or the like within the above-mentioned range though.

The deprotection is also carried out in the presence of an appropriate Lewis acid in a suitable solvent. Specific examples of the Lewis acid include boron trichloride, boron tribromide, and aluminum trichloride. Specific examples of the solvent include ethers such as tetrahydrofuran and dioxane; esters such as ethyl acetate; alcohols such as methanol and ethanol; acetonitrile; and a mixture of these solvents. The solvent is appropriately selected according to the type of reaction substrate or the reaction conditions. The reaction temperature is about −100° C. to 180° C., and preferably about −80° C. to 60° C., while it varies according to the type of starting material compounds, the reaction conditions, or the like within the above-mentioned range though.

Preparation Example 3

A process of Preparation Example 3 comprises protecting an alcohol derivative (9), reacting the protected derivative (9) with a compound (3) to prepare a compound (10), reducing and deprotecting the compound (10) to prepare a compound (11), halogenating the compound (11) to prepare a compound (7'), reacting the compound (7') with an azulene derivative (8) to prepare a compound (I), and deprotecting the compound (I) to prepare a compound (I'), as shown in the following scheme.

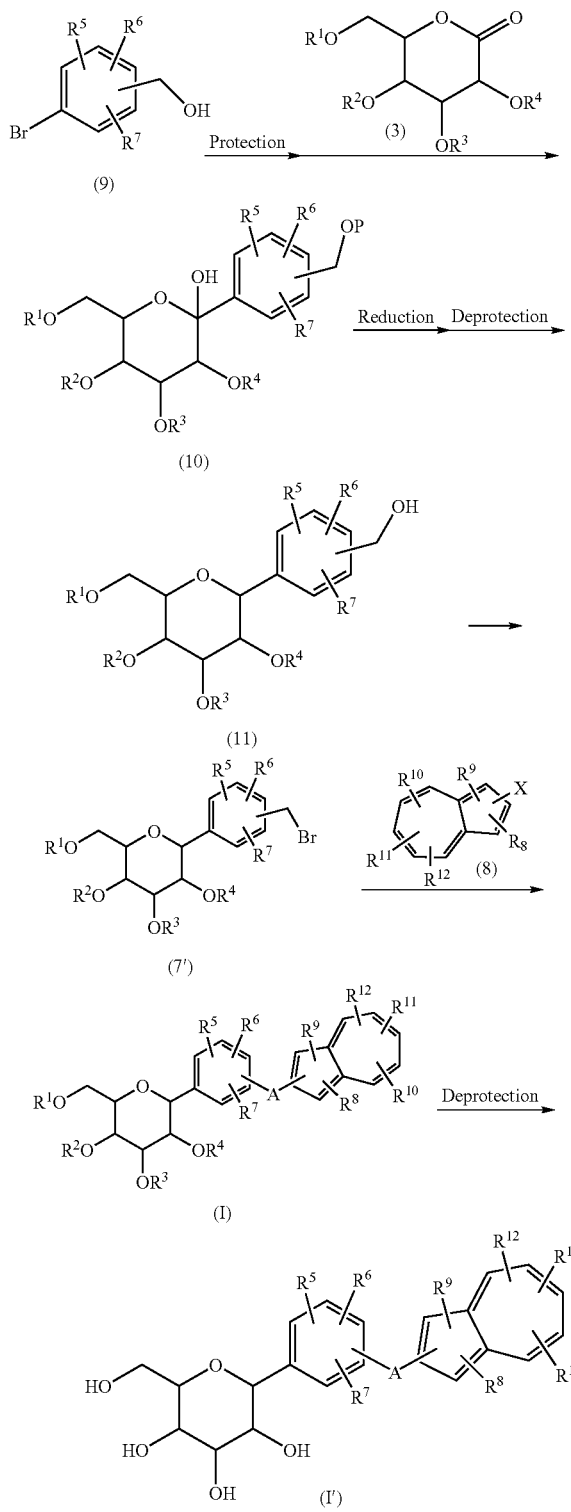

ing to a conventional method. The subsequent reaction with the compound (3) is carried out in the same manner as in the reaction of the compound (2) with the compound (3) of Preparation Example 1.

The subsequent reduction reaction is carried out in the same manner as in the reduction reaction of the compound (4) of Preparation Example 1. The subsequent deprotection is carried out in the presence of an appropriate catalyst in a suitable solvent. Specific examples of the catalyst include tetrabutylammonium fluoride, boron trifluoride-diethyl ether complex, hydrogen fluoride, acetic acid, and p-toluenesulfonic acid. Specific examples of the solvent include ethers such as tetrahydrofuran and dioxane; alcohols such as methanol and ethanol; water; and a mixture of these solvents. The solvent is appropriately selected according to the type of reaction substrate or the reaction conditions. The reaction temperature is about −100° C. to 180° C., and preferably about 20° C. to 80° C., while it varies according to the type of starting material compounds, the reaction conditions, or the like within the above-mentioned range though.

The subsequent halogenation is carried out in the presence of a halogenating agent and triphenyl phosphine in a suitable solvent. Specific examples of the halogenating agent include N-bromosuccinmide, bromine, carbon tetrabromide, and copper (II) bromide. Specific examples of the solvent include haloalkyls such as methylene chloride, chloroform, and carbon tetrachloride; esters such as ethyl acetate; ethers such as tetrahydrofuran and dioxane; benzene; toluene; dimethylsulfoxide; acetic acid; water; and a mixture of these solvents. The solvent is appropriately selected according to the type of reaction substrate or the reaction conditions. The reaction temperature is about −100° C. to 180° C., and preferably about 0° C. to 100° C., while it varies according to the type of starting material compounds, the reaction conditions, or the like within the above-mentioned range though.

The subsequent reaction of the compound (7′) with the compound (8) and the deprotection are carried out in the same manner as in Preparation Example 2.

Preparation Example 4

A process of Preparation Example 4 comprises reacting a bromobenzene derivative (12) with a compound (3) to prepare a compound (13), reducing the compound (13) to prepare a compound (14), converting the compound (14) to a trialkyltin derivative (15), reacting the derivative (15) with an azulene derivative (16) to prepare a compound (I), and deprotecting the compound (I) to prepare a compound (I′), as shown in the following scheme.

wherein P represents a protective group, and X represents a halogen, $B(R^{13})_3$, wherein $R^{13}$ is H or a lower alkyl, or $SnR^{14}_3$, wherein $R^{14}$ is a lower alkyl.

The alcohol derivative (9) is protected by a suitable protective group such as a t-butyldimethylsilyl group, t-butyldiphenylsilyl group, and tetrahydropyranyl group accord-

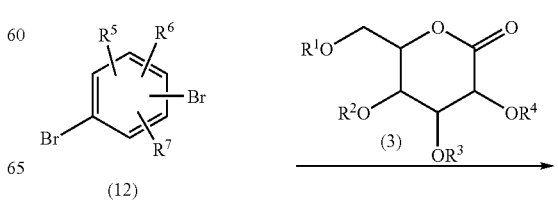

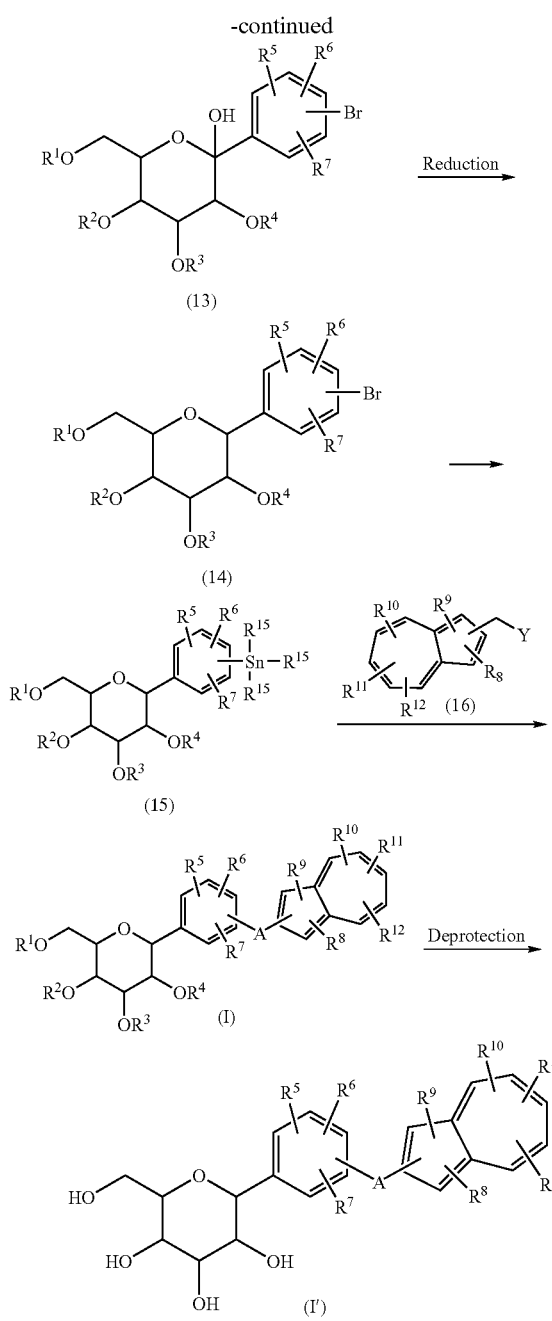

wherein Y represents a halogen and $R^{15}$ represents a lower alkyl.

The reaction of the bromobenzene derivative (12) with the compound (3) is carried out in the same manner as in the reaction of the compound (2) with the compound (3) of Preparation Example 1.

The subsequent reduction reaction is carried out in the same manner as in the reduction reaction of the compound (4) of Preparation Example 1. The subsequent conversion to the trialkyltin derivative is carried out in the presence of hexaalkylditin and an appropriate palladium catalyst in a suitable solvent. Specific examples of the palladium catalyst include tetrakistriphenylphosphine palladium(0), palladium acetate, bistriphenylphosphine dichloropalladium(II), 1,2-bis(diphenylphosphinoethane)dichloropalladium(II), and 1,1'-bis(diphenylphosphinoferrocene)dichloropalladium(II). Specific examples of the solvent include ethers such as diethyl ether, tetrahydrofuran, dioxane, and diglyme; alcohols such as methanol, ethanol, and isopropanol; benzene; toluene; water; and a mixture of these solvents. The solvent is appropriately selected according to the type of reaction substrate or the reaction conditions. The reaction temperature is about −100° C. to 180° C., and preferably about 0° C. to 100° C., while it varies according to the type of starting material compounds, the reaction conditions, or the like within the above-mentioned range though.

The subsequent reaction with the azulene derivative (16) is carried out in the presence of an appropriate palladium catalyst or in the presence of an appropriate palladium catalyst and an appropriate phosphine in a suitable solvent. Specific examples of the catalyst include tetrakistriphenylphosphine palladium(0), palladium acetate, bistriphenylphosphine dichloropalladium(II), 1,2-bis(diphenylphosphinoethane) dichloropalladium(II), 1,1'-bis (diphenylphosphinoferrocene) dichloropalladium(II), and tris(dibenzylideneacetone) dipalladium(0). Specific examples of the phosphine include trifurylphosphine, 2-(dicyclohexylphosphino)biphenyl, and tri(t-butyl)phosphine. Specific examples of the solvent include ethers such as diethyl ether, tetrahydrofuran, dioxane, and diglyme; alcohols such as methanol, ethanol, and isopropanol; benzene; toluene; water; and a mixture of these solvents. The solvent is appropriately selected according to the type of reaction substrate or the reaction conditions. The reaction temperature is about −100° C. to 180° C., and preferably about 0° C. to 100° C., while it varies according to the type of starting material compounds, the reaction conditions, or the like within the above-mentioned range though. The deprotection is carried out in the same manner as in Preparation Example 2.

Preparation Example 5

A process of Preparation Example 5 comprises brominating a phenylacetic acid derivative (17) to prepare a compound (18), converting the compound (18) to a phenylacetone derivative (19), cyclizing the derivative (19) with a compound (20) to prepare a compound (2), reacting the compound (2) with a compound (3) to prepare a compound (4), reducing the compound (4) to prepare a compound (I), and deprotecting the compound (I) to prepare a compound (I'), as shown in the following scheme.

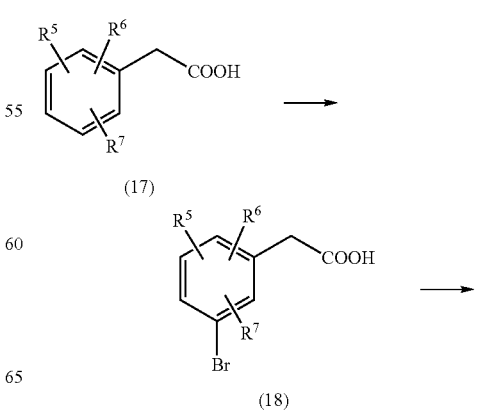

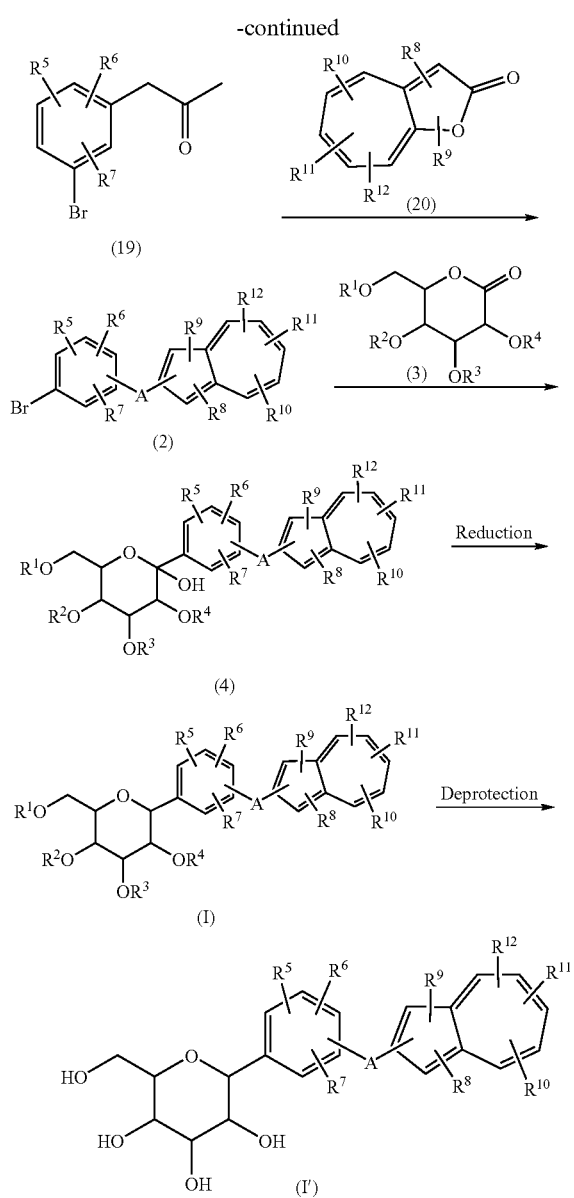

The bromination of the phenylacetic acid derivative (17) is carried out in the presence of an appropriate brominating agent in a suitable solvent. Specific examples of the brominating agent include N-bromosuccinimide, bromine, hydrogen bromide. Specific examples of the solvent include haloalkyls such as methylene chloride, chloroform, and carbon tetrachloride; esters such as ethyl acetate; ethers such as tetrahydrofuran and dioxane; dimethylsulfoxide; acetic acid; water; and a mixture of these solvents. The solvent is appropriately selected according to the type of reaction substrate or the reaction conditions. The reaction temperature is about −100° C. to 180° C., and preferably about 0° C. to 100° C., while it varies according to the type of starting material compounds, the reaction conditions, or the like within the above-mentioned range though.

The subsequent derivation to the phenylacetone derivative (19) is carried out in the presence of an appropriate base in a suitable solvent. Specific examples of the base include sodium acetate, potassium acetate, and pyridine. Specific examples of the solvent include acetic anhydride. The reaction temperature is about −100° C. to 180° C., and preferably about 30° C. to 150° C., while it varies according to the type of starting material compounds, the reaction conditions, or the like within the above-mentioned range though.

The subsequent cyclization reaction is carried out by reacting the compound (19) with a suitable amine in the presence of an appropriate dehydrating agent in a suitable solvent and then reacting the mixture with the compound (20) in a suitable solvent. Specific examples of the amine include morpholine, pyrrolidine, N-methylpiperazine, diethylamine, diisopropylamine. Specific examples of the dehydrating agent include magnesium sulfate and sodium sulfate. Specific examples of the solvent include ethers such as tetrahydrofuran, dioxane, and diethyl ether; haloalkyls such as methylene chloride, chloroform, and carbon tetrachloride; esters such as ethyl acetate; alcohols such as methanol, ethanol, and isopropanol; benzene; toluene; acetonitrile; water; and a mixture of these solvents. The solvent is appropriately selected according to the type of reaction substrate or the reaction conditions. The reaction temperature is about −100° C. to 180° C., and preferably about 20° C. to 120° C., while it varies according to the type of starting material compounds, the reaction conditions, or the like within the above-mentioned range though.

The subsequent addition reaction to the compound (3) and the reduction are carried out in the same manner as in the addition reaction and the reduction of Preparation Example 1.

The deprotection is carried out in the same manner as in Preparation Example 2.

BEST MODE FOR CARRYING OUT THE INVENTION

EXAMPLES

The compound of the present invention will now be described in more detail by way of examples. Since starting material compounds of the compound of the present invention include novel compounds, the methods for preparing these compounds will also be described in reference examples.

Reference Example 1

Aluminum chloride (1.87 g) was added to a solution of 1-methylazulene (2 g) in methylene chloride (20 ml) at 0° C. and the mixture was stirred for 15 minutes. Then, a solution of 3-bromobenzoyl chloride (1.86 ml) in methylene chloride (5 ml) was added dropwise to the reaction mixture at 0° C. and the mixture was stirred for one hour. The reaction mixture was added to 10% aqueous solution of hydrochloric acid under cooling with ice and was extracted with ethyl acetate. The organic layer was washed with saturated brine and dried over anhydrous sodium sulfate. After filtration, the filtrate was concentrated. The residue was purified by silica gel column chromatography (n-hexane-ethyl acetate) to obtain (3-bromophenyl)(3-methylazulen-1-yl)methanone (1.2 g).

Reference Example 2

Boron trifluoride-diethyl ether complex (1.17 ml) was added to a solution of (3-bromophenyl)(1-methylazulen-2-yl) methanone (0.5 g) in diglyme-ether (ratio: 1:1, 2.0 ml) at 0° C. and the mixture was stirred for 20 minutes. Then, sodium borohydride (0.68 g) was added to the reaction mixture and the mixture was stirred at room temperature for one hour. The reaction mixture was added to ice-cooled water and extracted with ethyl acetate. The organic layer was washed with saturated brine and dried over anhydrous sodium sulfate. After filtration, the filtrate was concentrated. The residue was purified by silica gel column chromatography (n-hexane-ether) to obtain 1-(3-bromobenzyl)-3-methylazulene (0.21 g).

Reference Example 3

A 1.6 M hexane solution of n-butyl lithium (2.44 ml) was added dropwise to a solution of 2-(3-bromobenzyl)-1-methylazulene (1.2 g) in THF (8.0 ml) at −78° C. and the mixture was stirred for one hour. Then, a solution of 2,3,4,6-tetra-O-benzyl-D-(+)-glucono-1,5-lactone (2.08 g) in THF (8.0 ml) was added dropwise to the reaction mixture and the mixture was stirred for one hour. Saturated aqueous solution of ammonium chloride was added to the reaction mixture and the mixture was extracted with ethyl acetate. The organic layer was washed with saturated brine and dried over anhydrous sodium sulfate. After filtration, the filtrate was concentrated. The residue was purified by silica gel column chromatography (n-hexane-ethyl acetate) to obtain 2,3,4,6-tetra-O-benzyl-1-C-[3-[(3-methylazulen-1-yl)methyl]phenyl]-D-glucopyranose (1.74 g).

The compounds of Reference Examples 4, 5, and 6 were obtained respectively in the same manner as in Reference Examples 1, 2, and 3.

Reference Example 7

A 1.6 M hexane solution of n-butyl lithium (11 ml) was added dropwise to a solution of 3-bromo-4-ethoxytoluene (3.6 g) in THF (50 ml) at −78° C. and the mixture was stirred for 15 minutes. Then, a solution of 2,3,4,6-tetra-O-benzyl-D-(+)-glucono-1,5-lactone (7.6 g) in THF (10 ml) was added dropwise to the reaction mixture and the mixture was stirred for 2.5 hours. Saturated aqueous solution of ammonium chloride was added to the reaction mixture and the mixture was extracted with ethyl acetate. The organic layer was washed with saturated brine and dried over anhydrous sodium sulfate. After filtration, the filtrate was concentrated. The resulting precipitates were collected by filtration to obtain 2,3,4,6-tetra-O-benzyl-1-C-(2-ethoxy-5-methylphenyl)-D-glucopyranose (3.53 g).

Reference Example 8

Boron trifluoride-diethyl ether complex (0.6 ml) and triethylsilane (1.7 ml) were added dropwise to a solution of 2,3,4,6-tetra-O-benzyl-1-C-(2-ethoxy-5-methylphenyl)-D-glucopyranose (3.5 g) at −50° C. and the mixture was stirred for two hours. Saturated aqueous solution of potassium carbonate was added to the reaction mixture and the mixture was extracted with chloroform. The organic layer was washed with saturated brine and dried over anhydrous sodium sulfate. After filtration, the filtrate was concentrated. The residue was purified by silica gel column chromatography (hexane-ethyl acetate) to obtain (1S)-1,5-anhydro-2,3,4,6-tetra-O-benzyl-1-(2-ethoxy-5-methylphenyl)-D-glucitol (3.4 g).

Reference Example 9

A 1.0 M methylene chloride solution (31.0 ml) of boron trichloride was added dropwise to a solution of (1S)-1,5-anhydro-2,3,4,6-tetra-O-benzyl-1-(2-ethoxy-5-methylphenyl)-D-glucitol (3.4 g) in methylene chloride (50 ml) at −78° C. and the mixture was stirred for 30 minutes. Methanol (10 ml) was added to the reaction mixture and the mixture was stirred for 10 minutes and concentrated. The residue was dissolved in pyridine (20 ml) and acetic anhydride (10 ml) was added to the solution, followed by stirring for 12 hours at room temperature. The reaction mixture was diluted with ethyl acetate. The diluted product was washed with 10% aqueous solution of hydrochloric acid, saturated aqueous solution of sodium hydrogencarbonate, and saturated brine in that order and dried over anhydrous sodium sulfate. After filtration, the filtrate was concentrated. The residue was purified by silica gel column chromatography (n-hexane-ethyl acetate) to obtain (1S)-2,3,4,6-tetra-O-acetyl-1,5-anhydro-1-(2-ethoxy-5-methylphenyl)-D-glucitol (1.3 g).

Reference Example 10

N-bromosuccinimide (1.7 g) and benzoyl peroxide (0.1 g) were added to a solution of (1S)-2,3,4,6-tetra-O-acetyl-1,5-anhydro-1-(2-ethoxy-5-methylphenyl)-D-glucitol (3.7 g) in carbon tetrachloride (30.0 ml) and the mixture was refluxed with heating for one hour. The reaction mixture was diluted with chloroform and the diluted product was washed with saturated aqueous solution of sodium hydrogencarbonate, saturated aqueous solution of sodium thiosulfate, and saturated brine in that order and dried over anhydrous sodium sulfate. After filtration, the filtrate was concentrated. The resulting precipitates were collected by filtration to obtain (1S)-2,3,4,6-tetra-O-acetyl-1,5-anhydro-1-[5-(bromomethyl)-2-ethoxyphenyl]-D-glucitol (1.4 g).

Reference Example 11

A catalytic amount of iodine was added to a suspension of metal magnesium (0.22 g) in THF (5.0 ml) in an argon atmosphere. Then, a solution of the compound in THF (5.0 ml) was added dropwise to the mixture, followed by refluxing with heating for one hour. The Grignard reagent thus prepared was added dropwise to a solution of 3-bromo-4-methylbenzaldehyde dimethylacetal (2.45 g) in THF (5.0 ml) at 0° C. and the mixture was stirred for one hour. An aqueous solution of ammonium chloride was added to the reaction mixture and the mixture was extracted with ethyl acetate. The organic layer was washed with saturated brine and dried over anhydrous sodium sulfate. After filtration, the filtrate was concentrated. The residue was purified by silica gel column chromatography (n-hexane-ethyl acetate) to obtain 2,3,4,6-tetra-O-benzyl-1-C-[5-(dimethoxymethyl)-2-methylphenyl]-D-glucopyranose (2.4 g).

Reference Example 12

Sulfamic acid (0.4 g) and sodium chlorite (0.4 g) were added dropwise to a solution of 2,3,4,6-tetra-O-benzyl-1-C-[5-(dimethoxymethyl)-2-methylphenyl]-D-glucopyranose (2.4 g) in acetone-water (ratio: 5:1, 12 ml) at room temperature and the mixture was stirred for three hours. Acetone was evaporated from the reaction mixture and water was added. The mixture was extracted with ethyl acetate. The organic layer was washed with water and saturated brine in that order and dried over anhydrous sodium sulfate. After filtration, the filtrate was concentrated to obtain 4-methyl-3-[(3R,4S,5R,6R)-3,4,5-tris(benzyloxy)-6-[(benzyloxy)methyl]-2-hydroxytetrahydro-2H-pyran-2-yl]benzoic acid (1.5 g).

The compound of Reference Example 13 was obtained in the same manner as in Reference Example 8.

Reference Example 14

Methyl iodide (0.17 ml) and potassium carbonate (0.4 g) were added to a solution of 4-methyl-3-[(2S,3S,4R,5R,6R)-3,4,5-tris(benzyloxy)-6-[(benzyloxy)methyl]-tetrahydro-2H-pyran-2-yl]benzoic acid (1.5 g) in DMF (10 ml) at room temperature and the mixture was stirred for three hours. The insoluble matter was separated by filtration and the filtrate was diluted with ethyl acetate. The diluted solution was washed with water and saturated brine in that order and dried over anhydrous sodium sulfate. After filtration, the filtrate was concentrated. The residue was purified by silica gel column chromatography (n-hexane-ethyl acetate) to obtain methyl 4-methyl-3-[(2S,3S,4R,5R,6R)-3,4,5-tris(benzyloxy)-6-[(benzyloxy)methyl]-tetrahydro-2H-pyran-2-yl]benzoate (1.3 g).

Reference Example 15

Lithium aluminum hydride (73 mg) was added to a solution of methyl 4-methyl-3-[(2S,3S,4R,5R,6R)-3,4,5-tris(benzyloxy)-6-[(benzyloxy)methyl]tetrahydro-2H-pyran-2-yl]benzoate (1.3 g) in THF (10 ml) at 0° C. and the mixture was stirred for one hour. The reaction mixture was poured into ice-cooled water and the insoluble matter was separated by filtration. The filtrate was extracted with ethyl acetate. The organic layer was washed with saturated brine and dried over anhydrous sodium sulfate. After filtration, the filtrate was concentrated. The residue was purified by silica gel column chromatography (n-hexane-ethyl acetate) to obtain (1S)-1,5-anhydro-2,3,4,6-tetra-O-benzyl-1-[5-(hydroxymethyl)-2-methylphenyl]-D-glucitol (1.0 g).

Reference Example 16

Carbon tetrabromide (0.62 g) and triphenylphosphine (0.49 g) were added to a solution of (1S)-1,5-anhydro-2,3,4,6-tetra-O-benzyl-1-[5-(hydroxymethyl)-2-methylphenyl]-D-glucitol (1.0 g) in methylene chloride (10 ml) at room temperature and the mixture was stirred for one hour. The reaction mixture was concentrated and the residue was purified by silica gel column chromatography (n-hexane-ethyl acetate) to obtain (1S)-1,5-anhydro-2,3,4,6-tetra-O-benzyl-1-[5-(bromomethyl)-2-methylphenyl]-D-glucitol (0.8 g).

The compounds of Reference Examples 17 and 18 were obtained respectively in the same manner as in Reference Examples 1 and 2.

Reference Example 19

A 1.6 M n-hexane solution of n-butyl lithium (14.0 ml) was added dropwise to a solution of (1S)-1,5-anhydro-2,3,4,6-tetra-O-benzyl-1-[3-bromo-5-(methoxymethyl)phenyl]-D-glucitol (7.8 g) in THF (5.0 ml) at −78° C. and the mixture was stirred for 30 minutes. DMF (1.0 ml) was added dropwise to the reaction mixture and the mixture was stirred for four hours. Saturated aqueous solution of ammonium chloride was added to the reaction mixture and the mixture was extracted with ethyl acetate. The organic layer was washed with saturated brine and dried over anhydrous sodium sulfate. After filtration, the filtrate was concentrated. The residue was purified by silica gel column chromatography (n-hexane-ethyl acetate) to obtain methyl 3-methoxymethyl-5-[(2S,3S,4R,5R,6R)-3,4,5-tris(benzyloxy)-6-[(benzyloxy)methyl]-tetrahydro-2H-pyran-2-yl]benzaldehyde (2.6 g).

Reference Example 20

Sodium borohydride (0.15 g) was added to a solution of 3-methoxymethyl-5-[(2S,3S,4R,5R,6R)-3,4,5-tris(benzyloxy)-6-[(benzyloxy)methyl]tetrahydro-2H-pyran-2-yl]benzaldehyde (2.6 g) in a 1:1 mixture of methanol and THF (10 ml) and the mixture was stirred for one hour. Acetone (5.0 ml) was added to the reaction mixture and the mixture was stirred for 10 minutes. Water was added to the reaction mixture and the mixture was extracted with ethyl acetate. The organic layer was washed with saturated brine and dried over anhydrous sodium sulfate. After filtration, the filtrate was concentrated. The residue was purified by silica gel column chromatography (n-hexane-ethyl acetate) to obtain (1S)-1,5-anhydro-2,3,4,6-tetra-O-benzyl-1-[3-(hydroxymethyl)-5-(methoxymethyl) phenyl]-D-glucitol (2.1 g).

The compounds of Reference Examples 21, 22, and 23 were obtained respectively in the same manner as in Reference Examples 6, 11, and Example 1.

Reference Example 24

A 1.0 M THF solution of tetrabutylammonium fluoride (3.8 ml) was added to a solution of (1S)-1,5-anhydro-2,3,4,6-tetra-O-benzyl-1-[3-([[t-butyl(diphenyl)silyl]oxy]methyl)phenyl]-D-glucitol (1.7 g) in THF (10.0 ml) at room temperature and the mixture was stirred for two hours. 10% aqueous solution of sodium hydroxide (3.0 ml) was further added to the reaction mixture and the mixture was refluxed with stirring for one hour. Water was added to the reaction mixture and the mixture was extracted with ethyl acetate. The organic layer was washed with saturated brine and dried over anhydrous sodium sulfate. After filtration, the filtrate was concentrated. The residue was purified by silica gel column chromatography (n-hexane-ethyl acetate) to obtain (1S)-1,5-anhydro-2,3,4,6-tetra-O-benzyl-1-[3-(hydroxymethyl)phenyl]-D-glucitol (0.7 g).

The compound of Reference Example 25 was obtained in the same manner as in Reference Example 16.

Reference Example 26

Imidazole (3.45 g) and t-butyldimethylchlorosilane (17.6 g) were added to a solution of 5-bromo-2-methoxybenzyl alcohol (10.0 g) in DMF (100 ml) under cooling with ice and the mixture was stirred for two hours. The reaction mixture was added to ice-cooled water and extracted with ethyl acetate. The organic layer was washed with saturated brine and dried over anhydrous sodium sulfate. After filtration, the filtrate was concentrated. The residue was purified by silica gel column chromatography (n-hexane-ethyl acetate) to obtain [(5-bromo-2-methoxybenzyl)oxy](t-butyl)dimethylsilane (15.2 g).

The compounds of Reference Examples 27, 28, 29, 30, and 31 were obtained respectively in the same manner as in Reference Example 3, Example 1, Reference Example 16, Reference Example 11, and Example 1.

Reference Example 32

Hexabutylditin (10.0 g) and tetrakistriphenylphosphine palladium (0) (0.24 g) were added to a solution of (1S)-1,5-anhydro-2,3,4,6-tetra-O-benzyl-1-(3-bromophenyl)-D-glucitol (5.0 g) in toluene (8.0 ml) in an argon atmosphere and the mixture was refluxed with stirring for 17 hours. The reaction mixture was concentrated. The residue was purified by silica gel column chromatography (n-hexane-ethyl acetate) to obtain (1S)-1,5-anhydro-2,3,4,6-tetra-O-benzyl-1-[3-(tributylstanyl)phenyl]-D-glucitol (4.0 g).

Reference Example 33

Manganese dioxide (20.4 g) was added to a solution of (1S)-1,5-anhydro-2,3,4,6-tetra-O-benzyl-1-[3-(hydroxymethyl)phenyl]-D-glucitol (6.8 g) obtained in Reference Example 24 in chloroform (100 ml) and the mixture was refluxed with stirring for 1.5 hours. After separating the insoluble matter from the reaction mixture by filtration through celite at room temperature, the filtrate was concentrated. The residue was purified by silica gel column chromatography (n-hexane-ethyl acetate) to obtain 3-[(2S,3S,4R,5R,6R)-3,4,5-tris(benzyloxy)-6-[(benzyloxy)methyl]tetrahydro-2H-pyran-2-yl]benzaldehyde (6.8 g).

Reference Example 34

Potassium t-butoxide (3.6 g) was added to a solution of methyltriphenylphosphonium bromide (11.6 g) in THF (100 ml) at room temperature and the mixture was stirred for 10 minutes. A solution of 3-[(2S,3S,4R,5R,6R)-3,4,5-tris(benzyloxy)-6-[(benzyloxy)methyl]tetrahydro-2H-pyran-2-yl]benzaldehyde (6.8 g) in THF (10 ml) was added dropwise and the mixture was stirred for one hour at room temperature. Saturated aqueous solution of ammonium chloride was added to the reaction mixture and the mixture was extracted with ethyl acetate. The organic layer was washed with saturated brine and dried over anhydrous sodium sulfate. After filtration, the filtrate was concentrated. The residue was purified by silica gel column chromatography (n-hexane-ethyl acetate) to obtain (1S)-1,5-anhydro-2,3,4,6-tetra-O-benzyl-1-(3-vinylphenyl)-D-glucitol (6.8 g).

The compounds of Reference Examples 35, 36, 37, 38, 39, and 40 were obtained respectively in the same manner as in Reference Example 26, Reference Example 3, Example 1, Reference Example 16, Reference Example 3, and Example 1.

Reference Example 41

5% palladium/carbon (1.0 g) was added to a solution of (1S)-1,5-anhydro-2,3,4,6-tetra-O-benzyl-1-(3-bromo-5-methoxyphenyl)-D-glucitol (10.0 g) in THF-methanol (ratio: 1:1, 100 ml). Two drops of a 1 M aqueous solution of hydrochloric acid was further added to the mixture, followed by stirring for 30 minutes in a hydrogen atmosphere. After filtrating the reaction mixture, the filtrate was concentrated. The residue was purified by silica gel column chromatography (chloroform-methanol) to obtain (1S)-1,5-anhydro-1-(3-bromo-5-methoxyphenyl)-D-glucitol (2.9 g).

The compounds of Reference Examples 42, 43, 44, 45, and 46 were obtained respectively in the same manner as in Example 37, Reference Example 32, Reference Example 41, Example 37, and Reference Example 32.

Reference Example 47

1-bromo-2,4-dimethoxybenzene (9.1 ml) was added to a solution of 2,3,4,6-tetra-O-benzyl-1-O-(trifluoroacetyl)-α-D-glucopyranose (20.0 g) in methylene chloride (100 ml) and the mixture was stirred for 10 minutes. Boron trifluoride-diethyl ether complex (3.9 ml) was added to the reaction mixture and the mixture was stirred at room temperature for 12 hours. Water was added to the reaction mixture and the mixture was extracted with methylene chloride. The organic layer was washed with saturated brine and dried over anhydrous sodium sulfate. After filtration, the filtrate was concentrated. The residue was purified by silica gel column chromatography (n-hexane-ethyl acetate) to obtain (1S)-1,5-anhydro-2,3,4,6-tetra-O-benzyl-1-(5-bromo-2,4-dimethoxyphenyl)-D-glucitol (17.0 g).

The compound of Reference Example 48 was obtained in the same manner as in Reference Example 41.

Reference Example 49

Diisopropylethylamine (2.98 g) and chloromethyl methyl ether (1.3 ml) were added to a solution of (1S)-1,5-anhydro-1-(5-bromo-2,4-dimethoxyphenyl)-D-glucitol (1.35 g) in methylene chloride (15 ml) at 0° C. and the mixture was stirred at room temperature for 12 hours. The reaction mixture was added to ice-cooled water and extracted with ethyl acetate. The organic layer was washed with saturated brine and dried over anhydrous sodium sulfate. After filtration, the filtrate was concentrated. The residue was purified by silica gel column chromatography (n-hexane-ethyl acetate) to obtain (1S)-1,5-anhydro-1-(5-bromo-2,4-dimethoxyphenyl)-2,3,4,6-tetrakis-O-(methoxymethyl)-D-glucitol (0.7 g).

The compound of Reference Example 50 was obtained in the same manner as in Reference Example 32.

Reference Example 51

Sodium borohydride (0.26 g) was added to a solution of 6-isopropylazulene-2-carboaldehyde (1.4 g) in methanol (30 ml) at 0° C. and the mixture was stirred for one hour. Acetone was added to the reaction mixture and the mixture was stirred for 15 minutes. The reaction mixture was concentrated. The residue was purified by silica gel column chromatography (n-hexane-ethyl acetate) to obtain (6-isopropylazulen-2-yl)methanol (1.15 g).

Reference Example 52

Triphenylphosphine (0.66 g) was added to a solution of (6-isopropylazulen-2-yl)methanol (0.5 g) in carbon tetrachloride (10.0 ml) and the mixture was refluxed with heating for 15 hours. The reaction mixture was concentrated. The residue was purified by silica gel column chromatography (n-hexane-diethyl ether) to obtain 2-(chloromethyl)-6-isopropylazulene (0.38 g).

The compound of Reference Example 53 was obtained in the same manner as in Reference Example 52.

Reference Example 54

[1,2-bis(diphenylphosphino)ethane]dichloropalladium (II) (1.48 g) was added to a solution of methyl 2-chloroazulene-1-carboxylate (11.38 g) and hexamethylditin (35.9 g) in 1,4-dioxane (272 ml) at room temperature and the mixture was heated to 60° C. and stirred for 38 hours. After evaporating the solvent under reduced pressure, the resulting residue was purified by silica gel column chromatography (hexane-ether acetate) to obtain methyl 2-(tributylstanyl) azulene-1-carboxylate (12.36 g).

Reference Example 55

A 1.0 M dichloromethane solution of tin tetrachloride (16.5 ml) was added to a suspension of 1,2,3,4,6-penta-O-acetyl-β-D-glucopyranose (6.41 g), 1,2-diethoxy-4-methylbenzene (2.47 g), and silver trifluoroacetate (3.63 g) in 1,2-dichloroethane (70 ml) at 0° C. and the mixture was stirred at the same temperature for one hour. After heating to room temperature and stirring for 15 hours, saturated aqueous solution of sodium bicarbonate was added to the mixture. The reaction mixture was filtered through celite and the filtrate was extracted with chloroform. The organic layer was washed with water and saturated brine and dried over anhydrous sodium sulfate. After filtration, the solvent was evaporated under reduced pressure. Methanol (200 ml) and a catalytic amount of sodium methoxide were added to the resulting residue and the mixture was stirred at room temperature overnight. The solvent was evaporated under reduced pressure and the resulting residue was purified by silica gel column chromatography (chloroform-methanol). Pyridine (30 ml), acetic anhydride (5 ml), and a catalytic amount of 4-dimethylaminopyridine were added to the resulting residue and the mixture was stirred at room temperature for two days. Toluene was added to the reaction mixture and the solvent was evaporated under reduced pressure. The residue was purified by silica gel column chromatography (ethyl acetate-n-hexane) to obtain (1S)-2,3,4,6-tetra-O-acetyl-1,5-anhydro-1-(2,3-diethoxy-5-methylphenyl)-D-glucitol (2.51 g).

Reference Example 56

A suspension of (1S)-2,3,4,6-tetra-O-acetyl-1,5-anhydro-1-(2,3-diethoxy-5-methylphenyl)-D-glucitol (500 mg) and N-bromosuccinimide (209 mg) in carbon tetrachloride (10 ml) was refluxed with heating and 2,2'-azobis(isobutyronitrile) (80 mg) was added. The mixture was stirred for 30 minutes under refluxing and the reaction mixture was allowed to be cooled to room temperature. After evaporating the solvent under reduced pressure, the resulting residue was purified by silica gel column chromatography (ethyl acetate-n-hexane) to obtain (1S)-2,3,4,6-tetra-O-acetyl-1,5-anhydro-1-[5-(bromomethyl)-2,3-diethoxyphenyl]-D-glucitol (464 mg).

The compounds of Reference Examples 57 and 58 were obtained respectively in the same manner as in Reference Examples 55 and 56.

Reference Example 59

A 1.56 M n-hexane solution of n-butyl lithium (3.57 ml) and 2-fluorotoluene (0.66 ml) were added in that order to a suspension of potassium t-butoxide (625 mg) in THF (11 ml) at −78° C. and the mixture was stirred at the same temperature for 1.5 hours. A solution of 2,3,4,6-tetra-O-benzyl-D-(+)-glucono-1,5-lactone (3.00 g) in THF (10 ml) was added dropwise to the reaction mixture and the mixture was stirred at the same temperature for 30 minutes. After the addition of a 1 M aqueous solution of hydrochloric acid, the mixture was heated to room temperature. The reaction mixture was extracted with diethyl ether. The organic layer was washed with saturated brine and dried over anhydrous sodium sulfate. After filtration, the solvent was evaporated under reduced pressure. The filtrate was concentrated and dried to be solid. The resulting residue was dissolved in dichloroethane (5 ml) and acetonitrile (25 ml). Triisopropylsilane (2.27 ml) and boron trifluoride-diethyl ether complex (0.85 ml) were added to the solution at −30° C. After stirring at the same temperature for 30 minutes, saturated aqueous solution of sodium bicarbonate was added to the reaction mixture. The mixture was extracted with diethyl ether. The organic layer was washed with saturated brine and dried over anhydrous sodium sulfate. After filtration, the solvent was evaporated under reduced pressure. The resulting residue was purified by silica gel column chromatography (ethyl acetate-n-hexane) to obtain (1S)-1,5-anhydro-2,3,4,6-tetra-O-benzyl-1-(2-fluoro-3-methylphenyl)-D-glucitol (559 mg).

Reference Example 60

A suspension of (1S)-1,5-anhydro-2,3,4,6-tetra-O-benzyl-1-(2-fluoro-3-methylphenyl)-D-glucitol (550 mg) and 20% palladium hydroxide/carbon (300 mg) in THF (10 ml)-methanol (5 ml) was stirred in a hydrogen atmosphere (1 atm) for 2.5 days. The reaction mixture was filtered through celite and the filtrate was concentrated. Pyridine (5 ml), acetic anhydride (2 ml), and a catalytic amount of 4-dimethylaminopyridine were added to the resulting residue and the mixture was stirred at room temperature for one hour. After evaporating the solvent under reduced pressure, the residue was co-evaporated with toluene and dissolved in diethyl ether. This solution was washed with a 1 M aqueous solution of hydrochloric acid and saturated brine and dried over anhydrous sodium sulfate. After filtration, the filtrate was concentrated under reduced pressure to obtain (1S)-2,3,4,6-tetra-O-acetyl-1,5-anhydro-1-(2-fluoro-3-methylphenyl)-D-glucitol (335 mg).

The compounds of Reference Examples 61, 62, 63, 64, and 65 were obtained respectively in the same manner as in Reference Examples 56, 55, 56, 55, and 56.

Reference Example 66

Sodium acetate (50.5 g) was added to a solution of 3-bromo-4-hydroxyphenylacetic acid (28.5 g) in acetic anhydride (100 ml) and the mixture was refluxed with heating for 21 hours. After cooling to room temperature, 20% aqueous solution of sodium hydroxide was added to the reaction mixture to adjust to pH 11. The mixture was refluxed with heating for one hour. After cooling to room temperature, 10% aqueous solution of hydrochloric acid was added to the reaction mixture to adjust to pH 6. The mixture was extracted with ethyl acetate. The organic layer was washed with water, saturated aqueous solution of sodium bicarbonate, and saturated brine and dried over anhydrous sodium sulfate. After filtration, the solvent was evaporated under reduced pressure. The residue was purified by silica gel column chromatography (ethyl acetate-n-hexane) to obtain 1-(3-bromo-4-hydroxyphenyl) acetone (22.2 g).

Reference Example 67

Potassium carbonate (2.7 g) and benzyl bromide (2.3 ml) were added to a solution of 1-(3-bromo-4-hydroxyphenyl) acetone (4.0 g) in DMF (40 ml) and the mixture was stirred at room temperature for six hours. The reaction mixture was poured into water and the mixture was extracted with ethyl acetate. The organic layer was washed with water and saturated brine and dried over anhydrous sodium sulfate.

After filtration, the solvent was evaporated under reduced pressure. The resulting residue was purified by silica gel column chromatography (ethyl acetate-n-hexane) to obtain 1-[4-(benzyloxy)-3-bromophenyl]acetone (3.65 g).

Reference Example 68

Pyrrolidine (1.9 ml) and magnesium sulfate (2.74 g) were added to a solution of 1-[4-(benzyloxy)-3-bromophenyl] acetone (3.65 g) in diethyl ether (30 ml) and the mixture was stirred at room temperature for 12 hours. After filtration, the solvent was evaporated under reduced pressure. The resulting residue was dried under reduced pressure and dissolved in ethanol (30 ml). 2H-cyclohepta[b]furan-2-on (0.5 g) was added to the solution and the mixture was refluxed with heating for eight hours. The reaction mixture was concentrated. The resulting residue was purified by silica gel column chromatography (ethyl acetate-n-hexane) to obtain 2-[4-(benzyloxy)-3-bromobenzyl]azulene (0.84 g).

Reference Example 69

A 1.6 M n-hexane solution of n-butyl lithium (0.32 ml) was added dropwise to a solution of 2-[4-(benzyloxy)-3-bromobenzyl]azulene (0.17 g) in THF (3.0 ml) at −55° C. and the mixture was stirred at the same temperature for 10 minutes. A solution of 2,3,4,6-tetra-O-benzyl-glucono-1,5-lactone (0.12 g) in THF (3.0 ml) was added dropwise to the reaction mixture and the mixture was stirred at the same temperature for 30 minutes. Saturated aqueous solution of ammonium chloride was added to the reaction mixture and the mixture was extracted with ethyl acetate. The organic layer was washed with brine and dried over anhydrous sodium sulfate. After filtration, the solvent was evaporated under reduced pressure. The resulting residue was purified by silica gel column chromatography (ethyl acetate-n-hexane) to obtain 1-C-[5-(azulen-2-ylmethyl)-2-(benzyloxy) phenyl]-2,3,4,6-tetra-O-benzyl-D-glucopyranose (0.9 g).

Example 1

Boron trifluoride-diethyl ether complex (0.39 ml) and triisopropylsilane (1.23 ml) were added dropwise to a solution of 2,3,4,6-tetra-O-benzyl-1-C-[3-[(3-methylazulen-1-yl) methyl]phenyl]-D-glucopyranose (2.3 g) in acetonitrile (40 ml) at −40° C. and the mixture was stirred for two hours. Saturated aqueous solution of potassium carbonate was added to the reaction mixture and the mixture was extracted with ethyl acetate. The organic layer was washed with saturated brine and dried over anhydrous sodium sulfate. After filtration, the filtrate was concentrated. The residue was purified by silica gel column chromatography (n-hexane-ethyl acetate) to obtain (1S)-1,5-anhydro-2,3,4,6-tetra-O-benzyl-1-[3-[(3-methyl azulen-1-yl)methyl]phenyl]-D-glucitol (1.47 g).

Example 2

A 1 M n-heptane solution of boron tribromide (20 ml) was added dropwise to a solution of (1S)-1,5-anhydro-2,3,4,6-tetra-O-benzyl-1-[3-[(3-methylazulen-1-yl)methyl]phenyl]-D-glucitol (0.76 g) in methylene chloride (20 ml) at −78° C. and the mixture was stirred for 30 minutes. Methylene chloride-toluene (ratio: 2:1, 60 ml) was added to the reaction mixture and methanol (6 ml) was further added to the mixture. The reaction mixture was cooled to room temperature and concentrated to the half amount, followed by adding methanol (25 ml) to the mixture and concentrating. This operation was repeated three times. The residue prepared by the concentration was purified by silica gel column chromatography (chloroform-methanol) to obtain (1S)-1,5-anhydro-1-[3-[(3-methylazulen-1-yl)methyl]phenyl]-D-glucitol (0.068 g).

The compounds of Examples 3 and 4 were obtained respectively in the same manner as in Examples 1 and 2.

Example 5

Two drops of 1,2-dibromoethane was added to a suspension of zinc powder (0.17 g) in THF (5.0 ml) in an argon atmosphere and the mixture was refluxed with heating for five minutes. After cooling to room temperature, two drops of chlorotrimethylsilane was added to the reaction mixture. The mixture was stirred for 15 minutes. Next, (1S)-2,3,4,6-tetra-O-acetyl-1,5-anhydro-1-[5-(bromomethyl)-2-ethoxyphenyl]-D-glucitol (1.4 g) was added to the reaction mixture and the mixture was refluxed with heating for one hour. After cooling to room temperature, tetrakistriphenylphosphine palladium (0) (0.27 g) and methyl 2-chloroazulene-1-carboxylate (0.28 g) were added to the reaction mixture. The mixture was refluxed with heating for six hours. After cooling to room temperature, the reaction mixture was poured into 10% aqueous solution of hydrochloric acid under cooling with ice. The mixture was extracted with ethyl acetate. The organic layer was washed with saturated brine and dried over anhydrous sodium sulfate. After filtration, the filtrate was concentrated. The residue was purified by silica gel column chromatography (n-hexane-ethyl acetate) to obtain methyl 2-(4-ethoxy-3-[(2S,3S,4R,5R,6R)-3,4,5-tris(acetyloxy)-6-[(acetyloxy)methyl]tetrahydro-2H-pyran-2-yl]benzyl)azulene-1-carboxylate (0.58 g).

Example 6

10% aqueous solution of sodiumhydroxide (5.0 ml) was added dropwise to a solution of methyl 2-(4-ethoxy-3-[(2S,3S,4R,5R,6R)-3,4,5-tris(acetyloxy)-6-[(acetyloxy) methyl] tetrahydro-2H-pyran-2-yl]benzyl)azulene-1-carboxylate (0.58 g) in methanol (5.0 ml) at room temperature. The mixture was stirred for 30 minutes and refluxed with heating for further six hours. After cooling with ice, the reaction mixture was neutralized by adding 10% aqueous solution of hydrochloric acid. The neutralized product was extracted with chloroform. The organic layer was washed with saturated brine and dried over anhydrous sodium sulfate. After filtration, the filtrate was concentrated. The residue was purified by silica gel column chromatography (chloroform-methanol) to obtain 2-(4-ethoxy-3-[(2S,3R,4R,5S,6R)-3,4,5-tris(acetyloxy)-6-[(acetyloxy)methyl]tetrahydro-2H-pyran-2-yl]benzyl)azulene-1-carboxylic acid (0.4 g).

Example 7 p-Toluenesulfonic acid monohydrate (40 mg) was added to a suspension of 2-(4-ethoxy-3-[(2S,3R,4R,5S,6R)-3,4,5-tris(acetyloxy)-6-[(acetyloxy)methyl]tetrahydro-2H-pyran-2-yl]benzyl)azulene-1-carboxylic acid (0.36 g) inbenzene (10 ml) and the mixture was refluxed with heating for 15 minutes. The reaction mixture was concentrated. The residue was purified by silica gel column chromatography (chloroform-methanol) to obtain (1S)-1,5-anhydro-1-[5-(azulen-2-ylmethyl)-2-ethoxyphenyl]-D-glucitol (203 mg).

The compound of Example 8 was obtained in the same manner as in Example 5.

Example 9

A 1.0 M methylene chloride solution of boron trichloride (3.0 ml) was added dropwise to a solution of methyl 2-(4-methyl-3-[(2S,3S,4R,5R,6R)-3,4,5-tris(benzyloxy)-6-[(benzyloxy)methyl]tetrahydro-2H-pyran-2-yl]benzyl) azulene-1-carboxylate (0.39 g) in methylene chloride (10 ml) at −78° C. and the mixture was stirred for 15 minutes. Methanol (10 ml) was added to the reaction mixture and the mixture was stirred for 10 minutes and concentrated. The residue was purified by silica gel column chromatography (chloroform-methanol) to obtain methyl 2-(4-methyl-3-[(2S,3R,4R,5S,6R)-3,4,5-trihydroxy-6-(hydroxymethyl)tetrahydro-2H-pyran-2-yl]benzyl)azulene-1-carboxylate (0.08 g).

The compounds of Examples 10 and 11 were obtained respectively in the same manner as in Examples 6 and 7.

Example 12

A 1.0 M methylene chloride solution of boron trichloride (3.0 ml) was added dropwise to a solution of methyl 2-(4-methyl-3-[(2S,3S,4R,5R,6R)-3,4,5-tris(benzyloxy)-6-[(benzyloxy)methyl]tetrahydro-2H-pyran-2-yl]benzyl) azulene-1-carboxylate (0.39 g) in methylene chloride (10 ml) at −78° C. and the mixture was stirred for 15 minutes. Methanol (10.0 ml) was added to the reaction mixture and the mixture was stirred for 10 minutes and concentrated. The residue was purified by silica gel column chromatography (chloroform-methanol) to obtain methyl 3-benzyl-2-(4-methyl-3-[(2S,3R,4R,5S,6R)-3,4,5-trihydroxy-6-(hydroxymethyl)tetrahydro-2H-pyran-2-yl]benzyl)azulene-1-carboxylate (0.06 g).

The compounds of Examples 13, 14, 15, and 16 were obtained respectively in the same manner as in Examples 6, 7, 5, and 9.

Example 17

28% methanol solution of sodium methoxide (0.5 ml) was added to a solution of methyl 2-[3-(chloromethyl)-5-[(2S,3R,4R,5S,6R)-3,4,5-trihydroxy-6-(hydroxymethyl) tetrahydro-2H-pyran-2-yl]benzyl]azulene-1-carboxylate (0.06 g) in methanol (3.0 ml) at room temperature. The mixture was stirred for one hour. 10% aqueous solution of sodium hydroxide (3.0 ml) was further added to the reaction mixture and the mixture was refluxed with heating for one hour. After cooling to room temperature, the reaction mixture was neutralized by adding 10% aqueous solution of hydrochloric acid, extracted with chloroform. The organic layer was washed with saturated brine and dried over anhydrous sodium sulfate. After filtration, the filtrate was concentrated. The residue was purified by silica gel column chromatography (chloroform-methanol) to obtain (1S)-1,5-anhydro-1-[3-(azulen-2-ylmethyl)-5-(methoxymethyl)phenyl]-D-glucitol (0.02 g).

The compounds of Examples 18, 19, 20, 21, and 22 were obtained respectively in the same manner as in Examples 5, 9, 6, 7, and 5.

The compounds of Examples 23, 24, 25, 26, and 27 were obtained respectively in the same manner as in Examples 2, 6, 7, 5, and 6.

The compounds of Examples 28, 29, 30, 31, and 32 were obtained respectively in the same manner as in Examples 7, 5, 9, 6, and 7.

Example 33

Potassium carbonate (0.15 g) and bis (triphenylphosphine) dichloropalladium (II) (0.04 g) were added to a solution of (1S)-1,5-anhydro-2,3,4,6-tetra-O-benzyl-1-[3-(tributylstanyl)phenyl]-D-glucitol (0.5 g) and methyl 2-chloroazulene-1-carboxylate (0.1 g) in 1,4-dioxane (3.0 ml) and the mixture was refluxed with heating for 15 hours. The reaction mixture was concentrated. The residue was purified by silica gel column chromatography (n-hexane-ethyl acetate) to obtain methyl 2-(3-[(2S,3S,4R,5R,6R)-3,4,5-tris(benzyloxy)-6-[(benzyloxy)methyl]tetrahydro-2H-pyran-2-yl]phenyl)azulene-1-carboxylate (0.25 g).

The compounds of Examples 34, 35, and 36 were obtained respectively in the same manner as in Examples 2, 6, and 7.

Example 37

Acetic anhydride (0.3 ml) was added to a solution of (1S)-1,5-anhydro-1-[3-(azulen-2-ylmethyl)phenyl]-D-glucitol (0.24 g) in pyridine (5.0 ml) at room temperature and the mixture was stirred for 15 hours. The reaction mixture was diluted with ethyl acetate. The diluted solution was washed with 10% aqueous solution of hydrochloric acid, saturated aqueous solution of sodium hydrogencarbonate, and saturated brine in that order and dried over anhydrous sodium sulfate. After filtration, the filtrate was concentrated. The residue was purified by silica gel column chromatography (n-hexane-ethyl acetate) to obtain (1S)-2,3,4,6-tetra-O-acetyl-1,5-anhydro-1-[3-(azulen-2-ylmethyl)phenyl]-D-glucitol (0.34 g).

Example 38

Aluminum chloride (0.24 g) was added to a solution of (1S)-2,3,4,6-tetra-O-acetyl-1,5-anhydro-1-[3-(azulen-2-ylmethyl)phenyl]-D-glucitol (0.20 g) in methylene chloride (20 ml) at 0° C. and the mixture was stirred for 30 minutes. Next, acetic anhydride (0.17 ml) was added dropwise to the reaction mixture at 0° C. and the mixture was refluxed with stirring for 30 minutes and further 16 hours. The reaction mixture was added to 10% aqueous solution of hydrochloric acid under cooling with ice and was extracted with ethyl acetate. The organic layer was washed with saturated aqueous solution of sodium hydrogencarbonate and saturated brine in that order and dried over anhydrous sodium sulfate. After filtration, the filtrate was concentrated. The residue was purified by silica gel column chromatography (n-hexane-ethyl acetate) to obtain (2S,3S,4R,5R,6R)-2-[3-[(1-acetylazulen-2-yl)methyl]phenyl]-6-[(acetyloxy)methyl]tetrahydro-2H-pyran-3,4,5-triyl triacetate (0.09 g).

Example 39

Sodium methoxide (16 mg) was added to a solution of (2S,3S,4R,5R,6R)-2-[3-[(1-acetylazulen-2-yl)methyl]phenyl]-6-[(acetyloxy)methyl]tetrahydro-2H-pyran-3,4,5-triyl triacetate (0.09 g) in THF-methanol (ratio: 1:1, 6.0 ml) at 0° C. and the mixture was stirred for two hours. After neutralizing with a cation exchange resin, the reaction mixture was added to 10% aqueous solution of hydrochloric acid under cooling with ice. After filtration, the filtrate was concentrated. The residue was purified by silica gel column chromatography (chloroform-methanol) to obtain 1-(2-[3-[(2S,3R,4R,5S,6R)-3,4,5-trihydroxy-6-(hydroxymethyl)tetrahydro-2H-pyran-2-yl]benzyl]azulen-1-yl)ethanone (0.06 g).

The compounds of Examples 40 and 41 were obtained respectively in the same manner as in Reference Example 2 and Example 39.

Example 42

A THF solution (8.0 ml) of 9-borabicyclo[3.3.1]nonane was added to (1S)-1,5-anhydro-2,3,4,6-tetra-O-benzyl-1-(3-vinylphenyl)-D-glucitol (1.0 g) and the mixture was refluxed with heating for four hours. Next, a 3 M aqueous solution of potassium phosphate (1.3 ml) and DMF (12 ml) were added to the reaction mixture. Methyl 2-chloroazulene-1-carboxylate (0.35 g) and 1,1'-diphenylphosphinoferrocene dichloropalladium (II) (0.12 g) were further added to the mixture, followed by stirring at 50° C. for two hours. After cooling to room temperature, the reaction mixture was poured into ice-cooled water and extracted with ethyl acetate. The organic layer was washed with saturated aqueous solution of sodium hydrogencarbonate and saturated brine in that order and dried over anhydrous sodium sulfate. The reaction mixture was concentrated. The residue was purified by silica gel column chromatography (n-hexane-ethyl acetate) to obtain methyl 2-[2(3-[(2S,3S,4R,5R,6R)-3,4,5-tris(benzyloxy)-6-[(benzyloxy)methyl]tetrahydro-2H-pyran-2-yl]phenyl]ethyl]azulene-1-carboxylate (0.88 g).

The compounds of Examples 43, 44, 45, 46, 47, and 48 were obtained respectively in the same manner as in Examples 2, 6, 7, 5, 2, and 6.

The compounds of Examples 49, 50, 51, 52, 53, and 54 were obtained respectively in the same manner as in Examples 7, 33, 39, 2, 6, and 7.

The compounds of Examples 55, 56, 57, 58, and 59 were obtained respectively in the same manner as in Examples 33, 39, 33, 39, and 33.

Example 60

10% aqueous solution of hydrochloric acid (0.5 ml) was added to a solution of (1S)-1,5-anhydro-1-[5-(azulen-2-ylmethyl)-2,4-dimethoxyphenyl]-2,3,4,6-tetrakis-O-(methoxymethyl)-D-glucitol (0.09 g) in methanol (2.0 ml) and the mixture was refluxed with heating for 30 minutes. The reaction mixture was poured into ice-cooled water and extracted with ethyl acetate. The organic layer was washed with saturated brine and dried over anhydrous sodium sulfate. After filtration, the filtrate was concentrated. The residue was purified by silica gel column chromatography (chloroform-methanol) to obtain (1S)-1,5-anhydro-1-[5-(azulen-2-ylmethyl)-2,4-dimethoxyphenyl]-D-glucitol (0.02 g).

Example 61

(1S)-2,3,4,6-tetra-O-acetyl-1,5-anhydro-1-[4-(bromomethyl)-1-methoxy-2-naphthyl]-D-glucitol (0.62 g) was added to a suspension of methyl 2-(tributylstanyl)azulene-1-carboxylate (0.25 g), tris(dibenzylideneacetone)dipalladium (0) (0.05 g), 2-(dicyclohexylphosphino)biphenyl (0.05 g), potassium fluoride (0.09 g), and cesium carbonate (0.35 g) in 1,4-dioxane (20.0 ml). The mixture was stirred at 60° C. for eight hours and at 85° C. for further 14 hours. Insoluble matters were removed by filtration, the filtrate was evaporated to remove the solvent. The residue was purified by silica gel column chromatography to obtain methyl 2-[(4-methoxy-3-[(2S,3S,4R,5R,6R)-3,4,5-tris(acetyloxy)-6-[(acetyloxy) methyl]tetrahydro-2H-pyran-2-yl]-1-naphthyl)methyl]azulene-1-carboxylate (0.34 g).

The compound of Example 62 was obtained in the same manner as in Example 39.

Example 63

A 1 M aqueous solution of sodium hydroxide (12 ml) was added dropwise to a solution of methyl 2-[3-[(1S)-1,5-anhydro-D-glucitol-1-yl]-4-methoxy-1-naphthyl]methyla-zulene-1-carboxylate (0.23 g) in methanol (8.0 ml) and the mixture was refluxed with heating for three hours. A 1 M aqueous solution of hydrochloric acid (12 ml) was added to the reaction mixture under cooling with ice and the solvent was evaporated. The resulting residue was suspended in acetonitrile (15 ml). A 4 M 1,4-dioxane solution of hydrochloric acid (0.4 ml) was added dropwise to the suspension and the mixture was refluxed with heating for 15 minutes. The insoluble matter was removed by filtration and the solvent was evaporated. The resulting residue was purified by silica gel column chromatography and reverse phase column chromatography in that order to obtain (1S)-1,5-anhydro-1-[4-(azulen-2-ylmethyl)-1-methoxy-2-naphthyl]-D-glucitol (0.08 g).

The compounds of Examples 64, 65, and 66 were obtained respectively in the same manner as in Examples 61, 39, and 63.

Example 67

Tris(dibenzylideneacetone)dipalladium (0) (17 mg), 2-(dicyclohexylphosphino)biphenyl (22 mg), potassium fluoride (44 mg), and cesium carbonate (247 mg) were added to a solution of (1S)-2,3,4,6-tetra-O-acetyl-1,5-anhydro-1-[5-(bromomethyl)-2-ethoxy-3-methoxyphenyl]-D-glucitol (327 mg) and methyl 2-(tributylstanyl)azulene-1-carboxylate (180 mg) in 1,4-dioxane (10 ml). The mixture was vigorously stirred at 90° C. for 14 hours. A 1 M aqueous solution of hydrochloric acid was added to the reaction mixture and the mixture was extracted with diethyl ether. The organic layer was washed with saturated brine and dried over anhydrous sodium sulfate. After filtration, the filtrate was concentrated under reduced pressure. The resulting residue was dissolved in THF (4 ml) and MeOH (2 ml), and a 1 M aqueous solution of sodium hydroxide (0.5 ml) was added to the reaction mixture at room temperature. After stirring for 30 minutes, a 1 M aqueous solution of sodium hydroxide (0.5 ml) was further added to the reaction mixture. The mixture was stirred for 30 minutes. The solvent was evaporated under reduced pressure and the resulting residue was purified by silica gel column chromatography (chloroform-methanol). Methanol (2.5 ml) and 10% aqueous solution of sodium hydroxide (2.5 ml) were added to the resulting residue (133 mg) and the mixture was refluxed with heating for one hour. After evaporating the solvent under reduced pressure, ethanol was added. The mixture was filtered. The filtrate was concentrated under reduced pressure. The residue was purified by silica gel column chromatography (chloroform-methanol) to obtain 2-[4-ethoxy-3-methoxy-5-[(2S,3R,4R,5S,6R)-3,4,5-trihydroxy-6-(hydroxymethyl)tetrahydro-2H-pyran-2-yl]benzyl]azulene-1-carboxylic acid (51 mg).

Example 68

Acetonitrile and a 4 M ethyl acetate solution (0.02 ml) of hydrochloric acid (5 ml) were added to 2-[4-ethoxy-3-methoxy-5-[(2S,3R,4R,5S,6R)-3,4,5-trihydroxy-6-(hydroxymethyl) tetrahydro-2H-pyran-2-yl]benzyl]azulene-1- carboxylic acid (50 mg) and the mixture was refluxed with heating for 10 minutes. A 4 M ethyl acetate solution (0.02 ml) of hydrochloric acid was further added to the reaction mixture and the mixture was refluxed with heating for 30 minutes. The reaction mixture was concentrated under reduced pressure. The residue was purified by silica gel column chromatography (chloroform-methanol) to obtain (1S)-1,5-anhydro-1-[5-(azulen-2-ylmethyl)-2-ethoxy-3-methoxyphenyl]-D-glucitol (42 mg).

The compounds of Examples 69, 70, and 71 were obtained respectively in the same manner as in Examples 61, 39, and 63.

Example 72

Tris(dibenzylideneacetone)dipalladium(0) (17 mg), 2-(dicyclohexylphosphino)biphenyl (22 mg), potassium fluoride (44 mg), and cesium carbonate (247 mg) were added to a solution of (1S)-2,3,4,6-tetra-O-acetyl-1,5-anhydro-1-[3-(bromomethyl)-2-fluorophenyl]-D-glucitol (198 mg) and methyl 2-(tributylstanyl)azulene-1-carboxylate (180 mg) in 1,4-dioxane (10 ml) and the mixture was vigorously stirred at 90° C. for 15 hours. The reaction mixture was filtered through celite and the filtrate was concentrated under reduced pressure. The resulting residue was purified by silica gel column chromatography (ethyl acetate-n-hexane). The resulting residue (71 ml) was dissolved in THF-methanol (ratio: 1:1, 6.0 ml). Sodium methoxide (30 mg) was added to the solution and the resulting mixture was stirred at room temperature overnight. The solvent was evaporated under reduced pressure. The residue was purified by silica gel column chromatography (chloroform-methanol) to obtain methyl 2-[2-fluoro-3-[(2S, 3R,4R,5S,6R)-3,4,5-trihydroxy-6-(hydroxymethyl)tetrahydro-2H-pyran-2-yl]benzyl]azulene-1-carboxylate (19 mg).

Example 73

10% aqueous solution of sodium hydroxide (2 ml) was added to a solution of methyl 2-[2-fluoro-3-[(2S,3R,4R,5S,6R)-3,4,5-trihydroxy-6-(hydroxymethyl)tetrahydro-2H-pyran-2-yl]benzyl]azulene-1-carboxylate (19 mg) in methanol (2 ml). The mixture was refluxed with heating for 2 hours. The reaction mixture was neutralized by adding a 4 M ethyl acetate solution of hydrochloric acid and the solvent was evaporated under reduced pressure. Acetonitrile (5 ml) and a 4 M ethyl acetate solution of hydrochloric acid (1 ml) were added to the resulting residue and the mixture was refluxed with heating for 30 minutes. The solvent was evaporated under reduced pressure. The residue was purified by silica gel column chromatography (chloroform-methanol) to obtain (1S)-1,5-anhydro-1-[3-(azulen-2-ylmethyl)-2-fluorophenyl]-D-glucitol (10 mg).

The compound of Example 74 was obtained in the same manner as in Reference Example 8.

Example 75

Aluminum chloride (0.12 g) and anisole (4.0 ml) were added to a solution of (1S)-1,5-anhydro-1-[5-(azulen-2-ylmethyl)-2-(benzyloxy)phenyl]-2,3,4,6-tetra-O-benzyl-D-glucitol (0.07 g) in methylene chloride (5 ml) and the mixture was stirred at room temperature for two hours. The reaction mixture was poured into ice-cooled water and extracted with ethyl acetate. The organic layer was washed with saturated brine and dried over anhydrous sodium sulfate. After filtration, the filtrate was concentrated. The residue was purified by silica gel column chromatography (chloroform-methanol) to obtain (1S)-1,5-anhydro-1-[5-(azulen-2-ylmethyl)-2-hydroxyphenyl]-D-glucitol (0.01 g).

The structural formulas and physicochemical properties of the compounds of Reference Examples and Examples are collectively shown by Tables 1–22 at the end of the present specification.

The following abbreviations can be applied to the tables.

Rf refers to a number of Reference Example, Ex refers to a number of Example, Structure refers to a structural formula, Ac refers to an acetyl group, Bn refers to a benzyl group, Bu refers to a butyl group, Data refers to a property data, NMR refers to a nuclear magnetic resonance spectrum (TMS internal standard), and MS refers to a mass analysis value.

Compounds listed in Table 23 can be easily prepared by in the same manner as in Examples and Preparation Examples or by a method with minor modifications which are obvious for persons having an ordinary skill in the art. Table 23 is given after Tables 1–22.

Industrial Applicability

Since the azulene derivative and the salt thereof (the compounds of the present invention) have the effects of inhibiting a $Na^+$-glucose cotransporter and reducing the level of blood glucose, these compounds are useful for treating or preventing insulin-dependent diabetes (type 1 diabetes), insulin-independent diabetes (type 2 diabetes), insulin-resistant diseases, and obesity, for example, as a pharmaceutical, particularly as a $Na^+$-glucose cotransporter inhibitor.

The significant effects of inhibiting a $Na^+$-glucose cotransporter and reducing the blood glucose of the compound of the present invention have been confirmed in the following pharmacological tests (Test Examples 1 and 2).

Test Example 1

[Inhibition of Human $Na^+$-Glucose Cotransporter (Human SGLT2) Activity]

(1) Preparation of Human SGLT 2 Expression Vector

First, single-strand cDNA was reversely transcribed from total RNA originating from the human kidney (manufactured by BD Biosciences Clontech) using a Superscript II (manufactured by Invitrogen Corporation) and a random hexamer. Second, using the cDNA as a template, a DNA fragment encoding a human SGLT2 (Wells, R. G. et al., Am. J. Physiol., 1992, 263(3) F459) was amplified by the PCR reaction using Pyrobest DNA polymerase (manufactured by Takara Bio Inc.). That is, a Hind III site and an EcoRI site were inserted into the 5' side and the 3' side of the DNA fragment, respectively by using primers.

The amplified fragment was cloned into a pCR2.1-Topo vector using a Topo TA Cloning Kit (manufactured by Invitrogen Corporation) and the cloned vector was transfected into a competent cell of *Escherichia coli* JM109. Ampicillin-resistant clones were cultured in a LB medium containing ampicillin (100 mg/l). A plasmid was purified from the cultured *Escherichia coli* using the method of Hanahan (see Maniatis et al., "Molecular Cloning"). A DNA fragment for encoding a human SGLT2 was obtained by the Hind III/EcoRI digestion of the plasmid and ligated and cloned to the same site of the expression vector pcDNA 3.1 (manufactured by Invitrogen Corporation) using a DNA ligase (manufactured by Roche Diagnostics). The ligated clone was transfected into a competent cell of *Escherichia coli* JM109 in the same manner as described above and cultured in a LB medium containing ampicillin, and a human SGLT2 expression vector was obtained using the method of Hanahan.

(2) Preparation of Human SGLT2 Expressed Cells

The human SGLT2 expression vector was transfected into a CHO-K1 cell using Lipofectamine2000 (manufactured by Invitrogen Corporation). The cell was cultured in a Ham's F12 medium (manufactured by Nissui Pharmaceutical Co., Ltd.) containing penicillin (50 IU/ml, manufactured by Dainippon Pharmaceutical Co., Ltd.), streptomycin (50 μg/ml, manufactured by Dainippon Pharmaceutical Co., Ltd.), Geneticin (40 μg/ml, manufactured by Invitrogen Corporation), and 10% fetal bovine serum in the presence of 5% $CO_2$ at 37° C. for two weeks, and Geneticin-resistant clones were obtained. A cell which stably expresses the human SGLT2, which exhibits sodium-dependent intake of methyl-α-D-glucopyranoside, was obtained (See the following paragraphs for the method for measuring the methyl-α-D-glucopyranoside intake).

(3) Inhibition of Methyl-α-D-Glucopyranoside Intake

After removing the medium of a CHO cell which stably expresses the human SGLT2, a pretreatment buffer solution (buffer solution of pH 7.4 containing choline chloride (140 mM), potassium chloride (2 mM), calcium chloride (1 mM), magnesium chloride (1 mM), 2-[4-(2-hydroxyethyl)1-piperazinyl]ethanesulfonic acid (10 mM), and tris(hydroxymethyl) aminomethane (5 mM)) was added in the amount of 100 μl per well, and incubated at 37° C. for 20 minutes.

11 μl of methyl-α-D-(U-14C) glucopyranoside (manufactured by Amersham Pharmacia Biotech) was mixed with 1,000 μl of a buffer solution for intake containing a test compound (buffer solution of pH 7.4 containing sodium chloride (140 mM), potassium chloride (2 mM), calcium chloride (1 mM), magnesium chloride (1 mM), methyl-α-D-glucopyranoside (50 μM), 2-[4-(2-hydroxyethyl)1-piperazinyl]ethanesulfonic acid (10 mM), and tris(hydroxymethyl)aminomethane (5 mM)) to prepare a buffer solution for intake. A buffer solution for intake without a test compound was prepared for a control group. A buffer solution for basal intake without a test compound containing coline chloride (140 mM) instead of sodium chloride for measuring the basal intake was prepared as well.

After removing the pretreatment buffer solution, the buffer solution for intake was added (25 μl per well) and incubated at 37° C. for two hours. After removing the buffer solution for intake, a buffer solution for washing (buffer solution of pH 7.4 containing choline chloride (140 mM), potassium chloride (2 mM), calcium chloride (1 mM), magnesium chloride (1 mM), methyl-α-D-glucopyranoside (10 mM), 2-[4-(2-hydroxyethyl)1-piperazinyl]ethanesulfonic acid (10 MM), and tris(hydroxymethyl)aminomethane (5 mM)) was added (200 μl per one well). The mixture was immediately removed. This washing operation was carried out once more. 0.5% lauryl sodium sulfate was added (25 μl per well) to solubilize the cells. 75 μl of Microscint 40 (manufactured by PerkinElmer, Inc.) was added to the solubilized cell and the radiation activity was measured using a microscintillation counter TopCount (manufactured by PerkinElmer, Inc.). The value obtained by subtracting the basal intake amount from the intake amount of the control group was defined as 100%. The concentration for 50% inhibition of the above value ($IC_{50}$ value) was calculated from a concentration-inhibition curve using the least squares method. As a result, the compound of the present invention exhibited a strong effect of inhibiting a Na+-glucose cotransporter. The $IC_{50}$ values of typical compounds of the present invention are shown in Table 24.

TABLE 24

| Compound | $IC_{50}$ (nM) |
| --- | --- |
| Example 7 | 16 |
| Example 11 | 29 |
| Example 21 | 99 |
| Example 25 | 22 |
| Example 28 | 16 |
| Example 60 | 5.7 |
| Example 75 | 8.9 |

Test Example 2

[Hypoglycemic Activity Confirmation Test]

Fed KK-$A^y$ mice (CLEA Japan, Inc., male) were used. The test compound was suspended in 0.5% methylcellulose solution to a concentration of 3 mg/10 ml. The weight of each mouse was measured. The test compound suspension was orally administered forcibly to the mice at a dose of 10 ml/kg. Only 0.5% methylcellulose solution was administered to the mice of a control group. Each group consisted of six mice. Blood was collected from the tail vein immediately before administering the compound and one, two, four, and eight hours after administering the compound. The blood glucose value was measured using a glucose CII Test Wako (manufactured by Wako Pure Chemical Industries, Ltd.). The intensity of hypoglycemic activity was determined by calculating the area under the blood glucose value-time curve (AUC) using a trapezoidal method from the glucose value of 0–8 hours after administering the compound and calculating the rate (%) of the decrease in the AUC of the drug-administered group from that of the control group.

As a result, the compound of the present invention exhibited a strong hypoglycemic activity. The hypoglycemic activity of typical compounds of the present invention are shown in Table 25.

TABLE 25

| Compound | Hypoglycemic activity (%) |
| --- | --- |
| Example 28 | 46 |
| Example 60 | 45 |

The pharmaceutical composition containing one or more of the compounds of the present invention and the pharmaceutically acceptable salts thereof is prepared as a tablet, powder, fine granule, granule, capsule, pill, liquid, injection, suppository, ointment, adhesive, or the like using a carrier, vehicle, or other additives commonly used for preparation and is orally or nonorally administered.

The amount of the compound of the present invention to be clinically administered to the human body is appropriately determined, taking the symptoms, weight, age, sex, and the like of a patient to which the compound is administered into consideration, in the range of 0.1–500 mg per day for oral administration or in the range of 0.01–100 mg per day for nonoral administration, once or several times a day. Since the amount to be administered varies according to various conditions, it may be sufficient to administer the compound at a smaller amount than the above-described amount.

As a solid composition for oral administration of the compound of the present invention, a tablet, powder, granule, or the like is used. In such a solid composition, one or more active substances are mixed with at least one inert diluent such as lactose, mannitol, glucose, hydroxypropylcellulose, microcrystal cellulose, starch, polyvinylpyrrolidone, or magnesium aluminometasilicate. The composition may contain additives other than the inert diluent such as a lubricant such as magnesium stearate, a disintegrator such as carboxymethylcellulose calcium, and a solubilizer such as glutamic acid and aspartic acid by a conventional method. The tablet or pill may be optionally coated with a film of glucose or a stomach-soluble or intestines-soluble substance such as sucrose, gelatin, hydroxypropylcellulose, or hydroxypropyl-methylcellulose phthalate.

The liquid composition for oral administration includes pharmaceutically acceptable preparations such as an emulsion preparation, solution preparation, suspension preparation, syrup preparation, elixir preparation, and the like and contains a commonly used inert diluent such as purified water and ethyl alcohol. The composition may contain, in addition to the diluent, adjuvants such as a solubilizer, humectant, and suspending agent, sweetener, flavorer, perfume, and preservative.

The injection for nonoral administration includes a sterilized aqueous or nonaqueous solution, suspension, and emulsion. Examples of the diluent for the aqueous solution or suspension include distilled water and a physiological saline solution for injection. Examples of the diluent for the nonaqueous solution or suspension include propylene glycol, polyethylene glycol, and vegetable oils such as olive oil; alcohols such as ethyl alcohol; and Polysolvate 80 (trade name). Such a composition may further contain additives such as an isotonizing agent, preservative, humectant, emulsifier, dispersant, stabilizer (e.g. lactose), andsolubilizer. These compounds are sterilized by filtering through a bacteria-retaining filter and adding a disinfectant or irradiating, for example. These compounds maybe used by producing a sterilized solid composition and dissolving the composition in a sterilized water or injection solvent before using.

TABLE 1

| Rf. | Structure | Data |
| --- | --- | --- |
| 1 | 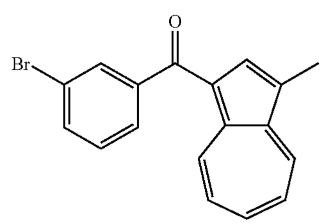 | $^1$H-NMR(CDCl$_3$): 2.63 (3H, s), 7.35–7.39 (1H, m), 7.50 (1H, t), 7.59 (1H, t), 7.67–7.86 (4H, m), 7.96 (1H, s), 8.43 (1H, d), 9.67 (1H, d) |
| 2 | 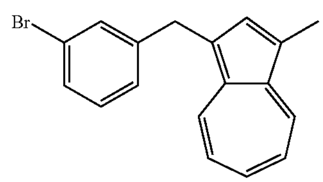 | $^1$H-NMR(CDCl$_3$): 2.63 (3H, s), 4.37 (2H, s), 6.95–7.53 (8H, m), 8.14–8.17 (2H, m) |
| 3 | 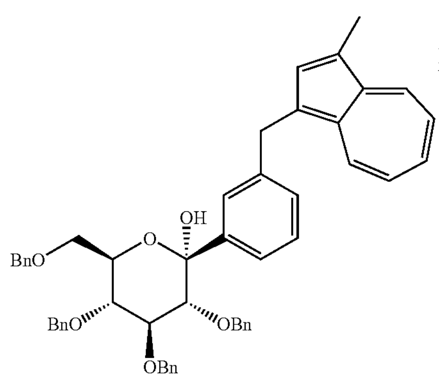 | $^1$H-NMR(CDCl$_3$): 2.56 (3H, s), 2.93 (1H, s), 3.54–4.36 (8H, m), 4.40 (2H, s), 4.50–4.91 (6H, m), 6.87–7.56 (28H, m), 8.13 (3H, dd) |

TABLE 1-continued

| Rf. | Structure | Data |
|---|---|---|
| 4 | 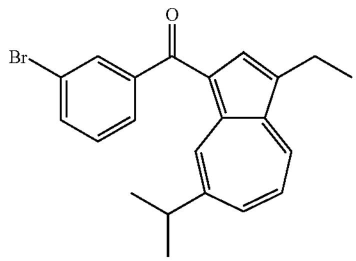 | ¹H-NMR(CDCl₃): 1.35 (3H, t), 1.42 (6H, d), 3.01 (2H, q), 3.22 (1H, q), 7.37 (1H, t), 7.46 (1H, t), 7.67 (1H, d), 7.74 (1H, d), 7.78 (1H, d), 7.88 (1H, s), 7.97 (1H, s), 8.35 (1H, d), 9.76 (1H,d) |
| 5 | 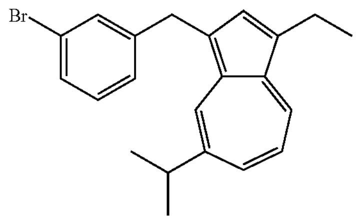 | ¹H-NMR(CDCl₃): 1.30 (6H, d), 1.33 (3H, t), 2.95–3.05 (3H, q), 4.39 (2H, s), 6.96 (1H, t), 7.09–7.16 (2H, m), 7.28–7.31 (1H, m), 7.35–7.43 (2H, m), 7.59 (1H, s), 8.09–8.11 (2H, m) |
| 6 | 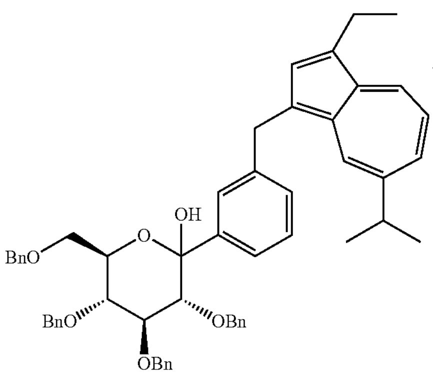 | ¹H-NMR(CDCl₃): 1.24–1.29 (9H, t), 2.95–2.98 (3H, q), 3.55–5.01 (17H, m), 6.91–7.52 (26H, m), 7.60 (1H, s), 8.07 (1H, d), 8.16 (1H, d) |
| 7 | 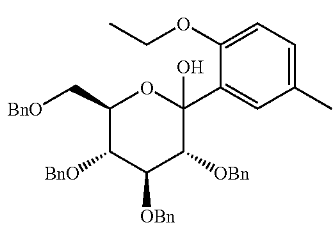 | ¹H-NMR(CDCl₃): 1.30 (3H, t), 2.27 (3H, s), 3.73 (3H, dd), 3.84–4.01 (5H,m), 4.10 (1H,t), 4.20 (1H, m), 4.52 (2H, m), 4.67 (2H, m), 4.91 (3H, m), 6.77 (1H, d), 6.98 (2H, m), 7.01 (1H, dd), 7.16–7.38 (19H, m) |

TABLE 2

| Rf. | Structure | Data |
|---|---|---|
| 8 | 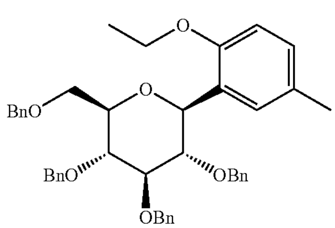 | ¹H-NMR(CDCl₃): 1.34 (3H, t), 2.28 (3H, s), 3.60 (1H, m), 3.79 (4H, m), 3.96 (3H, m), 4.40 (1H, d), 4.53 (1H, d), 4.67 (2H, m), 4.63 (2H, m), 4.89 (2H, m), 4.95 (1H, d), 6.76 (1H, d), 6.90 (2H, m), 7.04 (1H, dd), 7.15–7.35 (19H, m) |

TABLE 2-continued

| Rf. | Structure | Data |
| --- | --- | --- |
| 9 | (structure) | $^1$H-NMR(CDCl$_3$): 1.43 (3H, t), 1.77 (3H, s), 2.01 (3H, s), 2.05 (3H, s), 2.08 (3H, s), 2.27 (3H, s), 3.83 (1H, m), 4.01 (2H, q), 4.14 (1H, m), 4.27 (1H, dd), 4.93 (1H, d), 5.22 (1H, t), 5.35 (2H, m), 6.73 (1H, d), 7.03 (1H, d), 7.16 (1H, s) |
| 10 | (structure) | $^1$H-NMR(CDCl$_3$): 1.46 (3H, t), 1.78 (3H, s), 2.01 (3H, s), 2.06 (3H, s), 2.09 (3H, s), 3.84 (1H, m), 4.05 (2H, q), 4.14 (1H, d), 4.27 (1H, dd), 4.46 (1H, ABq), 4.48 (1H, ABq), 4.87 (1H, m), 5.22 (1H, m), 5.35 (2H, m), 6.80 (1H, d), 7.29 (1H, dd), 7.37 (1H, s) |
| 11 | (structure) | $^1$H-NMR(CDCl$_3$): 2.53 (3H, s), 3.28 (6H, s), 3.84–4.15 (6H, m), 4.34–4.90 (8H, m), 5.36 (1H, s), 6.95 (2H, d), 7.15–7.38 (20H, m), 7.80 (1H, s) |
| 12 | (structure) | ESI-MS(m/z): 673[M−H]$^-$ |
| 13 | (structure) | ESI-MS(m/z): 657[M−H]$^-$ |
| 14 | (structure) | $^1$H-NMR(CDCl$_3$): 2.41 (3H, s), 3.63 (2H, m), 3.76–3.83 (5H, m), 3.90 (3H, s), 4.41 (1H, d), 4.54–4.66 (4H, m), 4.86–4.94 (3H, m), 6.85 (2H, m), 7.15–7.36 (19H, m), 7.89 (1H, dd), 8.17 (1H, d) |
| 15 | (structure) | $^1$H-NMR(CDCl$_3$): 2.39 (3H, s), 3.45 (1H, s), 3.62 (2H, m), 3.76–3.83 (4H, m), 4.37 (1H, d), 4.53–4.65 (5H, m), 4.86–4.94 (3H, m), 6.86 (2H, m), 7.15–7.34 (20H, m), 7.44 (1H, s) |

TABLE 3

| Rf. | Structure | Data |
|---|---|---|
| 16 | (structure) | ¹H-NMR(CDCl$_3$): 2.37 (3H, s), 3.61 (2H, m), 3.80 (4H, m), 4.37 (1H, d), 4.48–4.66 (6H, m), 4.86–4.94 (3H, m), 6.88 (2H, m), 7.12–7.35 (20H, m), 7.51 (1H, s) |
| 17 | (structure) | ¹H-NMR(CDCl$_3$): 3.06 (1H, d), 3.36 (3H, s), 3.50 (1H, dd), 3.73 (1H, m), 3.82 (2H, m), 3.90 (1H, d), 4.05 (1H, m), 4.18 (1H, m), 4.39 (2H, s), 4.48–4.67 (4H, m), 4.86 (1H, d), 4.92 (2H, s), 6.98 (2H, m), 7.20–7.37 (18H, m), 7.48 (1H, d), 7.49 (1H, d), 7.70 (1H, t) |
| 18 | (structure) | ¹H-NMR(CDCl$_3$): 3.36 (3H, s), 3.43 (1H, t), 3.57–3 p.97 (5H, m), 4.37–4.97 (10H, m), 5.11 (1H, d), 6.94–7.81 (23H, m) |
| 19 | (structure) | ¹H-NMR(CDCl$_3$): 3.39 (3H, s), 3.49 (1H, m), 3.62 (1H, m), 3.74–3.83 (4H, m), 4.33 (1H, d), 4.47–4.71 (7H, m), 4.87 (1H, d), 4.93 (2H, d), 6.88 (2H, m), 7.15–7.37 (18H, m), 7.67 (1H, s), 7.82 (1H, s), 7.86 (1H, s), 9.97 (1H, s) |
| 20 | (structure) | ¹H-NMR(CDCl$_3$): 3.37 (3H, s), 3.50 (1H, t), 3.62 (1H, m), 3.77 (4H, m), 4.26 (1H, d), 4.43 (1H, d), 4.46 (2H, s), 4.55–4.72 (6H, m), 4.87 (1H, d), 4.90 (1H, d), 4.95 (1H, d), 6.91 (2H, m), 7.18–7.54 (21H, m) |

TABLE 3-continued

| Rf. | Structure | Data |
|---|---|---|
| 21 | 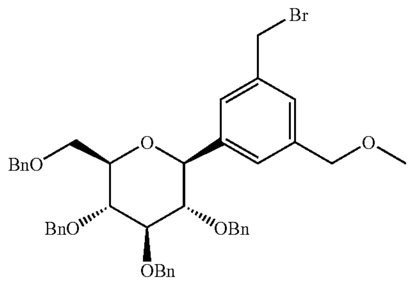 | ¹H-NMR(CDCl₃): 3.37 (3H, s), 3.50 (1H, t), 3.60 (1H, m), 3.79 (5H, m), 4.24 (1H, d), 4.41–4.66 (8H, m), 4.86 (1H, d), 4.90 (1H, d), 4.95 (1H, d), 6.92 (2H, m), 7.18–7.41 (21H, m) |
| 22 | 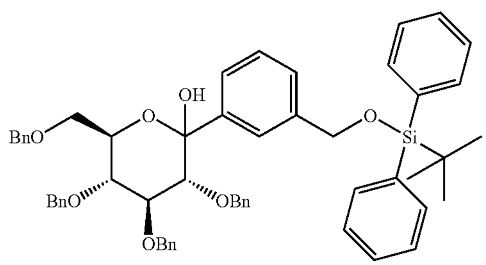 | ¹H-NMR(CDCl₃): 1.47 (1H, t), 3.48–3.81 (6H, m), 4.25–4.97 (8H, m), 6.90–7.42 (34H, m) |

TABLE 4

| Rf. | Structure | Data |
|---|---|---|
| 23 | 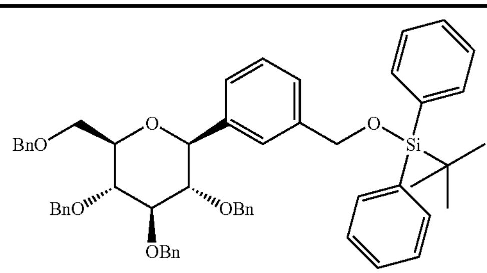 | ¹H-NMR(CDCl₃): 1.09 (9H, s), 3.47–3.80 (7H, m), 4.22–4.97 (8H, m), 4.88 (2H, s), 6.88–7.70 (34H, m) (1H, t) |
| 24 | 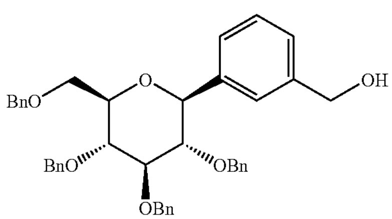 | ¹H-NMR(CDCl₃): 1.47 (1H, t), 3.48–3.82 (7H, m), 4.25–4.97 (10H, m), 6.90–7.42 (24H, m) |
| 25 | 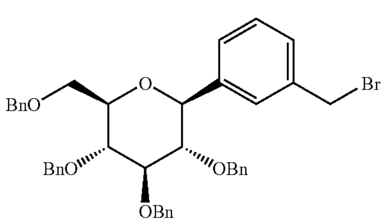 | ¹H-NMR(CDCl₃): 3.48–3.82 (7H, m), 4.23–4.97 (10H, m), 6.91–7.48 (24H, m) |
| 26 | 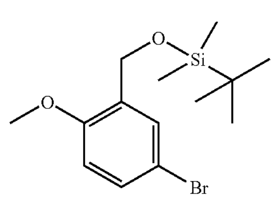 | ¹H-NMR(CDCl₃): 0.12 (6H, s), 0.96 (9H, s), 3.79 (3H, s), 4.70 (2H, s), 6.69 (1H, d), 7.31 (1H, dd), 7.56 (1H, d) |

TABLE 4-continued

| Rf. | Structure | Data |
|---|---|---|
| 27 | (structure) | $^1$H-NMR(CDCl$_3$): 0.93 (9H, s), 2.97 (1H, s), 3.54–4.13 (9H, m), 4.36–4.93 (10H, m), 6.81 (1H, d), 7.01–7.75 (22H, m) |
| 28 | (structure) | $^1$H-NMR(CDCl$_3$): 2.14 (1H, t), 3.46–3.84 (7H, m), 3.89 (3H, s), 4.19–4.97 (10H, m), 6.88 (1H, d), 6.93–7.38 (22H, m) |
| 29 | (structure) | $^1$H-NMR(CDCl$_3$): 3.49–3.88 (7H, m), 3.91 (3H, s), 4.17–4.96 (10H, m), 6.85–7.41 (23H, m) |

TABLE 5

| Rf. | Structure | Data |
|---|---|---|
| 30 | (structure) | $^1$H-NMR(CDCl$_3$): 3.03 (1H, s), 3.49–4.92 (14H, m), 6.97–7.79 (24H, m) |
| 31 | (structure) | $^1$H-NMR(CDCl$_3$): 3.41–3.84 (7H, m), 4.19–4.97 (8H, m), 6.97–7.79 (24H, m) |
| 32 | (structure) | $^1$H-NMR(CDCl$_3$): 0.84–1.55 (27H, m), 3.52–3.83 (7H, m), 4.21–4.96 (8H, m), 6.88–7.54 (24H, m) |

TABLE 5-continued

| Rf. | Structure | Data |
|---|---|---|
| 33 | (2,3,4,6-tetra-O-benzyl-β-D-glucopyranosyl)-3-formylbenzene | ¹H-NMR(CDCl₃): 3.45–3.86 (7H, m), 4.32–4.94 (8H, m), 6.86–7.93 (24H, m), 9.97 (1H, s) |
| 34 | (2,3,4,6-tetra-O-benzyl-β-D-glucopyranosyl)-3-vinylbenzene | ¹H-NMR(CDCl₃): 3.48–3.83 (7H, m), 4.24–4.98 (8H, m), 5.26 (1H, d), 5.75 (1H, d), 6.74 (1H, m), 6.89–7.50 (24H, m) |
| 35 | 3-bromo-4-fluorobenzyl tert-butyldimethylsilyl ether | ¹H-NMR(CDCl₃): 0.92 (9H, s), 7.05 (1H, t), 7.18–7.24 (1H, m), 7.49 (1H, dd) |
| 36 | glucopyranose with 2-fluoro-5-(TBS-oxymethyl)phenyl and OH | ¹H-NMR(CDCl₃): 0.10 (6H, m), 0.94 (9H, s), 3.56–4.89 (17H, m), 6.92–7.60 (23H, m) |

TABLE 6

| Rf. | Structure | Data |
|---|---|---|
| 37 | (2,3,4,6-tetra-O-benzyl-β-D-glucopyranosyl)-2-fluoro-5-(hydroxymethyl)benzene | ESI-MS(m/z): 666[M+NH₄]⁺ |
| 38 | (2,3,4,6-tetra-O-benzyl-β-D-glucopyranosyl)-5-(bromomethyl)-2-fluorobenzene | ¹H-NMR(CDCl₃): 3.60–4.00 (7H, m), 4.41–4.95 (10H, m), 6.90–7.51 (23H, m) |

TABLE 6-continued

| Rf. | Structure | Data |
|---|---|---|
| 39 | (structure) | ¹H-NMR(CDCl₃): 3.05 (1H, s), 3.48–4.15 (6H, m), 3.71 (3H, s), 4.50–4.92 (8H, m), 6.99–7.38 (23H, m) |
| 40 | (structure) | ¹H-NMR(CDCl₃): 3.40–4.19 (1H, m), 4.46–4.97 (7H, m), 6.90–7.35 (23H, m) |
| 41 | (structure) | ¹H-NMR(CDCl₃): 3.27–3.90 (6H, m), 3.79 (3H, s), 4.09 (1H, d), 6.97–7.01 (2H, m), 7.19 (1H, t) |
| 42 | (structure) | ¹H-NMR(CDCl₃): 1.88 (3H, t), 2.00 (3H, s), 2.06 (3H, s), 2.10 (3H, s), 3.79 (3H, s), 3.80–3.84 (1H, m), 4.15–5.33 (6H, m), 6.84 (1H, t), 6.99 (1H, t), 7.06 (1H, t) |
| 43 | (structure) | ¹H-NMR(CDCl₃): 0.87–1.56 (27H, m), 1.80 (3H, s), 2.00 (3H, s), 2.06 (3H, s), 2.08 (3H, s), 3.80 (3H, s), 3.82–5.36 (7H, m), 6.83–6.95 (3H, m) |

TABLE 7

| Rf. | Structure | Data |
|---|---|---|
| 44 | 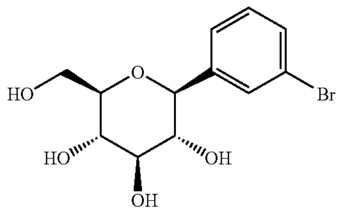 | ESI-MS(m/z): 320[M+H]$^+$ |
| 45 | 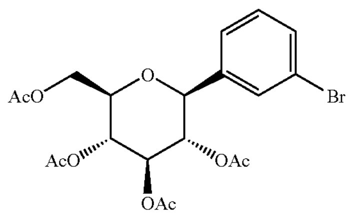 | $^1$H-NMR(CDCl$_3$): 1.86 (3H, s), 2.04 (3H, s), 2.06 (3H, s), 2.10 (3H, s), 3.82–5.35 (7H, m), 7.20–7.28 (2H, m), 7.46 (1H, d), 7.49 (1H, s) |
| 46 | 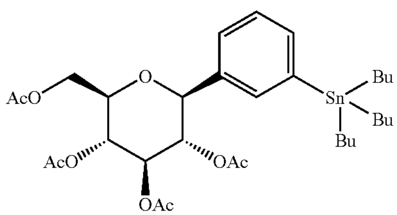 | $^1$H-NMR(CDCl$_3$): 0.87–1.56 (27H, m), 1.78 (3H, s), 2.00 (3H, s), 2.06 (3H, s), 2.08 (3H, s), 3.82–5.36 (7H, m), 7.30–7.41 (4H, m) |
| 47 | 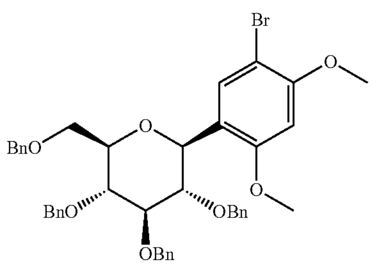 | $^1$H-NMR(CDCl$_3$): 3.57–3.83 (6H, m), 3.76 (3H, s), 3.92 (3H, s), 4.03 (1H, d), 4.47–4.96 (8H, m), 6.42 (1H, s), 6.90–7.34 (20H, m), 7.56 (1H, s) |
| 48 | 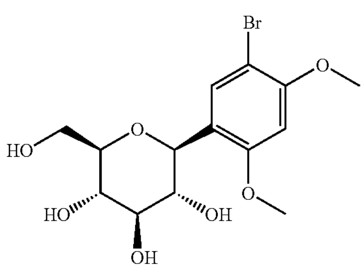 | $^1$H-NMR(CDCl$_3$): 3.33–3.75 (6H, m), 3.85 (3H, s), 3.89 (3H, s), 4.16 (1H, t), 4.41 (1H, d), 4.56 (1H, d), 4.66 (1H, d), 4.74 (1H, d), 6.55 (1H, s), 7.47 (1H, s) |
| 49 | 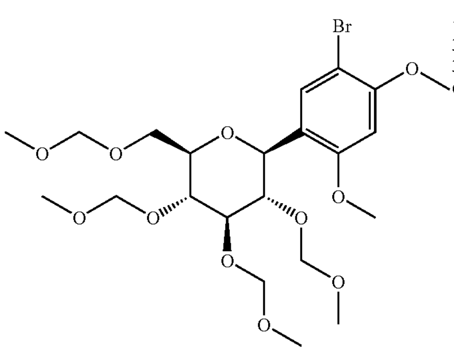 | $^1$H-NMR(CDCl$_3$): 2.84 (3H, s), 3.34 (3H, s), 3.44 (3H, s), 3.45 (3H, s), 3.57–3.92 (7H, m), 3.83 (3H, s), 3.89 (3H, s), 4.24–4.92 (8H, m), 6.43 (1H, s), 7.54 (1H, s) |

TABLE 8

| Rf. | Structure | Data |
|---|---|---|
| 50 | 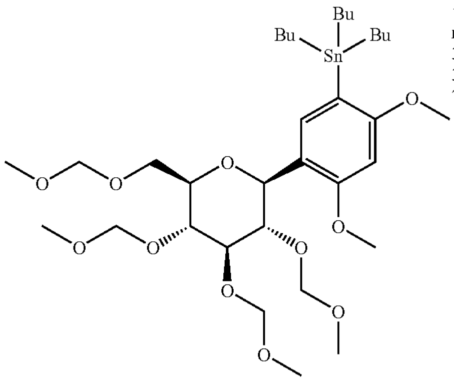 | $^1$H-NMR(CDCl$_3$): 0.87 (9H, t), 0.96–1.50 (18H, m), 2.82 (3H, s), 3.33 (3H, s), 3.45 (3H, s), 3.46 (3H, s), 3.57–3.92 (7H, m), 3.75 (3H, s), 3.83 (3H, s), 4.18–4.94 (8H, m), 6.36 (1H, s), 7.25 (1H, s) |
| 51 | 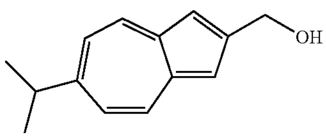 | $^1$H-NMR(CDCl$_3$): 1.34 (3H, s), 1.36 (3H, s), 1.76 (1H, t), 3.04–3.08 (1H, m), 5.09 (2H, d), 7.14 (2H, d), 8.23 (2H, d) |
| 52 | 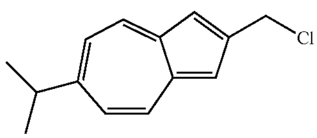 | $^1$H-NMR(CDCl$_3$): 1.33 (3H, s), 1.35 (3H, s), 3.04–3.07 (1H, m), 4.95 (2H, s), 7.14 (2H, d), 7.28 (2H, s), 8.23 (2H, d) |
| 53 | 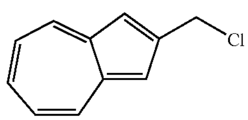 | $^1$H-NMR(CDCl$_3$): 4.98 (2H, s), 7.20 (2H, t), 7.37 (2H, s), 7.59 (1H, t), 8.30 (2H, d) |
| 54 | 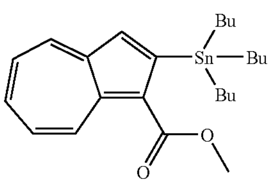 | $^1$H-NMR(CDCl$_3$): 0.87 (9H, t), 1.11–1.18 (6H, m), 1.27–1.38 (6H, m), 1.51–1.58 (6H, m), 3.96 (3H, s), 7.25 (1H, s), 7.42 (1H, t), 7.50 (1H, t), 7.74 (1H, t), 8.37 (1H, d), 9.58 (1H, d) |
| 55 | 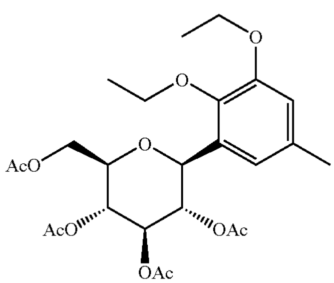 | $^1$H-NMR(CDCl$_3$): 1.38–1.46 (6H, m), 1.80 (3H, s), 2.01 (3H, s), 2.06 (3H, s), 2.07 (3H, s), 2.31 (3H, s), 3.83 (1H, ddd), 4.00–4.29 (6H, m), 4.55–4.65 (1H, m), 5.18–5.38 (3H, m), 6.64 (1H, s), 6.86 (1H, s) |
| 56 | 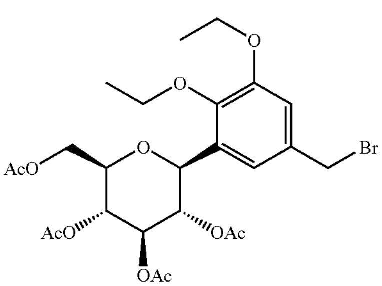 | $^1$H-NMR(CDCl$_3$): 1.41–1.48 (6H, m), 1.82 (3H, s), 2.02 (3H, s), 2.07 (3H, s), 2.17 (3H, s), 3.90 (1H, ddd), 4.02–4.30 (6H, m), 4.51 (1H, d), 4.62 (1H, d), 4.75–4.81 (1H, m), 5.20–5.42 (3H, m), 6.82 (1H, s), 6.90 (1H, s) |

TABLE 9

| Rf. | Structure | Data |
|---|---|---|
| 57 | 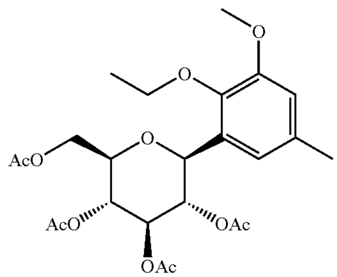 | ¹H-NMR(CDCl₃): 1.44 (3H, t), 1.81 (3H, s), 2.01 (3H, s), 2.04–2.08 (6H, m), 2.33 (3H, s), 3.78–4.28 (8H, m), 4.55–4.66 (1H, m), 5.17–5.38 (3H, m), 6.63 (1H, s), 6.85 (1H, s) |
| 58 | 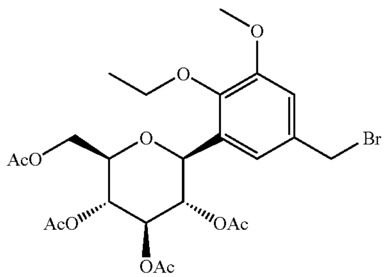 | ¹H-NMR(CDCl₃): 1.46 (3H, t), 1.82 (3H, s), 2.01 (3H, s), 2.07 (3H, s), 2.07 (3H, s), 3.88–4.30 (8H, m), 4.52 (1H, d), 4.63 (1H, d), 4.76–4.82 (1H, m), 5.21–5.41 (3H, m), 6.81 (1H, s), 6.90 (1H, s) |
| 59 | 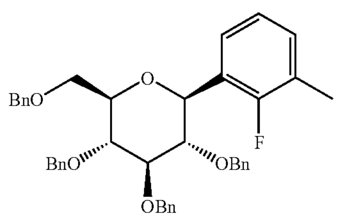 | ¹H-NMR(CDCl₃): 2.27 (3H, d), 3.56–3.66 (2H, m), 3.71–3.94 (5H, m), 4.44–4.68 (5H, m), 4.84–4.98 (3H, m), 6.87–7.37 (23H, m) |
| 60 | 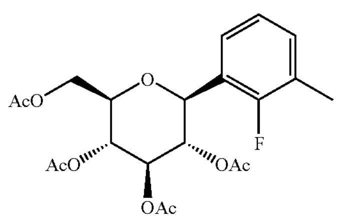 | FAB-MS(m/z): 441[M+H]⁺ |
| 61 | 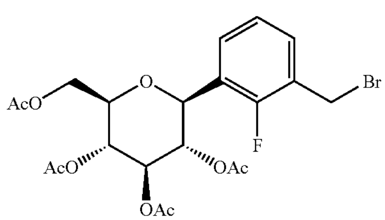 | EI-MS:519[M]⁺ |
| 62 | 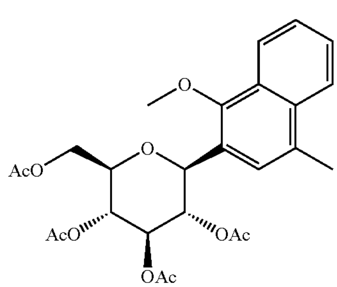 | FAB-MS(m/z): 503[M+H]⁺ |

TABLE 9-continued

| Rf. | Structure | Data |
|---|---|---|
| 63 | 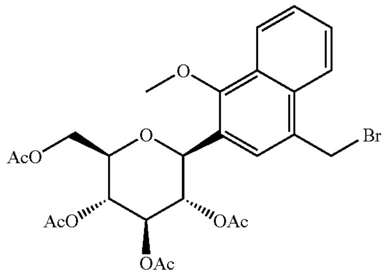 | EI-MS:581[M]+ |

TABLE 10

| Rf. | Structure | Data |
|---|---|---|
| 64 | 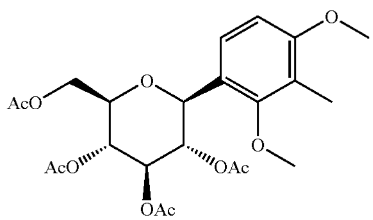 | FAB-MS(m/z): 483[M+H]+ |
| 65 | 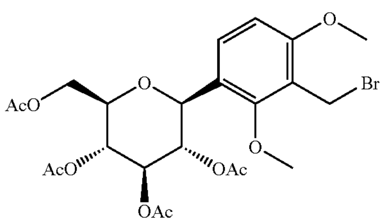 | FAB-MS(m/z): 562[M+H]+ |
| 66 | 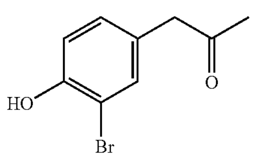 | FAB-MS(m/z): 230[M+H]+ |
| 67 | 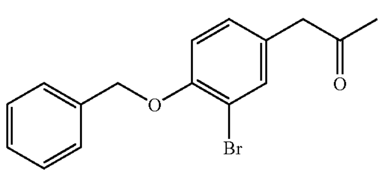 | $^1$H-NMR(CDCl$_3$): 2.16 (3H, s), 3.61 (2H, s), 5.14 (2H, s), 6.88–7.67 (2H, dd), 7.32–7.48 (6H, m) |
| 68 | 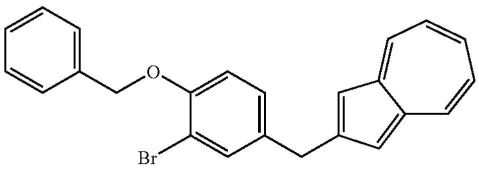 | FAB-MS(m/z): 404[M+H]+ |

TABLE 10-continued

| Rf. | Structure | Data |
|---|---|---|
| 69 | (structure) | $^1$H-NMR(CDCl$_3$): 3.70–4.98 (19H, m), 6.89 (2H, d), 3.44 (3H, s), 7.08–7.63 (31H, m), 8.11 (2H, d) |

TABLE 11

| Ex. | Structure | Data |
|---|---|---|
| 1 | (structure) | $^1$H-NMR(CDCl$_3$): 2.55 (3H, s), 3.47–3.81 (7H, m), 4.11–4.32 (2H, m), 4.40 (2H, s), 4.51–4.93 (6H, m),, 6.86–7.46 (28H, m), 7.49 (1H, s), 8.13 (2H, dd,) ESI-MS(m/z): 567[M+H]$^+$ |
| 2 | (structure) | $^1$H-NMR(CD$_3$OD): 2.57 (3H, s), 3.14–3.43 (5H, m), 3.66–3.70 (1H, m),3.96 (1H, d), 4.35 (2H, s), 4.41–4.94 (4H, m),, 6.99–7.21 (6H, m), 7.54 (1H, t), 7.60 (1H, s), 8.20 (1H, d), 8.34 (1H, d) EI-MS:393[M–H]$^-$ |
| 3 | (structure) | $^1$H-NMR(CDCl$_3$): 1.24–1.29 (9H, t), 2.92–3.01 (3H, q), 3.40–4.94 (17H, m), 6.85–8.08 (27H, m), 7.50 (1H, s), 8.17 (1H, d) ESI-MS(m/z): 811[M+H]$^+$ |
| 4 | (structure) | $^1$H-NMR(CD$_3$OD): 1.30 (6H, d), 1.32 (3H, t), 2.99–3.04 (3H, q), 3.47–3.67 (4H, m), 3.82–3.92 (2H, ABq), 4.15 (1H, d), 4.43 (2H, s), 6.95 (1H, t), 7.18–7.28 (3H, m), 7.20 (1H, s), 7.42 (1H, d), 7.56 (1H, d), 8.10 (1H, d), 8.15 (1H, s) EI-MS:450[M$^+$] |

TABLE 11-continued

| Ex. | Structure | Data |
|---|---|---|
| 5 | (structure: tetra-acetyl glucopyranose attached to ethoxyphenyl linked via CH2 to methyl azulene-1-carboxylate) | $^1$H-NMR(CDCl$_3$): 1.46 (3H, t), 1.75 (3H, s), 2.00 (3H, s), 2.03 (3H, s), 2.05 (3H, s), 3.84 (1H, m), 3.96 (3H, s), 4.03 (2H, q), 4.15 (1H, m), 4.28 (1H, m), 4.54 (2H, s), 4.92 (1H, m), 5.20 (1H, m), 5.35 (2H, m), 6.78 (1H, d), 6.89 (1H, s), 7.12 (1H, dd), 7.31 (1H, s), 7.38 (1H, t), 7.51 (1H, t), 7.70 (1H, t), 8.28 (1H, d), 9.52 (1H,d)<br>ESI-MS(m/z): 651[M+H]$^+$ |
| 6 | (structure: glucopyranose attached to ethoxyphenyl linked via CH2 to azulene-1-carboxylic acid) | $^1$H-NMR(CD$_3$OD): 1.40 (3H, t), 3.39 (2H, m), 3.49 (1H, m), 3.60 (1H, t), 3.65 (1H, m), 3.85 (1H, m), 4.05 (2H, m), 4.58 (2H, s), 4.69 (1H, d) 6.88 (1H, d), 7.012 (1H, s), 7.15 (1H, dd), 7.39 (1H, d), 7.43 (1H, t), 7.52 (1H, t), 7.75 (1H, t), 8.31 (1H, d), 9.50 (1H, d)<br>ESI-MS(m/z): 469[M+H]$^+$ |

TABLE 12

| Ex. | Structure | Data |
|---|---|---|
| 7 | (structure: glucopyranose attached to ethoxyphenyl linked via CH2 to azulene) | $^1$H-NMR(CD$_3$OD): 1.41 (3H, t), 2.13 (1H, brs), 2.54 (1H, brs), 2.79 (1H, brs), 2.97 (1H, brs), 3.55 (2H, m), 3.68 (2H, m), 3.81 (1H, m), 3.90 (1H, m), 4.02 (1H, dd), 4.10 (1H, dd), 4.30 (2H, s), 4.75 (1H, d), 6.84 (1H, d), 7.15 (5H, m), 7.39 (1H, d), 7.51 (1H, t), 7.52 (1H, t), 8.19 (2H, d)<br>ESI-MS(m/z): 425 [M+H]$^+$ |
| 8 | (structure: tetra-benzyl glucopyranose attached to methylphenyl linked via CH2 to methyl azulene-1-carboxylate) | $^1$H-NMR(CDCl$_3$): 2.39 (3H, s), 3.62 (2H, m), 3.74–3.84 (6H, m), 3.93 (3H, s), 4.33 (1H, d), 4.47–4.64 (5H, m), 4.84–4.95 (3H, m), 6.85 (1H, s), 6.91 (2H, d), 7.13–7.31 (21H, m), 7.45 (1H, s), 7.49 (1H, t), 7.67 (1H, m), 8.00 (1H, d), 9.51 (1H, d)<br>ESI-MS(m/z): 813[M+H]$^+$ |
| 9 | (structure: glucopyranose attached to methylphenyl linked via CH2 to methyl azulene-1-carboxylate) | $^1$H-NMR(CD$_3$OD): 2.33 (3H, s), 3.66–3.92 (6H, m), 4.45 (1H, d), 4.53 (2H, s), 6.94 (1H, s), 7.05 (2H, m), 7.34 (2H, m), 7.46 (1H, t), 7.66 (1H, t), 8.18 (1H, d), 9.38 (1H, d)<br>ESI-MS(m/z): 453[M+H]$^+$ |

TABLE 12-continued

| Ex. | Structure | Data |
| --- | --- | --- |
| 10 | 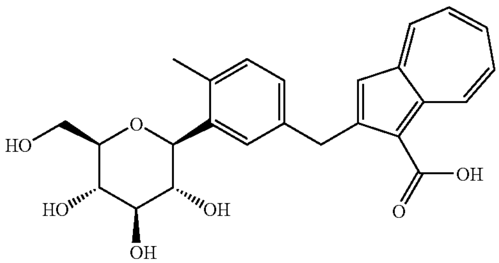 | $^1$H-NMR(CD$_3$OD): 2.32 (3H, s), 3.57–3.88 (3H, m), 4.35 (1H, d), 4.46 (2H, s), 6.88 (1H, s), 7.11 (2H, m), 7.27 (2H, m), 7.55 (1H, t), 7.68 (1H, t), 8.15 (1H, d), 9.33 (1H, d) ESI-MS(m/z): 438[M+H]$^+$ |
| 11 | 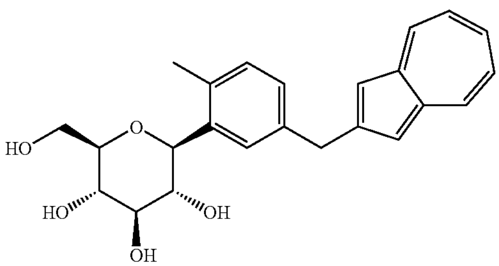 | $^1$H-NMR(CD$_3$OD): 2.39 (3H, s), 3.41 (2H, m), 3.54 (2H, m), 3.68 (1H, m), 3.87 (1H, d), 4.29 (2H, s), 4.45 (1H, d), 7.10 (6H, m), 7.41 (1H, s), 7.50 (1H, s), 8.17 (2H, d) ESI-MS(m/z): 395[M+H]$^+$ |
| 12 | 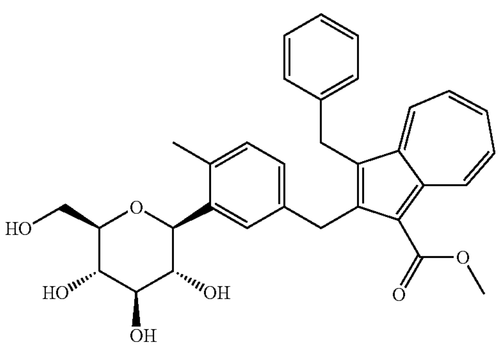 | $^1$H-NMR(CD$_3$OD): 2.28 (3H, s), 3.45 (2H, m), 3.64 (2H, m), 3.81 (3H, s), 3.82 (2H, m), 4.39 (3H, s), 4.55 (2H, d), 6.83 (1H, d), 6.94 (3H, d), 7.25 (4H, m), 7.33 (1H, t), 7.47 (1H, t), 7.68 (1H, t), 8.27 (1H, d), 9.38 (1H, d) ESI-MS(m/z): 543[M+H]$^+$ |

TABLE 13

| Ex. | Structure | Data |
| --- | --- | --- |
| 13 | 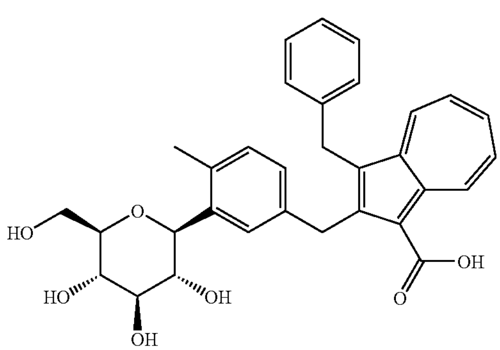 | $^1$H-NMR(CD$_3$OD): 2.78 (3H, s), 3.33 (2H, m), 3.62 (2H, m), 3.81 (2H, m), 4.40 (3H, s), 4.55 (2H, d), 6.79 (1H, d), 6.85 (3H, d), 7.11 (4H, m), 7.40 (1H, t), 7.47 (1H, t), 7.70 (1H, t), 8.22 (1H, d), 9.55 (1H, d) ESI-MS(m/z): 529[M+H]$^+$ |

TABLE 13-continued

| Ex. | Structure | Data |
|---|---|---|
| 14 | 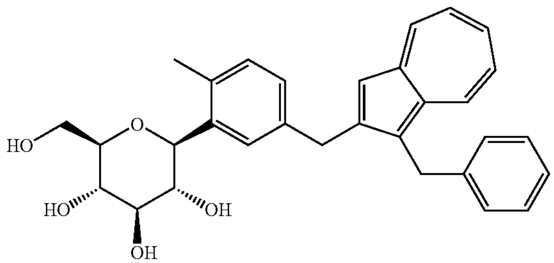 | $^1$H-NMR(CD$_3$OD): 2.37 (3H, s), 3.31 (2H, m), 3.50 (2H, m), 3.64 (1H, dd), 3.86 (1H, m), 4.13 (2H, s), 4.42 (3H, s), 6.90 (1H, dd), 7.02–7.21 (9H, m), 7.27 (1H, s), 7.48 (1H, t), 8.12 (1H, d), 8.22 (1H, d)<br>ESI-MS(m/z): 485[M+H]$^+$ |
| 15 | 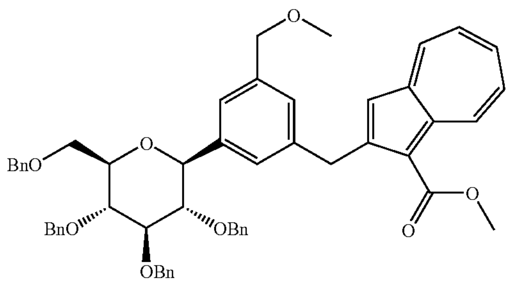 | $^1$H-NMR(CDCl$_3$): 2.32 (3H, s), 3.57–3.88 (3H, m), 4.35 (1H, d), 4.46 (2H, s), 6.88 (1H, s), 7.11 (2H, m), 7.27 (2H, m), 7.55 (1H, t), 7.68 (1H, t), 8.15 (1H, d), 9.33 (1H, d)<br>ESI-MS(m/z): 438[M+H]$^+$ |
| 16 | 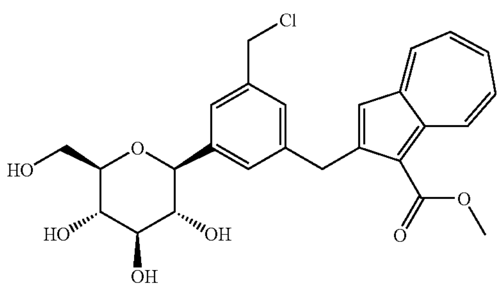 | $^1$H-NMR(CD$_3$OD): 2.39 (4H, brs), 3.38 (1H, m), 3.47 (1H, m), 3.60–3.80 (4H, m), 3.84 (3H, s), 4.10 (1H, d), 4.35 (2H, s), 4.53 (2H, s), 6.92 (1H, s), 7.16 (1H, s), 7.21 (1H, s), 7.25 (1H, m), 7.30 (1H, t), 7.44 (1H, t), 7.64 (1H, t), 8.17 (1H, d), 9.39 (1H, d)<br>ESI-MS(m/z): 532[M+H]$^+$ |
| 17 | 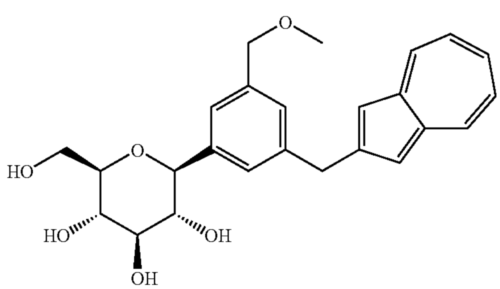 | $^1$H-NMR(CD$_3$OD): 2.40 (2H, brs), 3.14 (3H, s), 3.22 (1H, m), 3.45–3.67 (5H, m), 4.02 (1H, d), 4.18 (2H, s), 4.21 (2H, s), 4.97 (1H, brs), 5.21 (1H, brs), 6.99–7.06 (5H, m), 7.20 (1H, s), 7.40 (1H, t), 7.30 (1H, t), 8.05 (2H, d)<br>ESI-MS(m/z): 425[M+H]$^+$ |
| 18 | 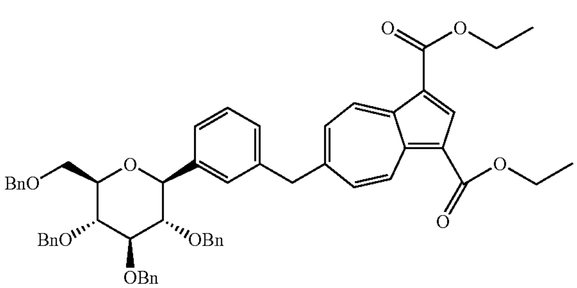 | $^1$H-NMR(CDCl$_3$): 1.43 (6H, t), 3.46–3.80 (7H, m), 4.20–4.93 (14H, m), 6.85–7.39 (24H, m), 7.62 (2H, d), 8.77 (1H, s), 9.64 (2H, d)<br>ESI-MS(m/z): 885[M+H]$^+$ |

TABLE 14

| Ex. | Structure | Data |
|---|---|---|
| 19 | 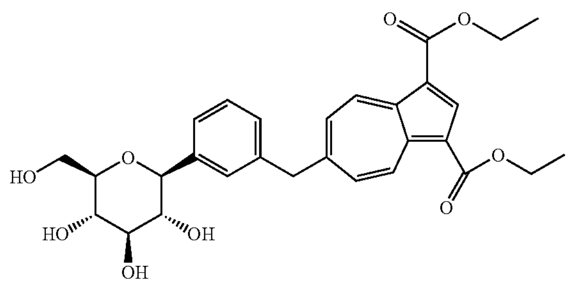 | ¹H-NMR(CD₃OD): 1.36 (6H, t), 3.39–4.12 (7H, m), 4.13 (2H, s), 4.36 (4H, dd), 7.03–7.28 (4H, m), 7.54 (2H, d), 8.66 (1H, s), 9.51 (2H, d)<br>ESI-MS(m/z): 523[M − H]⁻ |
| 20 | 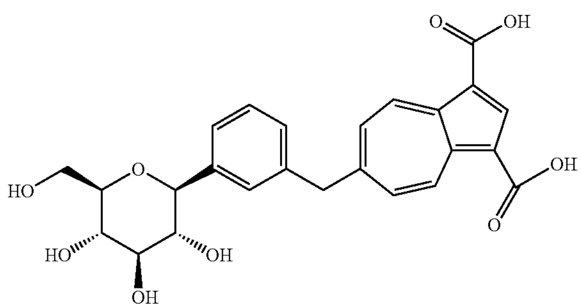 | ¹H-NMR(CD₃OD): 3.34–3.52 (4H, m), 3.71–3.93 (2H, m), 4.16 (1H, d), 4.40 (2H, s), 7.29–7.45 (4H, m), 7.88 (2H, d), 8.76 (1H, s)<br>ESI-MS(m/z): 467[M − H]⁻ |
| 21 | 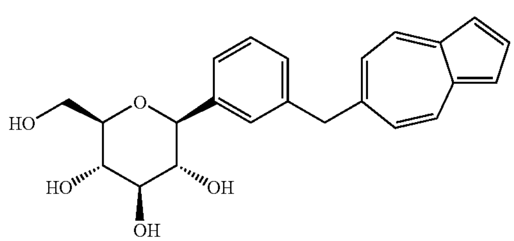 | ¹H-NMR(CD₃OD): 3.34–3.89 (6H, m), 4.12 (1H, d), 4.17 (2H, s), 7.18 (2H, d), 7.19–7.38 (6H, m), 7.77 (1H, t), 8.25 (2H, d)<br>ESI-MS(m/z): 381[M + H]⁺ |
| 22 | 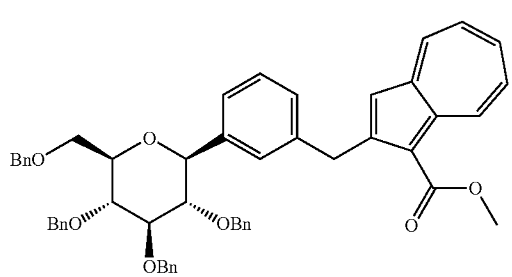 | ¹H-NMR(CDCl₃): 3.52–3.82 (7H, m), 3.93 (3H, s), 4.22–4.95 (10H, m), 6.86–7.68 (28H, m), 8.04 (1H, d), 9.53 (1H, d)<br>ESI-MS(m/z): 799[M + H]⁺ |
| 23 | 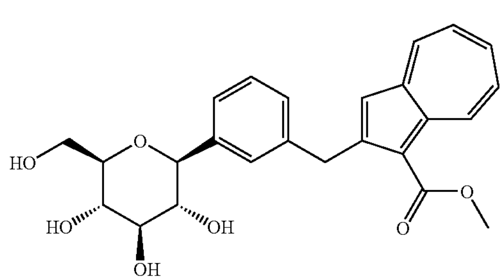 | ¹H-NMR(CD₃OD): 3.42–3.93 (6H, m), 3.93 (3H, s), 4.18 (1H, d), 4.63 (2H, s), 7.02 (1H, s), 7.02–7.33 (4H, m), 7.42 (1H, t), 7.53 (1H, t), 7.73 (1H, t), 8.30 (1H, d), 9.48 (1H, d)<br>ESI-MS(m/z): 423[M − H]⁻ |

TABLE 14-continued

| Ex. | Structure | Data |
|---|---|---|
| 24 | 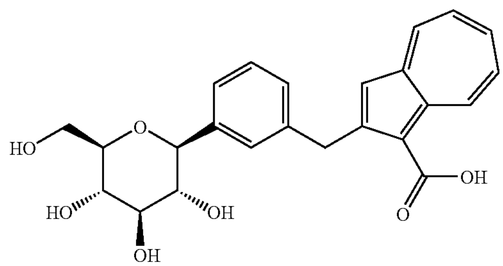 | $^1$H-NMR(CD$_3$OD): 3.34–3.52 (4H, m), 3.70–3.93 (2H, m), 4.15 (1H, d), 4.69 (2H, s), 7.06 (1H, s), 7.24–7.84 (7H, m), 8.38 (1H, d), 9.57 (1H, d)<br>ESI-MS(m/z): 437[M − H]$^-$ |
| 25 | 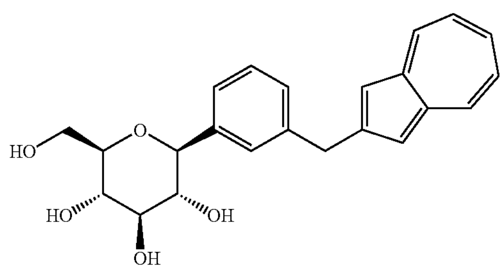 | $^1$H-NMR(CD$_3$OD): 3.34–3.93 (6H, m), 4.16 (1H, d, J=9.3 Hz), 4.37 (2H, s), 7.15–7.58 (9H, m), 8.24 (2H, d)<br>ESI-MS(m/z): 381[M + H]$^+$ |

TABLE 15

| Ex. | Structure | Data |
|---|---|---|
| 26 | 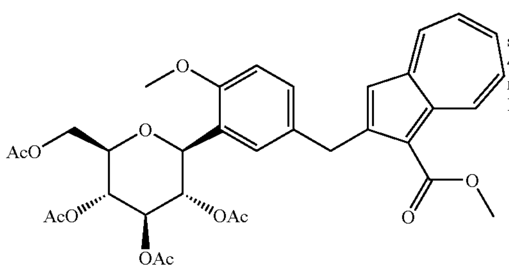 | $^1$H-NMR(CDCl$_3$): 1.74–2.09 (12H, m), 3.82 (3H, s), 3.96 (3H, s), 4.11–4.27 (2H, m), 4.55 (2H, s), 4.91–5.36 (5H, m), 6.79–7.69 (7H, m), 4.92 (1H, m), 8.29 (1H, d), 9.53 (1H, d)<br>ESI-MS(m/z): 637[M+H]$^+$ |
| 27 | 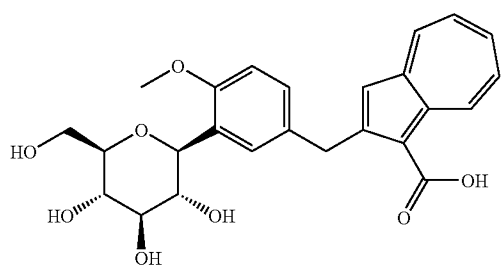 | $^1$H-NMR(CD$_3$OD): 3.29–3.66 (5H, m), 3.78 (3H, s), 3.84 (1H, m), 4.55 (2H, s), 4.70 (1H, d), 6.88 (1H, d), 6.98 (1H, s), 7.15 (1H, dd), 7.37–7.42 (1H, m), 7.49 (1H, t), 7.72 (1H, t), 8.28 (1H, d), 9.48 (1H, d)<br>ESI-MS(m/z): 435[M−H]$^-$ |
| 28 | 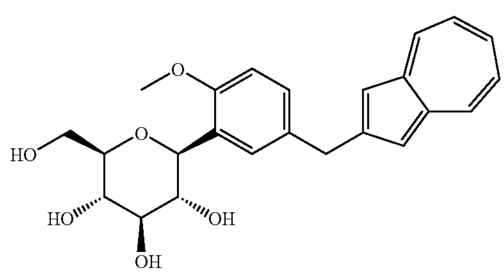 | $^1$H-NMR(CD$_3$OD): 3.36–3.90 (6H, m), 3.86 (3H, s), 4.31 (2H, s), 4.74 (1H, d), 6.97 (1H, d), 7.15–7.43 (6H, m), 7.54 (1H, t), 8.23 (2H, d)<br>ESI-MS(m/z): 411[M+H]$^+$ |

TABLE 15-continued

| Ex. | Structure | Data |
|---|---|---|
| 29 | 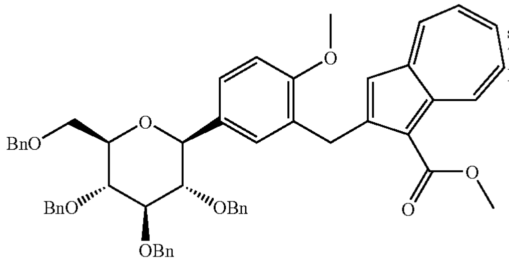 | $^1$H-NMR(CDCl$_3$): 3.49–3.89 (7H, m), 3.94 (3H, s), 4.09–4.95 (10H, m), 6.74–7.68 (24H, m), 7.94 (1H, d), 9.52 (1H, d)<br>ESI-MS(m/z): 851[M+Na]$^+$ |
| 30 | 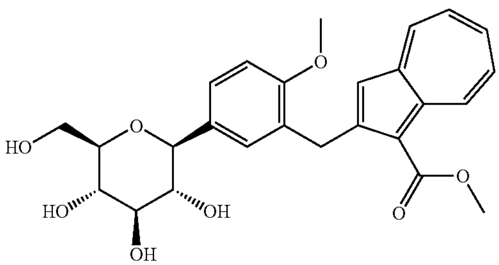 | $^1$H-NMR(CD$_3$OD): 3.29–4.56 (15H, m), 6.79–7.18 (4H, m), 7.41 (1H, t), 7.52 (1H, t), 7.74 (1H, t), 8.28 (1H, d), 9.42 (1H, d)<br>ESI-MS(m/z): 469[M+H]$^+$ |
| 31 | 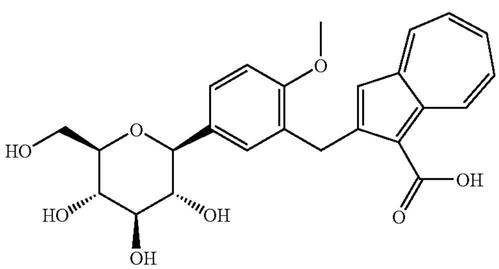 | $^1$H-NMR(CD$_3$OD): 3.30–4.50 (7H, m), 3.80 (3H, s), 4.28 (2H, s), 6.92–7.31 (6H, m), 7.48 (1H, t), 8.16 (2H, d)<br>ESI-MS(m/z): 477[M+Na]$^+$ |
| 32 | 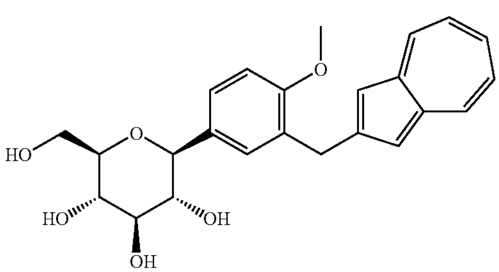 | $^1$H-NMR(CD$_3$OD): 3.30–4.29 (7H, m), 3.83 (3H, s), 4.30 (2H, s), 6.94–7.29 (6H, m), 7.46 (1H, t), 8.16 (2H, d)<br>ESI-MS(m/z): 411[M+H]$^+$ |

TABLE 16

| Ex. | Structure | Data |
|---|---|---|
| 33 | 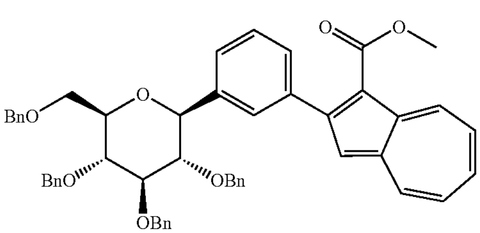 | $^1$H-NMR(CDCl$_3$): 3.57–3.89 (7H, m), 3.69 (3H, s), 4.35 (1H, d), 4.45 (1H, d), 4.56–5.00 (6H, m), 6.95–7.76 (28H, m), 8.36 (1H, d)<br>ESI-MS(m/z): 802[M+NH$_4$]$^+$ |

TABLE 16-continued

| Ex. | Structure | Data |
|---|---|---|
| 34 | 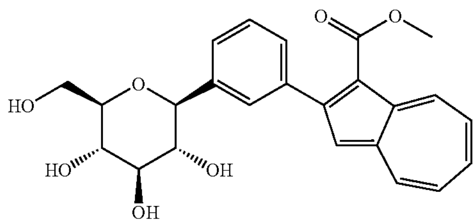 | ¹H-NMR(CD₃OD): 3.44–3.76 (5H, m), 3.77 (3H, s), 3.89–3.92 (1H, m), 4.23 (1H, d), 7.37–7.88 (8H, m), 8.47 (1H, d), 9.29 (1H, d)<br>ESI-MS(m/z): 442[M+NH₄]⁺ |
| 35 | 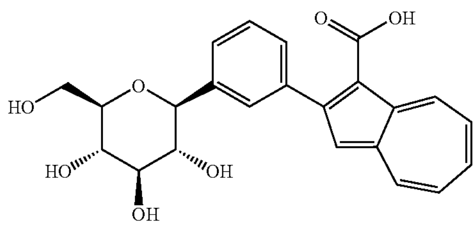 | ¹H-NMR(CD₃OD): 3.52–3.86 (5H, m), 3.89–4.11 (1H, m), 4.17 (1H, d), 7.33–7.88 (8H, m), 8.52 (1H, d), 9.25 (1H, d)<br>ESI-MS(m/z): 409[M–H]⁻ |
| 36 | 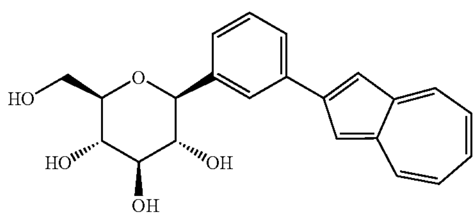 | ¹H-NMR(CD₃OD): 3.49–3.73 (2H, m), 4.14 (1H, d), 4.50 (1H, t), 4.88 (1H, d), 4.98 (2H, t), 7.23 (2H, t), 7.36 (1H, d), 7.44 (1H, t), 7.61 (1H, t), 7.82 (2H, s), 7.96 (1H, d), 8.00 (1H, s),8.38 (2H,d)<br>ESI-MS(m/z): 367[M+H]⁺ |
| 37 | 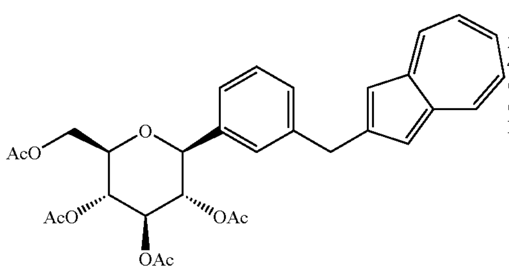 | ¹H-NMR(CDCl₃): 1.63 (3H, s), 1.98(3H, s), 2.05 (3H, s), 2.06 (3H, s), 3.80–4.38 (4H, m), 4.17 (2H, s), 5.12 (1H, t), 5.22 (1H, t), 5.31 (1H, t), 7.11–7.32 (8H, m), 7.51 (1H, t), 8.20 (2H, d)<br>ESI-MS(m/z): 549[M+H]⁺ |
| 38 | 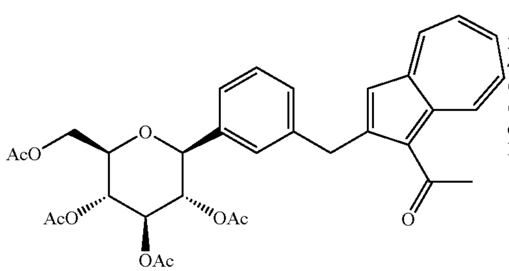 | ¹H-NMR(CDCl₃): 1.71 (3H, s), 2.07 (3H, s), 2.08 (3H, s), 2.09 (3H, s), 2.70 (3H, s), 3.80–4.38 (4H, m), 4.57 (2H, s), 5.11 (1H, t), 5.22 (1H, t), 5.30 (1H, t), 6.84 (1H, s), 7.17–7.55 (6H, m), 7.72 (1H, t), 8.28 (1H, d), 9.35 (1H, d)<br>ESI-MS(m/z): 589[M–H]⁻ |
| 39 | 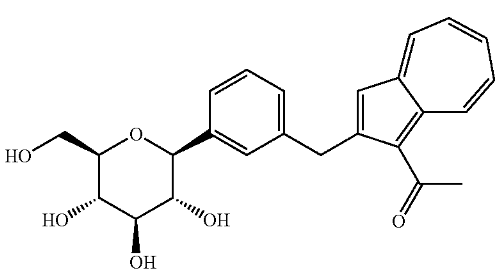 | ¹H-NMR(CD₃OD): 2.69 (3H, s), 3.30–3.87 (6H, m), 4.10 (1H, d), 7.03 (1H, s), 7.12–7.46 (4H, m), 7.49 (1H, t), 7.57 (1H, t), 7.79 (1H, t), 8.37 (1H, d), 9.30 (1H, d)<br>ESI-MS(m/z): 423[M+H]⁺ |

TABLE 17

| Ex | Structure | Data |
|---|---|---|
| 40 | 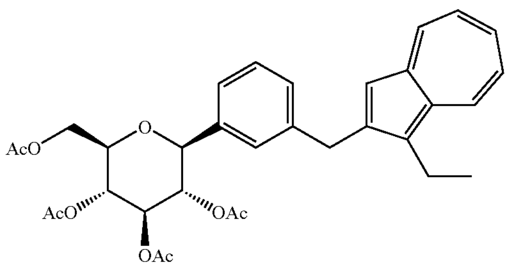 | ¹H-NMR(CDCl₃): 1.81 (3H, t), 1.67 (3H, s), 1.98 (3H, s), 2.05 (3H, s), 2.08 (3H, s), 3.04 (2H, dd), 3.60–4.36 (6H, m), 5.08–5.31 (3H, m), 6.99–7.51 (8H, m), 8.09 (1H, d), 8.20 (1H, d)<br>ESI-MS(m/z): 577[M+H]⁺ |
| 41 | 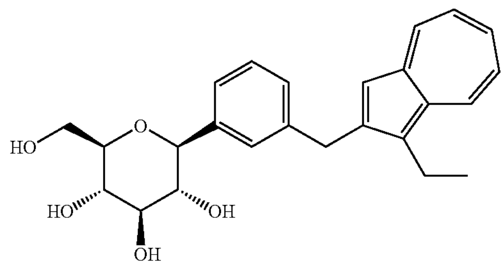 | ¹H-NMR(CD₃OD): 1.20 (3H, t), 3.07 (2H, dd), 3.30–3.88 (6H, m), 4.10 (1H, d), 4.31 (2H, s), 7.00–7.45 (8H, m), 8.08 (1H, d), 8.22 (1H, d)<br>ESI-MS(m/z): 409[M+H]⁺ |
| 42 | 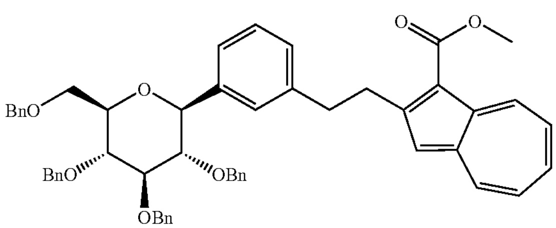 | ¹H-NMR(CDCl₃): 3.08–3.12 (2H, m), 3.50–3.82 (9H, m), 3.95 (3H, s), 4.13–4.97 (8H, m), 6.88–7.39 (26H, m), 7.50 (1H, t), 7.66 (1H, t), 8.23 (1H, d), 9.53 (1H, d)<br>ESI-MS(m/z): 830[M+NH₄]⁺ |
| 43 | 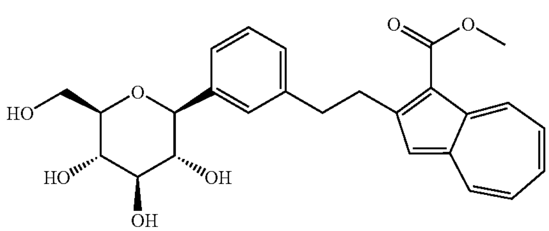 | ¹H-NMR(CD₃OD): 3.04 (2H, t), 3.30–3.89 (8H, m), 3.89 (3H, s), 4.11 (1H, d), 7.17–7.31 (5H, m), 7.48 (1H, t), 7.55 (1H, t), 7.78 (1H, t), 8.40 (1H, d), 9.44 (1H, d)<br>ESI-MS(m/z): 453[M+H]⁺ |
| 44 | 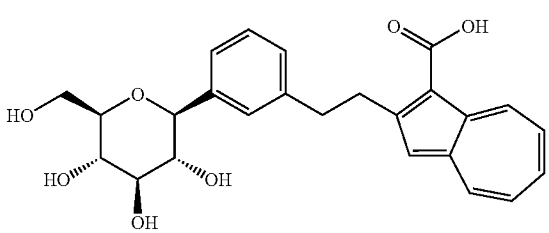 | ¹H-NMR(CD₃OD): 3.06–3.10 (2H, m), 3.30–3.89 (8H, m), 4.12 (1H, d), 7.18–7.34 (5H, m), 7.46 (1H, t), 7.53 (1H, t), 7.76 (1H, t), 8.39 (1H, d), 9.50 (1H, d)<br>ESI-MS(m/z): 439[M+H]⁺ |
| 45 | 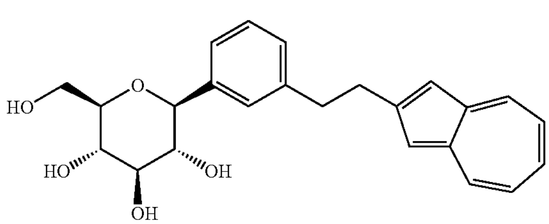 | ¹H-NMR(CD₃OD): 3.11 (2H, t), 3.27–3.89 (8H, m), 4.11 (1H, d), 7.11–7.24 (7H, m), 7.33 (1H, s), 7.50 (1H, t), 8.20 (2H, d)<br>ESI-MS(m/z): 395[M+H]⁺ |

TABLE 17-continued

| Ex | Structure | Data |
|---|---|---|
| 46 | 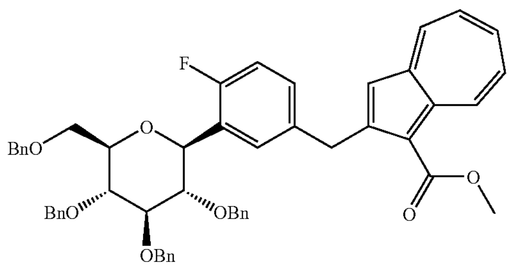 | ¹H-NMR(CDCl₃): 3.60–3.99 (7H, m), 3.91 (3H, s), 4.43–4.93 (10H, m), 6.85–7.44 (25H, m), 7.50 (1H, t), 7.68 (1H, t), 8.05 (1H, d), 9.51 (1H, d)<br>ESI-MS(m/z): 834[M+NH₄]⁺ |

TABLE 18

| Ex. | Structure | Data |
|---|---|---|
| 47 | 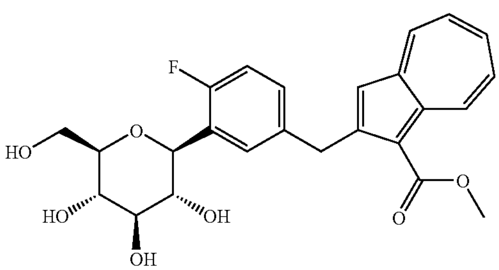 | ¹H-NMR(CD₃OD): 3.38–3.88 (6H, m), 3.93 (3H, s), 4.48–4.51 (1H, m), 4.57 (2H, s), 6.97 (1H, dd), 7.06 (1H, s), 7.14–7.18 (1H, m), 7.44–7.51 (2H, m), 7.56 (1H, t), 7.80 (1H, m), 8.38 (1H, d), 9.46 (1H, d)<br>ESI-MS(m/z): 457[M+H]⁺ |
| 48 | 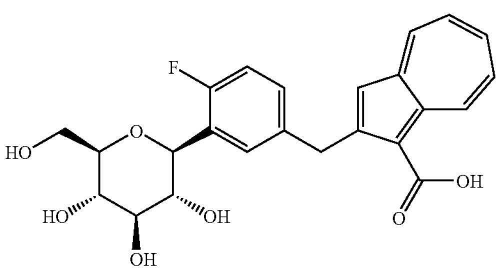 | ¹H-NMR(CD₃OD): 3.38–3.87 (6H, m), 4.49–4.50 (1H, m), 4.61 (2H, s), 6.96–7.56 (6H, m), 7.77 (1H, t), 8.34 (1H, d), 9.52 (1H, d)<br>ESI-MS(m/z): 441[M–H]⁻ |
| 49 | 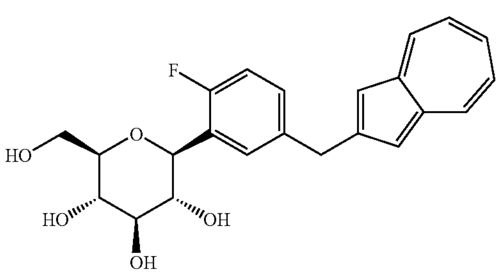 | ¹H-NMR(CD₃OD): 3.34–3.88 (6H, m), 4.31 (2H, s), 4.49–4.83 (1H, m), 6.97–7.54 (8H, m), 8.20 (2H, d)<br>ESI-MS(m/z): 399[M+H]⁺ |
| 50 | 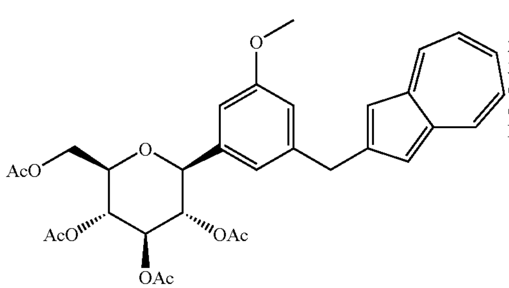 | ¹H-NMR(CDCl₃): 1.63 (3H, s), 1.98 (3H, s), 2.04 (3H, s), 2.06 (3H, s), 3.78 (3H, s), 3.79–3.86 (1H, m), 4.09–5.31 (6H, m), 6.80–6.81 (3H, m), 7.11–7.16 (4H, m), 7.51 (1H, t), 8.20 (2H, d)<br>ESI-MS(m/z:579[M+H]⁺ |

TABLE 18-continued
| Ex. | Structure | Data |
|---|---|---|
| 51 | 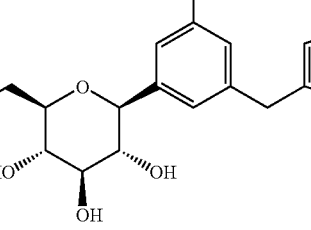 | ¹H-NMR(CD₃OD): 3.30–3.45 (4H, m), 3.69 (1H, dd), 3.75 (3H, s), 3.85–3.89 (1H, m), 4.08 (1H, d), 4.29 (2H, s), 6.78 (1H, t), 6.85 (1H, t), 6.97 (1H, t), 7.11–7.16 (4H, m), 7.50 (1H, t), 8.19 (2H, d)<br>ESI-MS(m/z): 433[M+Na]⁺ |
| 52 | 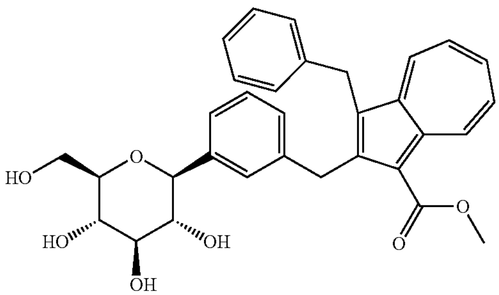 | ¹H-NMR(CD₃OD): 3.42–3.93 (6H, m), 3.93 (3H, s), 4.18 (1H, d), 4.33 (2H, s), 4.63 (2H, s), 7.02 (1H, s), 7.02–7.33 (8H, m), 7.42 (1H, t), 7.53 (1H, t), 7.73 (1H, t), 8.30 (1H, d), 9.48 (1H, d)<br>ESI-MS(m/z): 527[M–H]⁻ |
| 53 | 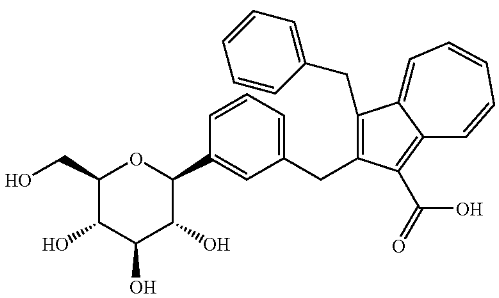 | ¹H-NMR(CD₃OD): 3.31–3.87 (6H, m), 4.05 (1H, d), 4.17 (2H, s), 4.42 (2H, s), 6.92–7.19 (9H, m), 7.40 (1H, t), 7.51 (1H, t), 7.73 (1H, t), 8.40(1H, d), 9.51(1H, d)<br>ESI-MS(m/z): 513[M–H]⁻ |
TABLE 19
| Ex. | Structure | Data |
|---|---|---|
| 54 | 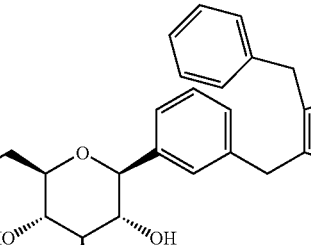 | ¹H-NMR(CD₃OD): 3.31–3.88 (6H, m), 4.06 (1H, d), 4.17 (2H, s), 4.42 (2H, s), 7.02–7.26 (12H, m), 7.48 (1H, t), 8.14 (1H, d), 8.24 (1H, d)<br>ESI-MS(m/z): 471[M+H]⁺ |
| 55 | 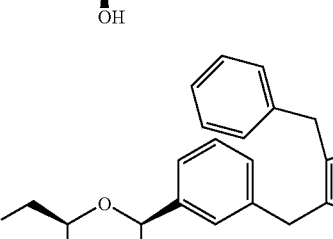 | ¹H-NMR(CDCL₃): 1.32 (3H, s), 1.33 (3H, s), 1.63 (3H, s), 1.98 (3H, s), 2.05 (3H, s), 2.06 (3H, s), 3.01–3.05 (1H, m), 3.79–3.83 (1H, m), 4.14–4.37 (5H, m), 5.11 (1H, t), 5.22 (1H, t), 5.29 (1H, t), 7.05 (2H, s), 7.08 (2H, d), 7.20–7.31 (4H, m), 8.13 (2H, d)<br>ESI-MS(m/z): 591[M+H]⁺ |

TABLE 19-continued

| Ex. | Structure | Data |
|---|---|---|
| 56 | 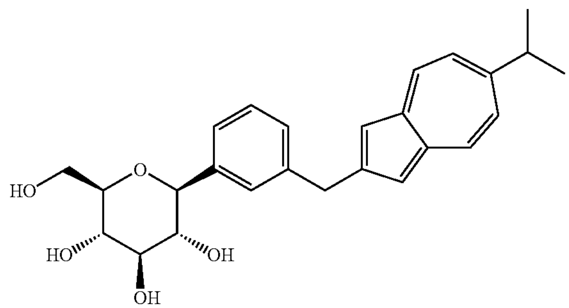 | ¹H-NMR(CD₃OD): 1.32 (3H, s), 1.34 (3H, s), 3.02–3.05 (1H, m), 3.37–3.88 (6H, m), 4.11 (1H, d), 4.29 (2H, s), 7.06 (2H, s), 7.10 (2H, d), 7.21–7.27 (3H, m), 7.36 (1H, s), 8.12 (2H, d)<br>ESI-MS(m/z): 423[M+H]⁺ |
| 57 | 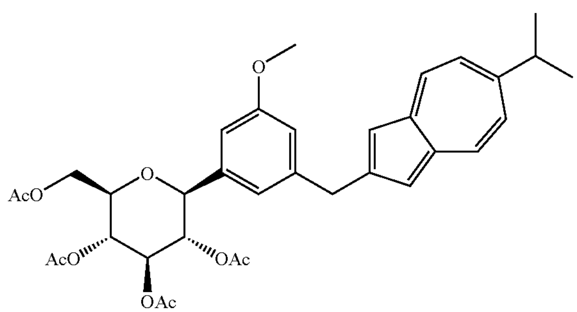 | ¹H-NMR(CDCl₃): 1.32 (3H, s), 1.33 (3H, s), 1.64 (3H, s), 1.98 (3H, s), 2.05 (3H, s), 2.06 (3H, s), 3.01–3.05 (1H, m), 3.77 (3H, s), 3.78–3.81 (1H, m), 4.11–4.34 (3H, m), 4.26 (2H, s), 5.11 (1H, t), 5.22 (1H, t), 5.28 (1H, t), 6.78 (3H, m), 7.04 (2H, s), 7.06 (2H, d)<br>ESI-MS(m/z): 621[M+H]⁺ |
| 58 | 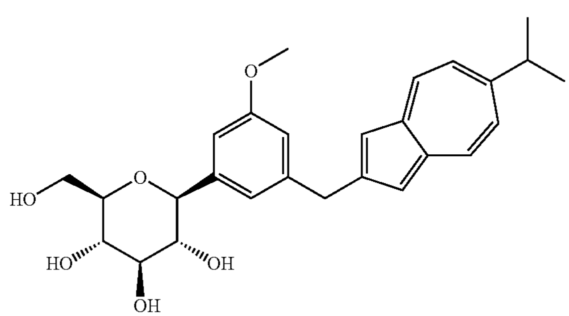 | ¹H-NMR(CD₃OD): 1.32 (3H, s), 1.34 (3H, s), 3.02–3.05 (1H, m), 3.36–3.43 (4H, m), 3.67 (1H, dd), 3.75 (3H, s), 3.78 (1H, d), 3.85 (1H, dd), 4.08 (1H, d), 4.25 (2H, s), 6.77 (1H, d), 6.85 (1H, d), 6.96 (1H, s), 7.06 (2H, s), 7.11 (2H, d), 8.12 (2H, d)<br>ESI-MS(m/z): 453[M+H]⁺ |
| 59 | 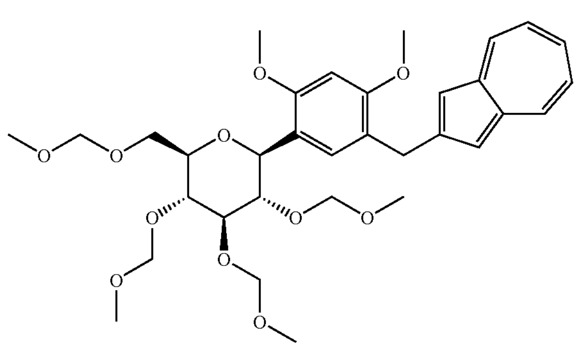 | ¹H-NMR(CDCl₃): 2.81 (3H, s), 3.24 (3H, s), 3.431 (3H, s), 3.435 (3H, s), 3.53–3.88 (6H, m), 4.18–4.91 (8H, m), 4.26 (1H, d), 6.44 (1H, s), 7.10 (2H, t), 7.15 (2H, s), 7.23 (1H, brs), 7.47 (1H, t), 8.14 (2H, d)<br>EI-MS: 616[M⁺] |

TABLE 20

| Ex. | Structure | Data |
|---|---|---|
| 60 | 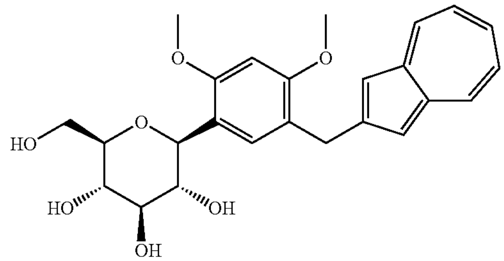 | $^1$H-NMR(CD$_3$OD): 2.03 (1H, t), 2.12 (1H, brs), 2.60 (1H, brs), 2.77 (3H, brs), 3.45–3.80 (6H, m), 3.85 (3H, s), 3.87 (3H, s), 4.23–4.33 (2H, ABq), 4.69 (1H, d), 6.52 (1H, s), 7.12 (2H, t), 7.15 (2H, s), 7.21 (1H, s), 7.49 (1H, t), 8.17 (2H, d)<br>EI-MS:440[M$^+$] |
| 61 | 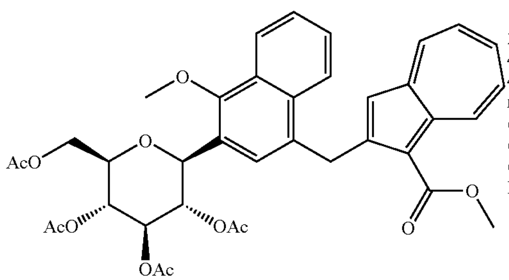 | $^1$H-NMR(CDCl$_3$): 1.75 (3H, s), 2.00 (3H, s), 2.03 (3H, s), 2.08 (3H, s), 3.95 (1H, m), 4.04 (3H, s), 4.05 (3H, s), 4.16 (1H, dd), 4.28 (1H, dd), 4.90 (1H, d), 5.08–5.18 (2H, m), 5.26 (1H, t), 5.40–5.54 (2H, m), 6.60 (1H, s), 7.30 (1H, t), 7.38 (1H, t), 7.46–7.55 (3H, m), 7.67 (1H, m), 7.88 (1H, d), 8.09 (1H, d), 8.15 (1H, d), 9.56 (1H, d)<br>ESI-MS(m/z): 423[M+H]$^+$ |
| 62 | 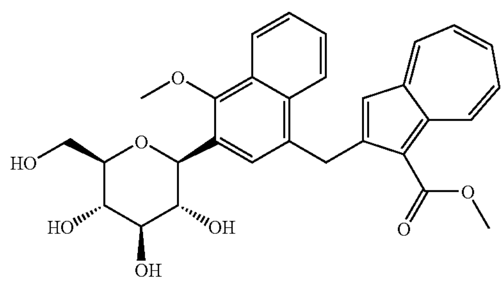 | $^1$H-NMR(CDCl$_3$): 3.85 (3H, s), 3.96 (3H, s), 4.83 (1H, d), 4.96 (2H, s), 6.63 (1H, s), 7.23 (1H, t), 7.34–7.40 (2H, m), 7.43–7.50 (2H, m), 7.62 (1H, t), 7.83 (1H, d), 8.02 (1H, d), 8.12 (1H, d), 9.45 (1H, d)<br>ESI-MS(m/z): 453[M+H]$^+$ |
| 63 | 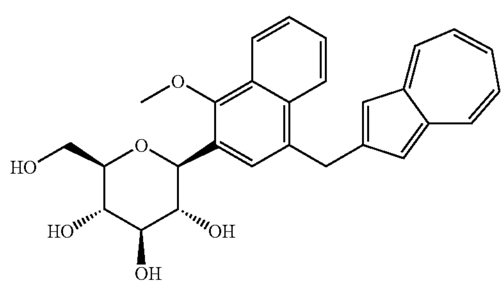 | $^1$H-NMR(CD$_3$OD): 3.41–3.52 (2H, m), 3.57 (1H, t), 3.65–3.76 (2H, m), 3.89 (1H, dd), 4.00–4.03 (4H, m), 7.07–7.14 (4H, m), 7.40 (1H, m), 7.44–7.51 (2H, m), 7.59 (1H, s), 8.01 (1H, d), 8.10–8.18 (3H, m)<br>FAB-MS(m/z): 461[M+H]$^+$ |
| 64 | 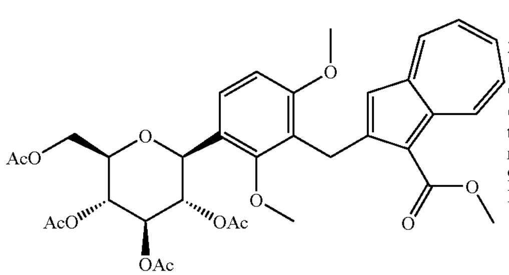 | $^1$H-NMR(CDCl$_3$): 1.78 (3H, s), 2.02 (3H, s), 2.04 (3H, s), 2.06 (3H, s), 3.64 (3H, s), 3.72 (3H, s), 3.80–3.92 (2H, s), 4.04 (3H, s), 4.12 (1H, dd), 4.26 (1H, dd), 4.64 (2H, s), 4.82 (1H, d), 5.24 (1H, t), 5.35 (1H, t), 5.48 (1H, t), 6.59 (1H, s), 6.80 (1H, d), 7.25–7.40 (3H, m), 7.50 (1H, t), 7.66 (1H, t), 8.11 (1H, d), 9.52(1H, d)<br>FAB-MS(m/z): 667[M+H]$^+$ |

TABLE 20-continued

| Ex. | Structure | Data |
|---|---|---|
| 65 | 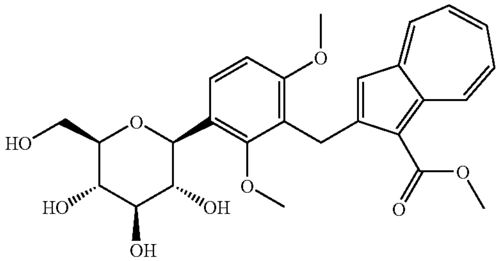 | ¹H-NMR(CDCl₃): 3.53 (3H, s), 3.56 (3H, s), 3.94 (3H, s), 4.52 (2H, s), 6.62 (1H, s), 6.72 (1H, d), 7.18 (1H, t), 7.35–7.46 (2H, m), 7.57 (1H, t), 8.00 (1H, d), 9.45 (1H, d)<br>FAB-MS(m/z): 499[M+H]⁺ |

TABLE 21

| Ex. | Structure | Data |
|---|---|---|
| 66 | 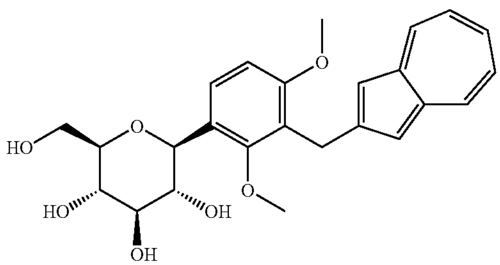 | ¹H-NMR(CD₃OD): 3.37–3.42 (2H, m), 3.44 (1H, m), 3.62 (1H, m), 3.65 (3H, s), 3.69 (1H, m), 3.80 (3H, s), 3.84 (1H, m), 4.37 (2H, s), 4.53 (1H, d), 6.88 (1H, d), 7.06–7.13 (4H, m), 7.37 (1H, d), 7.46 (1H, m), 8.12 (2H, d)<br>FAB-MS(m/z): 441[M +H]⁺ |
| 67 | 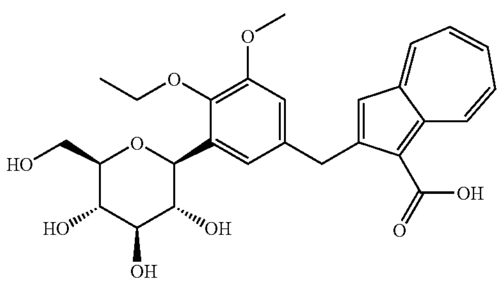 | ¹H-NMR(CD₃OD): 1.37 (3H, t), 2.98–3.10(1H, m), 3.30–3.70 (8H, m), 4.05 (1H, d), 4.10 (1H, d), 4.58 (1H, d), 6.74 (1H, s), 6.89 (1H, s), 7.10 (1H, s), 7.35 (1H, dd), 7.47 (1H, dd), 7.69 (1H, dd), 8.24 (1H, d), 9.46 (1H, d)<br>FAB-MS(m/z): 497[M –H]⁻ |
| 68 | 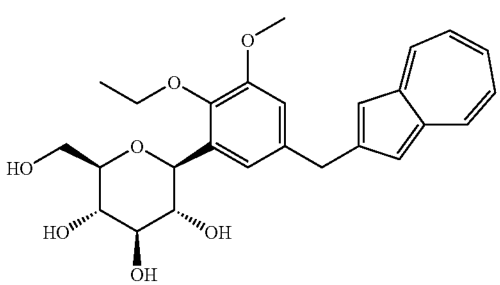 | ¹H-NMR(CD₃OD): 1.40 (3H, t), 3.07–3.16 (1H, m), 3.36–3.72 (5H, m), 3.74 (3H, s), 4.10 (2H, q), 4.30 (1H, d), 4.46 (1H, d), 4.59 (1H, d), 6.81 (1H, s), 7.09–7.18 (5H, m), 7.50 (1H, dd), 8.18 (2H, d)<br>FAB-MS(m/z): 455 [M +H]⁺ |
| 69 | 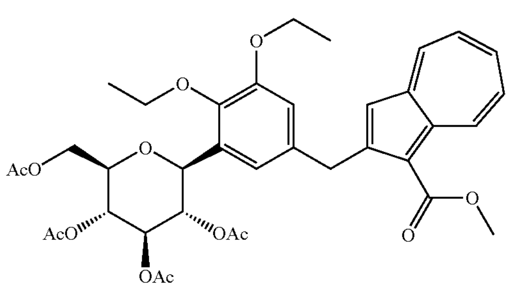 | ¹H-NMR(CDCl₃): 1.39 (3H, t), 1.48 (3H, t), 1.78 (3H, s), 1.96–2.00 (9H, m), 3.42–4.33 (11H, m), 4.51–5.45 (5H, m), 6.73 (1H, s), 6.76 (1H, s), 7.00 (1H, s), 7.37 (1H, t), 7.55 (1H, t), 7.72 (1H, t), 8.12 (1H, d), 9.54 (1H, d)<br>FAB-MS(m/z): 695[M +H]⁺ |

TABLE 21-continued

| Ex. | Structure | Data |
|---|---|---|
| 70 | 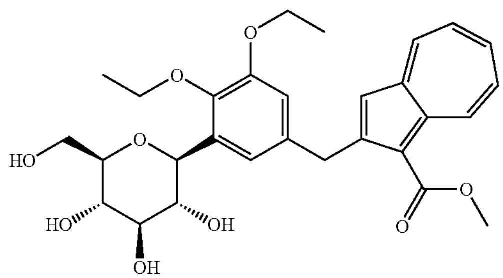 | ¹H-NMR(CD₃OD): 1.21 (3H, t), 1.31 (3H, t), 3.18–3.23 (1H, m), 3.32–3.63 (6H, m), 3.78–3.94 (5H, m), 4.02 (2H, q), 4.25 (1H, d), 4.44 (1H, d), 6.61 (1H, s), 6.84 (1H, s), 7.04 (1H, s), 7.33 (1H, t), 7.44 (1H, t), 7.66 (1H, t), 8.19 (1H, d), 9.35 (1H, d)<br>FAB-MS(m/z): 527[M +H]⁺ |
| 71 | 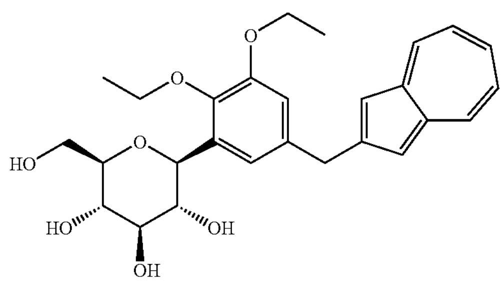 | ¹H-NMR(CD₃OD): 1.23 (3H, t), 1.30 (3H, t), 2.98–3.06 (1H, m), 3.25–3.64 (5H, m), 3.87 (2H, q), 4.00 (2H, q), 4.19 (1H, d), 4.36 (1H, d), 4.48 (1H, d), 6.93 (1H, s), 6.98–7.07 (5H, m), 7.40 (1H, t), 8.08 (1H, d)<br>FAB-MS(m/z): 469[M +H]⁺ |
| 72 | 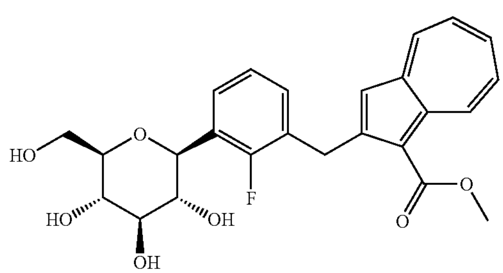 | ¹H-NMR(CD₃OD): 3.19–3.50 (4H, m), 3.60 (1H, dd), 3.75–3.85(4H, m), 4.45–4.55 (3H, m), 6.83–7.04 (3H, m), 7.26–7.52 (3H, m), 7.60–7.74 (1H, m), 8.14–8.28 (1H, m), 9.29–9.41 (1H, m)<br>FAB-MS(m/z): 457[M +H]⁺ |

TABLE 22

| Ex. | Structure | Data |
|---|---|---|
| 73 | 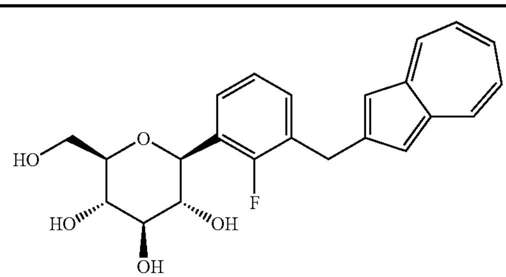 | ¹H-NMR(CD₃OD): 3.28–3.62 (5H, m), 3.77 (1H, dd), 4.24 (2H, s), 4.47 (1H, d), 6.96–7.17 (6H, m), 7.25–7.34 (1H, m), 7.40 (1H, d), 8.08 (2H, d)<br>FAB-MS(m/z): 399 [M +H]⁺ |
| 74 | 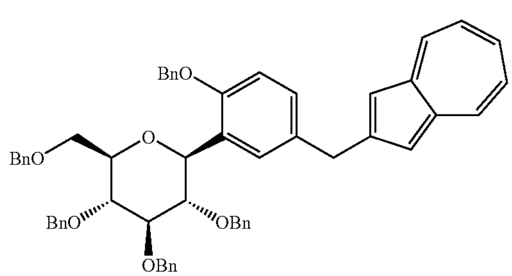 | ¹H-NMR(CDCl₃): 3.58–3.97 (7H, m), 4.29–4.99 (12H, m), 6.85–7.49 (33H, m), 8.08 (2H, d)<br>FAB-MS(m/z): 848[M +H]⁺ |

TABLE 22-continued

| Ex. | Structure | Data |
|---|---|---|
| 75 | 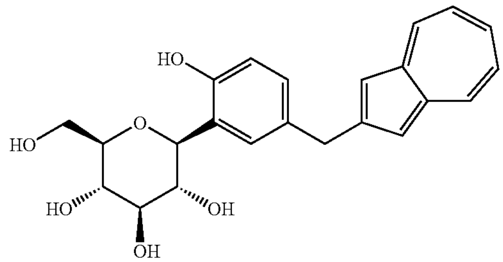 | $^1$H-NMR(CD$_3$OD): 3.37–3.59 (4H, m), 3.70 (1H, dd), 3.82 (1H, dd), 4.23 (2H, s), 4.56 (1H, d), 6.76 (1H, d), 7.02–7.16 (5H, m), 7.29 (1H, d), 7.49 (1H, dd), 8.17 (2H, d) <br> FAB-MS(m/z): 397[M +H]$^+$ |

TABLE 23

TABLE 23-continued
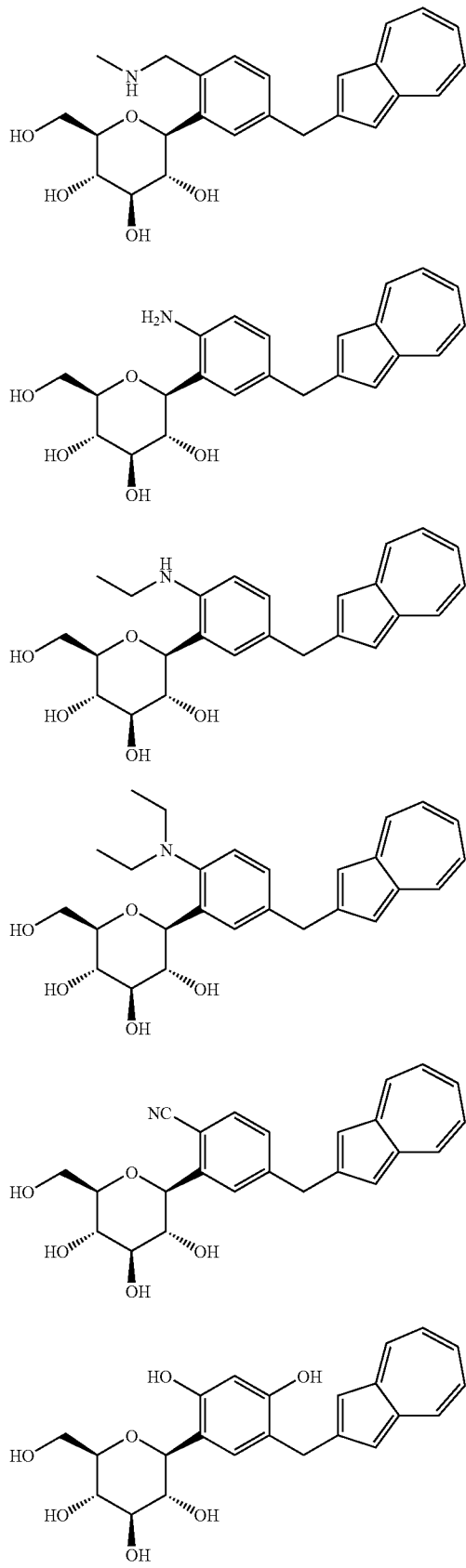
TABLE 23-continued
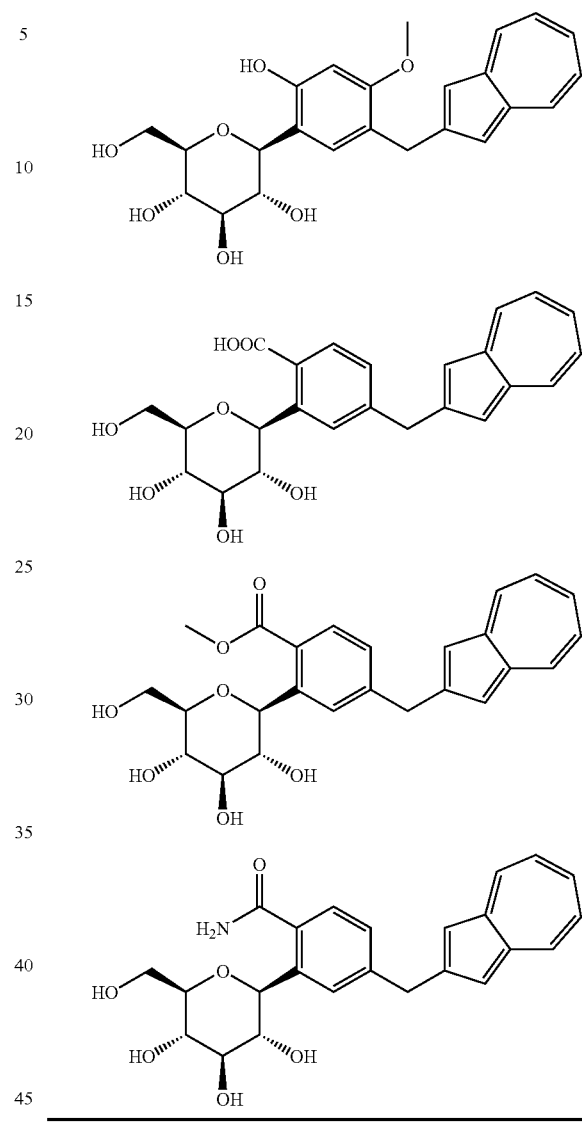
The invention claimed is:
1. An azulene derivative of following formula (I) or a salt thereof:
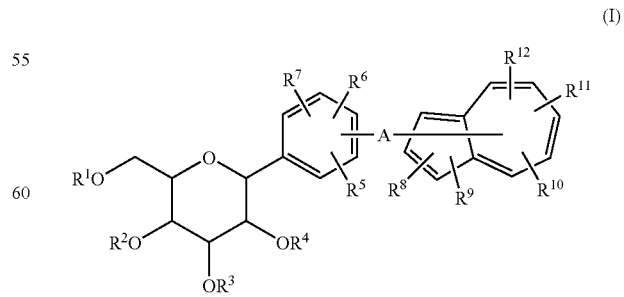
wherein $R^1$ to $R^4$ individually represent a hydrogen atom, optionally substituted lower alkyl, —C(═O)-optionally substituted lower alkyl, or —optionally substituted lower alkylene-optionally substituted aryl, R⁵ to R¹² individually represent a hydrogen atom, an optionally substituted lower alkyl, halogen atom, —OH, —O-optionally substituted lower alkyl, -optionally substituted lower alkylene-OH, -optionally substituted lower alkylene-O-optionally substituted lower alkyl, —O-optionally substituted lower alkylene-O-optionally substituted lower alkyl, —O-optionally substituted lower alkylene-optionally substituted aryl, -optionally substituted lower alkylene-O—C(═O)-optionally substituted lower alkyl, —COOH, nitro, cyano, amino, substituted amino, or —C(═O)—O-optionally substituted lower alkyl, and A represents a bond or an optionally substituted lower alkylene, wherein -A- may be bonded to any one of the positions 1–8 of the azulene ring, and any two of R⁵, R⁶, and R⁷ may form a benzene ring together with the adjacent carbon atoms, and wherein optionally substituted chemical groups are substituted with a haloaen atom, —OH, -lower alkylene-OH, —COOH, —C(═O)—O-lower alkyl, nitro, cyano, or an amino group.

2. The azulene derivative or the salt thereof according to claim 1, wherein the optionally substituted lower alkyl, —C(═O)-optionally substituted lower alkyl, and —optionally substituted lower alkylene-optionally substituted aryl represented by R¹ to R⁴ in the above formula (I) are respectively a lower alkyl, —C(═O)-lower alkyl, and -lower alkylene-aryl, the optionally substituted lower alkyl, —O-optionally substituted lower alkyl, -optionally substituted lower alkylene-OH, -optionally substituted lower alkylene-O-optionally substituted lower alkyl, —O-optionally substituted lower alkylene-optionally substituted alkyl, —O-optionally substituted lower alkylene-optionally substituted aryl, -optionally substituted lower alkylene-O—C(═O)-optionally substituted lower alkyl, and —C(═O)—O-optionally substituted lower alkyl represented by R⁵ to R¹² in the formula (I) are respectively a lower alkyl or a halogen-substituted lower alkyl, —O-lower alkyl, -lower alkylene-OH, -lower alkylene-O-lower alkyl, —O-lower alkylene-O-lower alkyl, —O-lower alkylene-aryl, -lower alkylene-O—C(═O)-lower alkyl, and —C(═O)—O-lower alkyl, wherein the optionally substituted lower alkylene represented by A in the above formula (I) is a lower alkylene or a halogen-substituted lower alkylene, and wherein optionally substituted chemical groups are substituted with a halogen atom, —OH, -lower alkylene-OH, —COOH, —C(═O)—O-lower alkyl, nitro, cyano, or an amino group.

3. The azulene derivative or the salt thereof according to claim 1, wherein the group represented by A in the above formula (I) is a lower alkylene.

4. The azulene derivative or the salt thereof according to claim 3, wherein the group represented by A in the above formula (I) is a methylene.

5. The azulene derivative or the salt thereof according to claim 1, wherein the groups represented by R¹ to R⁴ in the above formula (I) are hydrogen atoms.

6. The azulene derivative or the salt thereof according to claim 1, wherein the azulene derivative of the above formula (I) is at least one compound selected from the group consisting of 1,5-anhydro-1-[3-(azulen-2-ylmethyl)phenyl] hexytol, 1,5-anhydro-1-[5-(azulen-2-ylmethyl)-2-methoxyphenyl]hexytol, 1,5-anhydro-1-[3-(azulen-2-ylmethyl)-5-methoxyphenyl]hexytol, 1,5-anhydro-1-[3-(azulen-2-ylmethyl)-4-methoxyphenyl]hexytol, 1,5-anhydro-1-[5-(azulen-2-ylmethyl)-2-ethoxyphenyl]hexytol, 1,5-anhydro-1-[5-(azulen-2-ylmethyl)-2-methylphenyl]hexytol, 1,5-anhydro-1-[5-(azulen-2-ylmethyl)-2-hydroxyphenyl] hexytol, 1,5-anhydro-[5-(azulen-2-ylmethyl)-2-fluorophenyl]hexytol, 1,5-anhydro-1-[5-(azulen-2-ylmethyl)-2,4-dimethoxyphenyl]hexytol, and 1,5-anhydro-1-[4-(azulen-2-ylmethyl)-1-methoxy-2-naphthyl]hexytol.

7. A pharmaceutical composition containing an effective amount of an azulene derivative of following formula (I) or a salt thereof:

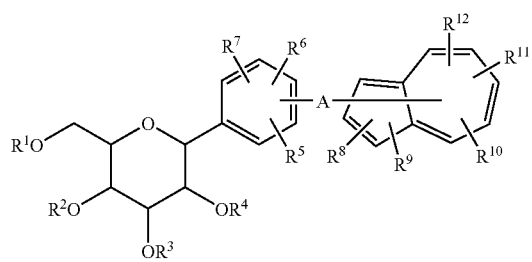

(I)

wherein R¹ to R⁴ individually represent a hydrogen atom, optionally substituted lower alkyl, —C(═O)-optionally substituted lower alkyl, or -optionally substituted lower alkylene-optionally substituted aryl, R⁵ to R¹² individually represent a hydrogen atom, an optionally substituted lower alkyl, halogen atom, —OH, —O-optionally substituted lower alkyl, -optionally substituted lower alkylene-OH, -optionally substituted lower alkylene-O-optionally substituted lower alkyl, —O-optionally substituted lower alkylene-O-optionally substituted lower alkyl, —O-optionally substituted lower alkylene-optionally substituted aryl, -optionally substituted lower alkylene-O—C(═O)-optionally substituted lower alkyl, —COOH, nitro, cyano, amino, substituted amino, or —C(═O)—O-optionally substituted lower alkyl, and A represents a bond or an optionally substituted lower alkylene, wherein -A- may be bonded to any one of the positions 1–8 of the azulene ring, and any two of R⁵, R⁶, and R⁷ may form a benzene ring together with the adjacent carbon atoms, and wherein optionally substituted chemical groups are substituted with a halogen atom, —OH, -lower alkylene-OH, —COOH, —C(═O)—O-lower alkyl, nitro, cyano, or an amino group and pharmaceutically acceptabe adjuvants.

8. A method of inhibiting a Na⁺-glucose cotransporter comprising administering an effective amount of the pharmaceutical composition according to claim 7 to a patient in need thereof.

9. A method for treating diabetes comprising administering an effective amount of an azulene derivative of following formula (I) or a salt thereof to a patient in need thereof:

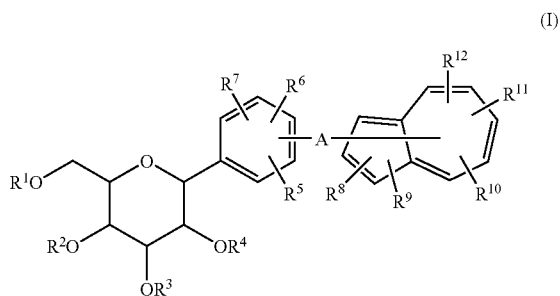

(I)

wherein $R^1$ to $R^4$ individually represent a hydrogen atom, optionally substituted lower alkyl, —C(=O)-optionally substituted lower alkyl, or —optionally substituted lower alkylene-optionally substituted aryl, $R^5$ to $R^{12}$ individually represent a hydrogen atom, an optionally substituted lower alkyl, halogen atom, —OH, —O-optionally substituted lower alkyl, -optionally substituted lower alkylene-OH, -optionally substituted lower alkylene-O-optionally substituted lower alkyl, —O-optionally substituted lower alkylene-O-optionally substituted lower alkyl, —O-optionally substituted lower alkylene-optionally substituted aryl, -optionally substituted lower alkylene-O—C(=O)-optionally substituted lower alkyl, —COOH, nitro, cyano, amino, substituted amino, or —C(=O)—O-optionally substituted lower alkyl, and A represents a bond or an optionally substituted lower alkylene, wherein -A- may be bonded to any one of the positions 1–8 of the azulene ring, and any two of $R^5$, $R^6$, and $R^7$ may form a benzene ring together with the adjacent carbon atoms, and wherein optionally substituted chemical groups are substituted with a halogen atom, —OH, -lower alkylene-OH, —COOH, —C(=O)—O-lower alkyl, nitro, cyano, or an amino group.

10. A method for treating diabetes comprising administering an effective amount of the azulene derivative or the salt thereof according to claim 9 to a patient in need thereof, wherein the optionally substituted lower alkyl, —C(=O)-optionally substituted lower alkyl, and -optionally substituted lower alkylene-optionally substituted aryl represented by $R^1$ to $R^4$ in the above formula (I) are respectively a lower alkyl, —C(=O)-lower alkyl, and -lower alkylene-aryl, the optionally substituted lower alkyl, —O-optionally substituted lower alkyl, -optionally substituted lower alkylene-OH, -optionally substituted lower alkylene-O-optionally substituted lower alkyl, —O-optionally substituted lower alkylene-O-optionally substituted lower alkyl, —O-optionally substituted lower alkylene-optionally substituted aryl, -optionally substituted lower alkylene-O—C(=O)-optionally substituted lower alkyl, and —C(=O)—O-optionally substituted lower alkyl represented by $R^5$ to $R^{12}$ in the formula (I) are respectively a lower alkyl or a halogen-substituted lower alkyl, —O-lower alkyl, -lower alkylene-OH, -lower alkylene-O-lower alkyl, —O-lower alkylene-O-lower alkyl, —O-lower alkylene-aryl, -lower alkylene-O—C(=O)-lower alkyl, and —C(=O)—O-lower alkyl, wherein the optionally substituted lower alkylene represented by A in the above formula (I) is a lower alkylene or a halogen-substituted lower alkylene, and wherein optionally substituted chemical groups are substituted with a halogen atom, —OH, -lower alkylene-OH, —COOH, —C(=O)—O-lower alkyl, nitro, cyano, or an amino group.

* * * * *

UNITED STATES PATENT AND TRADEMARK OFFICE
CERTIFICATE OF CORRECTION

PATENT NO. : 7,169,761 B2 Page 1 of 1
APPLICATION NO. : 10/491618
DATED : January 30, 2007
INVENTOR(S) : Tomiyama et al.

It is certified that error appears in the above-identified patent and that said Letters Patent is hereby corrected as shown below:

In Claim 1, column 93, line 23, "haloaen" should read --halogen--.

In Claim 1, column 93, line 37, after "alkylene-" insert -- O- --.

In Claim 6, column 94, line 10, after "anhydro" insert --1--.

Signed and Sealed this

First Day of May, 2007

JON W. DUDAS
*Director of the United States Patent and Trademark Office*